US 10,889,636 B2
Jan. 12, 2021

(12) United States Patent
Tam et al.

(10) Patent No.: US 10,889,636 B2
(45) Date of Patent: Jan. 12, 2021

(54) ANTI-LAMININ4 ANTIBODIES SPECIFIC FOR LG4-5

(71) Applicant: PROTHENA BIOSCIENCES LIMITED, County Dublin (IE)

(72) Inventors: Stephen Jed Tam, Belmont, CA (US); Yue Liu, Foster City, CA (US); Robin Barbour, Walnut Creek, CA (US); Theodore Yednock, Forest Knolls, CA (US); Kenneth Flanagan, Alameda, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

(21) Appl. No.: 15/918,937

(22) Filed: Mar. 12, 2018

(65) Prior Publication Data

US 2018/0208646 A1    Jul. 26, 2018

Related U.S. Application Data

(62) Division of application No. 14/656,619, filed on Mar. 12, 2015, now Pat. No. 10,059,761.

(60) Provisional application No. 62/068,349, filed on Oct. 24, 2014, provisional application No. 62/023,760, filed on Jul. 11, 2014, provisional application No. 61/952,132, filed on Mar. 12, 2014.

(51) Int. Cl.
| | |
|---|---|
| *A61K 47/68* | (2017.01) |
| *C07K 16/18* | (2006.01) |
| *G01N 33/574* | (2006.01) |
| *A61K 39/00* | (2006.01) |

(52) U.S. Cl.
CPC .......... *C07K 16/18* (2013.01); *A61K 47/6843* (2017.08); *A61K 47/6851* (2017.08); *G01N 33/57488* (2013.01); *A61K 2039/505* (2013.01); *C07K 2317/24* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/92* (2013.01); *G01N 2333/78* (2013.01)

(58) Field of Classification Search
None
See application file for complete search history.

(56) References Cited

U.S. PATENT DOCUMENTS

| | | | |
|---|---|---|---|
| 5,859,205 | A | 1/1999 | Adair et al. |
| 7,090,844 | B2 | 8/2006 | Bar-Eli et al. |
| 7,456,260 | B2 | 11/2008 | Rybak |
| 7,815,909 | B2 | 10/2010 | Heavner et al. |
| 7,915,225 | B2 | 3/2011 | Finck |
| 8,293,468 | B2 | 10/2012 | Prat et al. |
| 9,017,682 | B2 | 4/2015 | Prat et al. |
| 9,447,190 | B2 | 9/2016 | Flanagan et al. |
| 10,059,761 | B2 | 8/2018 | Tam et al. |
| 10,407,506 | B2 | 9/2019 | Liu |
| 10,407,507 | B2 | 9/2019 | Flanagan et al. |
| 10,414,825 | B2 | 9/2019 | Flanagan et al. |
| 10,584,177 | B2 | 3/2020 | Flanagan et al. |
| 10,654,920 | B2 | 5/2020 | Tam et al. |
| 2003/0068319 | A1 | 4/2003 | Bar Eli |
| 2003/0147809 | A1 | 8/2003 | Gudas |
| 2004/0053850 | A1 | 3/2004 | Krissansen et al. |
| 2005/0069541 | A1 | 3/2005 | Karlik et al. |
| 2006/0008523 | A1 | 4/2006 | Andya et al. |
| 2007/0269435 | A1 | 11/2007 | Gillies et al. |
| 2011/0014183 | A1 | 1/2011 | Prat et al. |
| 2011/0217237 | A1 | 8/2011 | Chen et al. |
| 2012/0134989 | A1 | 5/2012 | Maloney |
| 2013/0029463 | A1 | 8/2013 | Rotman et al. |
| 2013/0216556 | A1 | 8/2013 | Fowler et al. |
| 2014/0227292 | A1 | 8/2014 | Flanagan et al. |
| 2014/0314744 | A1 | 10/2014 | Flanagan et al. |
| 2015/0218266 | A1 | 8/2015 | Prat et al. |
| 2015/0239980 | A1 | 8/2015 | Flanagan et al. |
| 2015/0259408 | A1 | 9/2015 | Tam et al. |
| 2015/0259419 | A1 | 9/2015 | Liu et al. |
| 2017/0002077 | A1 | 1/2017 | Tam et al. |
| 2017/0002089 | A1 | 1/2017 | Liu |
| 2017/0037144 | A1 | 2/2017 | Flanagan et al. |
| 2017/0101470 | A1 | 4/2017 | Liu et al. |
| 2017/0145109 | A1 | 5/2017 | Flanagan et al. |
| 2017/0129954 | A1 | 6/2017 | Flanagan et al. |
| 2017/0158755 | A1 | 6/2017 | Flanagan et al. |
| 2018/0105602 | A1 | 4/2018 | Flanagan et al. |

(Continued)

FOREIGN PATENT DOCUMENTS

| | | |
|---|---|---|
| EP | 0 990 663 A2 | 4/2000 |
| EP | 2234600 B1 | 8/2014 |

(Continued)

OTHER PUBLICATIONS

Gonzalez et al (PNAS, 2002, 99:16075-16080).*

(Continued)

*Primary Examiner* — Laura B Goddard
(74) *Attorney, Agent, or Firm* — Alston & Bird LLP

(57) ABSTRACT

The invention provides antibodies that specifically bind to the LG4-5 modules of the G domain of laminin α4. The antibodies can preferentially stain cancer or tumor cells or tissue. The antibodies can be used for detecting cancer, evaluating the efficacy of a cancer therapy, treating cancer, and treating obesity or obesity-related diseases, among other applications.

9 Claims, 21 Drawing Sheets
(1 of 21 Drawing Sheet(s) Filed in Color)
Specification includes a Sequence Listing.

(56) References Cited

U.S. PATENT DOCUMENTS

| | | |
|---|---|---|
| 2018/0371067 A1 | 12/2018 | Tam et al. |
| 2020/0010563 A1 | 1/2020 | Liu |

FOREIGN PATENT DOCUMENTS

| | | |
|---|---|---|
| JP | 2005-514409 A | 5/2005 |
| JP | 2006-516085 A | 6/2006 |
| JP | 6339574 B | 5/2018 |
| WO | WO 2003/057006 A2 | 12/2002 |
| WO | WO 2003/057837 A1 | 7/2003 |
| WO | WO 2003/057838 A2 | 7/2003 |
| WO | WO 2007/058725 A2 | 5/2007 |
| WO | WO 2009/028663 A1 | 3/2009 |
| WO | WO 2009/054435 A1 | 4/2009 |
| WO | WO 2009/064854 A2 | 5/2009 |
| WO | WO 2009/093138 A1 | 7/2009 |
| WO | WO 2011/100477 A2 | 8/2011 |
| WO | WO 2012/024187 A1 | 2/2012 |
| WO | WO 2012/170071 A1 | 12/2012 |
| WO | WO 2012/170071 A2 | 12/2012 |
| WO | WO 2013/164789 A1 | 11/2013 |
| WO | WO 2013/186700 A1 | 12/2013 |
| WO | WO 2014/039975 A2 | 3/2014 |
| WO | WO 2014/039975 A3 | 3/2014 |
| WO | WO 2015/061584 A1 | 4/2015 |
| WO | WO 2015/136468 A1 | 9/2015 |
| WO | WO 2015/136469 A1 | 9/2015 |
| WO | WO 2015/136471 A1 | 9/2015 |
| WO | WO 2015/136472 A1 | 9/2015 |
| WO | WO 2015/136570 A1 | 9/2015 |
| WO | WO 2017/046774 A2 | 3/2017 |
| WO | WO 2017/046776 A2 | 3/2017 |
| WO | WO 2017/149513 A1 | 9/2017 |
| WO | WO 2017/208210 A1 | 12/2017 |
| WO | WO 2018/223140 A1 | 12/2018 |

OTHER PUBLICATIONS

Talts et al (Journal of Biological Chemistry, 2000, 275:35192-35199).*
Ishikawa et al (Matrix Biology, 2014, 36:5-14).*
Ross (Rockefeller University, "Molecular Determinants of Tumor Re-Initiation in Breast Cancer" (2015). Student Theses and Dissertations. Paper 289).*
Li et al (EBioMedicine, 2019, 44:439-451).*
Vaicik et al (PLoS ONE, 2014; 13:e109854).*
U.S. Appl. No. 15/222,848, filed Jul. 28, 2016; now issued U.S. Pat. No. 10,407,507 on Sep. 10, 2019.
U.S. Appl. No. 15/726,170, filed Oct. 5, 2017.
U.S. Appl. No. 15/918,937, filed Mar. 12, 2018.
U.S. Appl. No. 15/991,998, filed May 29, 2018.
Abaza, et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," Journal of Protein Chemistry, vol. 11, No. 5, pp. 433-444, (1992).
Archelos, et al., "Inhibition of Experimental Autoimmune Encephalomyelitis by an Antibody to the Intercellular Adhesion Molecule ICAM-1," Ann Neurol, 34:145-154 (1993).
Awad, et al., "Cyclophosphamide in multiple sclerosis scientific rationale, history and novel treatment paradigms," Ther Adv Neurol Disord, 2(16) 357-368 (2009).
Bardin, et al., "Identification of the S-Endo 1 endothelial-associated antigen," Biochem Biophys Res Commun, 5;218(1):210-216, (Jan. 1996).
Bar-Eli, "Molecular mechanisms of melanoma metastasis," J Cell Physiol, 173(2):275-278, (Nov. 1997).
Bar-Eli, "Role of AP-2 in tumor growth and metastasis of human melanoma." Cancer Metastasis Rev,18(3):377-385, (1999).
Beutel, et al., "Possible Implications of MCAM Expression in Metastasis and Non-Metastatic of Primary Uveal Melanoma Patients," Current Eye Research, 34(11, 1004-1009, (2009).
Brucklacher-Waldert, et al., "Phenotypical and functional characterization of T helper 17 cells in multiple sclerosis," Brain, 132:3329-3341 (2009).
Bu, et al., "Anti-CD146 monoclonal antibody AA98 inhibits angiogenesis via suppression of nuclear factor-κB activation", Mol Cancer Ther., 5(11)2872-2878 (Nov. 2006).
Chen, et al., "Is CD146 pivotal in neoplasm invasion and blastocyst embedding?" Med Hypotheses, 76(3):378-380, (Mar. 2001).
Dagur, et al., "MCAM-expressing CD4(+) T cells in Peripheral Blood Secrete IL-17A and are Significantly Elevated in Inflammatory Autoimmune Diseases," J Autoimmun, 37(4):319-27 (Dec. 2011).
Dehahn, et al., "The α4 laminin subunit regulates endothelial cell survival", Experimental Cell Research, 294:281-289, (2004).
Denton, et al., "A study of adhesion molecules as markers of progression in malignant melanoma," J Pathol, 167(2):187-191, (Jun. 1992).
Despoix, et al., "Mouse CD146/MCAM is a marker of natural killer cell maturation," Eur J Immunol, 38(10):2855-64 (2008).
Duan, et al., "Targeting endothelial CD146 attenuates neuroinflammation by limiting lymphocyte extravasation to the CNS," Sci Rep. 3:1687:1-11, (2013).
Duda, et al., "Differential CD146 expression on circulating versus tissue endothelial cells in rectal cancer patients: implications for circulating endothelial and progenitor cells as biomarkers for antiangiogenic therapy," J Clin Oncol., 20;24(9):1449-53, (Mar. 20, 2006).
Dye, et al., "hShroom1 links a membrane bound protein to the actin cytoskeleton. Cell Mol Life Sci," 66(4):681-696, (Feb. 2009).
Dye, et al., "Melanoma Biomolecules: Independently Identified but Functionally Intertwined," Front Oncol., 3:252:1-17, (Sep. 24, 2013).
Elmageed, et al., "Clinical significance of CD146 and latexin during different stages of thyroid cancer," Mol Cell Biochem, 381:95-103 (2013).
Elshal, et al., "A unique population of effector memory lymphocytes identified by CD146 having a distinct immunophenotypic and genomic profile," BMC Immunol., 8:29:1-15, (Nov. 13, 2007).
Elshal, et al., "CD146 (Mel-CAM), an adhesion marker of endothelial cells, is a novel marker of lymphocyte subset activation in normal peripheral blood," Blood,106(8):2923-2924, (Oct. 15, 2005).
EP Application No. 13836030.0 (Published as EP 2892562), Supplementary European Search Report and European Search Opinion, dated Apr. 4, 2016.
Feng, et al., "CD146 gene expression in clear cell renal cell carcinoma: a potential marker for prediction of early recurrence after nephrectomy," Int Urol Nephrol, 44:1663-1669 (2012).
Filshie, et al., "MUC18, a member of the immunoglobulin superfamily, is expressed on bone marrow fibroblasts and a subset of hematological malignancies," Leukemia, 12:414-421 (1998).
Flanagan, "Prothena to Present Precinical Data for PRX003 at 2016 AAAAI Annual Meeting," (Mar. 6, 2016).
Flanagan, "Anti-Mcam Monoclonal Antibody PRX003 Inhibits the Unique Migratory Potential of Pathogenic IL-17-Producing T Cells," J Allergy Clin Immunol, AB190 Abtracts, (Feb. 2016).
Flanagan, et al., "Laminin-411 Is a Vascular Ligand for MCAM and Facilitates TH17 Cell Entry into the CNS," PLoS One, vol. 7, Issue 7, (2012).
Flanagan, et al., "Laminin-411 is a vascular ligand for MCAM and facilitates TH17 cell entry into the CNS," PLoS One, 7(7):1-11, (2012).
Freeman, et al., "Evaluation of a multi-marker immunomagnetic enrichment assay for the quantification of circulating melanoma cells," J Transl Med., 10:192:1-9, (Sep. 15, 2012).
Galvez, "Role of Th17 Cells in the Pathogenesis of Human IBD," ISRN Inflammation, vol. 201.4, Article ID 938461, 14 pages, retrieved from <http://dx.doi.org/10.1155/2014/928461> (2014).
Geberhiwot, et al., "Rapid communication Erythromegakaryocytic Cells Synthesize Laminin-8 (α4β1γ1)", Experimental Cell Research, 254 189-195, (2000).
Gonzales, et al., "Structure and Function of a Vimentin-associated Matrix Adhesion in Endothelial Cells", Molecular biology of the Cell, vol. 12, 85-100 (Jan. 2001).

(56) References Cited

OTHER PUBLICATIONS

Gonzalez, et al., "Complex interactions between the laminin α4 subunit and integrins regulate endothelial cell behavior in vitro and angiogenesis in vivo", PNAS, vol. 99, No. 25, 16075-16080 (Dec. 10, 2002).
Gould Rothberg, et al., "Tissue biomarkers for prognosis in cutaneous melanoma: a systematic review and meta-analysis," *J Natl Cancer Inst*, 1;101(7):452-474, (Apr. 2009).
Grimm, et al., "Ectopic expression of carcinoembryonic antigen by a melanoma cell leads to changes in the transcription of two additional cell adhesion molecules," *Cancer Res.*, 55(15):3254-3257, (Aug. 1, 1995).
Guezguez, et al., "A dileucine motif targets MCAM-I cell adhesion molecule to the basolateral membrane in MDCK cells," *FEBS Lett*, 580(15):3649-3656. (Jun. 26, 2006).
Guezguez, et al., "Dual role of Melanoma Cell Adhesion Molecule (MCAM)/CD146 in Lymphocyte Endothelium Interaction: MCAM/CD146 Promotes Rolling via Microvilli Induction in Lymphocyte and Is an Endothelial Adhesion Receptor," *Journal of Immunology*, 179:6673-6685 (2007).
Guezguez, et al., "Dual role of melanoma cell adhesion molecule MCAM)/CD146 in lymphocyte endothelium interaction: MCAM/CD146 promotes rolling via microvilli induction in lymphocyte and is an endothelial adhesion receptor," *J Immunol.*, 79(10):6673-6685, (Nov. 15, 2007).
Hadjinicolaou, et al., "Relationship of CD146 expression to activation of circulating T cells: exploratory studies in healthy donors and patients with connective tissue disease," *Clin Exp Immunol.*, 174(1):73-88 (Oct. 2013).
Hafner, et al., "Selection of Mimotopes of the Cell Surface Adhersion Molecule Mel-CAM from a Random pVIII-28aa Phage Peptide Library," *The Journal of Investigative Dermatology*, vol. 119, No. 4, pp. 865-869, (Oct. 2002).
Hansen, et al., "Laminin-8/9 is synthesized by a rat glomerular mesangial cells and is required for PDGF-induced mesangial cell migration", Kidney International, vol. 64, pp. 110-118, (2003).
Heimberger, et al., "Loss of the AP-2alpha transcription factor is associated with the grade of human gliomas," *Clin Cancer Res.*, 11(1):267-272, (Jan. 1, 2005).
Huang, et al., "LAMA4, highly expressed in human hepatocellular carcinoma from Chinese patients, is a novel marker of tumor invasion and metastasis", J. Cancer Res. Clin. Oncol., 134:705-714, (2008).
Hung, et al., "The motor protein KIF14 inhibits tumor growth and cancer metastasis in lung adenocarcinoma," *PLoS One*, 8(4):1-14, (Apr. 23, 2013).
Imbert, et al., "CD146 expression in human breast cancer cell lines induces phenotypic and functional changes observed in Epithelial to Mesenchymal Transition," *PLoS One*, 7(8):1-8, (2012).
Ishikawa, et al., "Monoclonal antibodies to human laminin α4 chain globular domain inhibit tumor cell adhesion and migration on laminins 411 and 421, and binding of α6β1 integrin and MCAM to α4-laminins", Matrix Biology, 36:5-14 (2014).
Jarasch, et al., "Developability Assessment During the Selection of Novel Therapeutic Antibodies", *Journal of Pharmaceutical Sciences*, 104:1855-1898 (2015).
Jean, et al., "Loss of AP-2 results in up-regulation of MCAM/MUC18 and an increase in tumor growth and metastasis of human melanoma cells," *J Biol Chem.*, 273(26):16501-16508, (Jun. 26, 1998).
Jean, et al., "Targeting the ATF-1/CREB transcription factors by single chain Fv fragment in human melanoma: potential modality for cancer therapy," *Crit Rev Immunol*, 21(1-3):275-86, (2001).
Jiang, et al., "CD146 is a coreceptor for VEGFR-2 in tumor angiogenesis. *Blood*," 120(11):2330-2339, (Sep. 13, 2012).
Johnson, "Cell adhesion molecules in the development and progression of malignant melanoma," Cancer Metastasis Rev. 18(3):345-357, (1998).

Johnson, "Cell adhesion molecules of the immunoglobulin supergene family and their role in malignant transformation and progression to metastatic disease," Cancer Metastasis Rev. 10(1):11-22, (May 1991).
Johnson, et al, "MUC18: A cell adhesion molecule with a potential role in tumor growth and tumor cell dissemination," *Curr Top Microbiol Immunol*, 213 ( Pt 1):95-105, (1996).
Johnson, et al., "Functional aspects of three molecules associated with metastasis development in human malignant melanoma," *Invasion Metastasis*, 9(6):338-350, (1989).
Johnson, et al., "Melanoma Progression-Associated Glycoprotein MUC18/MCAM Mediates Homotypic Cell Adhesion Through Interaction With a Heterophilic Ligand," *Int. J. Cancer*, 73:769-774 (1997).
Johnson, et al., "The progression associated antigen MUC18: a unique member of the immunoglobulin supergene family," *Melanoma Res*, 3(5):337-340, (Oct. 1993).
Kamiyama, et al., Coexpression of CCR6 and CD146 (MCAM) is a marker of effector memory T-helper 17 cells, J Dermatol. 39(10):838-842, (Oct. 2012).
Kapoor, et al., "CD146 expression and its close relationship to tumor progression in systemic malignancies besides gall bladder carcinomas," *Tumour Biol.*, 34(2):1273-4 (Apr. 2013).
Katagiri, et al., "Screening of integrin-binding peptides from the laminin α4 and α5 chain G domain peptide library", Archives of Biochemistry and Biophysics, 521:32-42, (2012).
Kinney, et al., "Clinical Assessment of the Monoclonal Antibody, PRX003, a Potential Novel Treatment for Th17-Mediated Inflammatory Disease," *Arthritis Rheumatol*, vol. 68, No. Suppl 10, (Sep. 28, 2016).
Koller, et al., "OPO205 Clinical and Preclinical Assessment of the Anti-MCAM Monoclonal Antibody PRX003, a Potential Novel Treatment for Th17-Mediated Inflammatory Disease," *Annals of the Rheumatic Diseases*, vol. 75, No. Suppl 2, (Jun. 2016).
Kraus, et al, "Analysis of the expression of intercellular adhesion molecule-1 and MUC18 on benign and malignant melanocytic lesions using monoclonal antibodies directed against distinct epitopes and recognizing denatured, non-glycosylated antigen," *Melanoma Res*, Suppl 2:S75-81, (Aug. 1997).
Kristiansen, et al., "Expression of the cell adhesion molecule CD146/MCAM in non-small cell lung cancer," *Anal Cell Pathol*, 25(2):77-81, (2003).
Lai, et al., "Expression and distribution of MUC18 in human uveal melanoma," *Virchows Arch*, 451(5):967-76, (Nov. 2007).
Larochelle, et al., "Melanoma cell adhesion molecule identifies encephalitogenic T lymphocytes and promotes their recruitment to the central nervous system," *Brain*, 135(Pt 10):2906-2924, (Oct. 2012).
Larochelle, et al., "Melanoma Cell Adhesion Molecule-jPositive CD8 T Lymphocytes Mediate Central Nervous System Inflammation", 78(1):39-53 (2015).
Lehmann, et al., "MUC18, a marker of tumor progression in human melanoma, shows sequence similarity to the neural cell adhesion molecules of the immunoglobulin superfamily," *Proc Natl Acad Sci USA*, 1989 (24):9891-9895, (Dec. 1986).
Lei, et al., "The multifaceted role of CD146/MCAM in the promotion of melanoma progression", *Cancer Cell International*, 15:3 1-11 (2015).
Leslie, et al., "Immunization against MUC18/MCAM, a novel antigen that drives melanoma invasion and metastasis," *Gene Ther*, 14(4):316-323, (Oct. 5, 2006).
Leslie, et al., "Regulation of gene expression in melanoma: new approaches for treatment," *J Cell Biochem*, 94(1):25-38, (Jan. 2005).
Li, et al., "Increased expression of CD146 and microvessel density (MVD) in invasive micropapillary carcinoma of the breast: Comparative study with invasive ductal carcinoma-not otherwise specified," *Pathol Res Pract*, 207(12):739-746, (Dec. 15, 2011)
Li, et al., "Reciprocal regulation of MelCAM and AKT in human melanoma," *Oncogene*, 9;22(44):6891-6899. (Oct. 2003).

(56) References Cited

OTHER PUBLICATIONS

Lian, et al., "Identification of an active site on the laminin α4 chain globular domain that binds to αvβ3 integrin and promotes angiogenesis", Biochemical and Biophysical Research Communications, 347: 248-253, (2006).
Liu, et al., "Hypermethylation of MCAM gene is associated with advanced tumor stage in prostate cancer," *Prostate*, 68(4):418-426, (Mar. 1, 2008).
Ljubimova, et al., "Association between laminin-8 and glial tumor grade, recurrence, and patient survival," *Cancer*, 1;101(3):604-612, (Aug. 1, 2012).
Llie, et al., "Clinical value of circulating endothelial cells and of soluble CD146 levels in patients undergoing surgery for non-small cell lung cancer.," *Br J Cancer*, (Jan. 28, 2014).
Loricera, et al., "Tocilizumab in giant cell arteritis: Multicenter open-label study of 22 patients", *Seminars in Arthritis and Rheumatism*, 44:717-723 (2015).
Luca, et al., "Direct correlation between MUC18 expression and metastatic potential of human melanoma cells," *Melanoma Res*, 3(1):35-41. (Feb. 1993).
Luca, et al., "Molecular changes in human melanoma metastasis," *Histol Histogathol*, 13(4):1225-1231, (Oct. 1998).
Luo, et al., "Recognition of CD146 as an ERM-binding protein offers novel mechanisms for melanoma cell migration," *Oncogene*, 31(3):306-321, (Jan. 19, 2012).
Ma, et al., "Synergistic killing effect between vorinostat and target of CD146 in malignant cells," *Clin Cancer Res*, 1;16(21):5165-5176, (Nov. 2010).
Maggi, et al., "CD161 is a marker of all human IL-17-producing T-cell subsets and is induced by RORC," *Eur J Immunol*, 40(8):2174-2181, (Aug. 2010).
Malpass, "Disease mechanisms in MS: Cell adhesion molecule MCAM on pathogenic T cells—a green light for CNS entry in multiple sclerosis," *Nat Rev Neurol*, 8(11):592, (Nov. 5, 2012).
Mantovani, "Inflaming metastasis," Nature, 457:36-37, (2009).
Matsuura, et al., "Localization of the Laminin αChain in the Skin and Identification of a Heparin-Dependent Cell Adhesion site within the Laminin α4 Chain C-Terminal LG 4 Module," The Journal of Investigative Dermatology, 122:614-620 (2004).
McGary, et al., "A fully human antimelanoma cellular adhesion molecule/MUC18 antibody inhibits spontaneous pulmonary metastasis of osteosarcoma cells in vivo," *Clin Cancer Res*, 15;9(17):6560-6566, (Dec. 2003).
McGary, et al., "Cellular adhesion pathways and metastatic potential of human melanoma," *Cancer Biol Ther*, 1(5):459-465, (Sep.-Oct. 2002).
Melnikova, et al., "Bioimmunotherapy for melanoma using fully human antibodies targeting MCAM/MUC18 and IL-8," *Pigment Cell Res*, 19(5):395-405, (Oct. 2006).
Mills, et al., "Fully human antibodies to MCAM/MUC18 inhibit tumor growth and metastasis of human melanoma," *Cancer Res*, 1;62(17):5106-5114, (Sep. 2002).
Minato, et al., "Comparative immunohistochemical analysis of IMP3, GLUT1, EMA, CD146, and desmin for distinguishing malignant mesothelioma from reactive mesothelial cells," *Am J Clin Pathol*, 141(1):85-93, (Jan. 2014).
Mintz-Weber, et al., "Identification of the elements regulating the expression of the cell adhesion molecule MCAM/MUC18. Loss of AP-2 is not required for MCAM expression in melanoma cell lines," *J Biol Chem*, 3;275(44):34672-34680, (Nov. 2000).
Mukhopadhyay, "Granulomatous Lung Disease," *Arch Pathol Lab Med*, vol. 134, pp. 667-690, (May 2010).
Neidhart, et al., "Synovial fluid CD146 (MUC18), a marker for synovial membrane angiogenesis in rheumatoid arthritis," *Arthritis Rheum*, 42(4):622-630, (Apr. 1999).
Nobbmann, et al., "Dynamic light scattering as a relative tool for assessing the molecular integrity and stability of monoclonal antibodies", *Biotechnology and Genetic Engineering Review*, vol. 24, 117-128 (2007).
Nyormoi, et al., "Transcriptional regulation of metastasis-related genes in human melanoma," *Clin Exp Metastasis*, 20(3):251-63, (2003).
Ody, et al., "Surface molecules involved in avian T-cell progenitor migration and differentiation," *Dev Immunol*, 7(2-4):267-277, (2007).
Oikawa, et al., "Melanoma cells produce multiple laminin isoforms and strongly migrate on α5 laminin(s) via several integrin receptors", Experimental Cell Research, 317:1110-1133, (2011).
Oka, et al., "The expression of CD146 predicts a poor overall survival in patients with adenocarcinoma of the lung," *Anticancer Res.*, 32(3):861-4 (2012).
Okazaki, et al., "CD146 and insulin-like growth factor 2 mRNA-binding protein 3 predict prognosis of asbestos-induced rat mesothelioma," *Cancer Sci*, 104(8):989-995, (Aug. 2013).
Okumura, et al., "Involvement of gicerin in the extension of microvilli," *Exp Cell Res*, 271(2):269-276, (Dec. 10, 2001).
Ouhtit, et al., "Towards understanding the mode of action of the multifaceted cell adhesion receptor CD146," *Biochim Biophys Acta*, 1795(2):130-136. (Apr. 2009).
Pacifico, et al., "Development of a tissue array for primary melanoma with long-term follow-up: discovering melanoma cell adhesion molecule as an important prognostic marker," *Plast Reconstr Surg.*, 115(2):367-75, (2005).
Pantel, et al., "Early metastasis of human solid tumours: expression of cell adhesion molecules," *Ciba Found Symp*, 189:157-170; (1995).
Pardo, et al., "The characterization of the invasion phenotype of uveal melanoma tumour cells shows the presence of MUC18 and HMG-1 metastasis markers and leads to the identification of DJ-1 as a potential serum biomarker," *Int J Cancer*, 1;119(5):1014-1022, (Sep. 2006).
PCT/IB2015/051785 International Preliminary Report on Patentability and Written Opinion dated Sep. 13, 2016.
PCT/IB2015/051785 International Search Report and Written Opinion dated Jul. 23, 2015.
PCT/IB2015/051786 International Preliminary Report on Patentability and Written Opinion dated Sep. 13, 2016.
PCT/IB2015/051786 International Search Report and Written Opinion dated Aug. 26, 2015.
PCT/IB2015/0517863 Invitation to Pay Additional Fees and, Where Applicable, Protest Fee dated Jun. 17, 2015.
PCT/IB2015/051787 International Preliminary Report on Patentability and Written Opinion dated Sep. 13, 2016.
PCT/IB2015/051787 International Search Report and Written Opinion dated Jun. 22, 2015.
PCT/IB2015/051789 International Preliminary Report of Patentability and Written Opinion dated Sep. 10, 2016.
PCT/IB2015/051789 International Search Report and Written Opinion dated Aug. 13, 2015.
PCT/IB2015/051790 International Preliminary Report on Patentability and Written Opinion dated Sep. 13, 2016.
PCT/IB2015/051790 International Search Report and Written Opinion dated Jun. 25, 2015.
PCT/IB2016/055557 International Preliminary Report on Patentability dated Mar. 29, 2018.
PCT/IB2016/055557 International Search Report and Written Opinion dated Apr. 7, 2017.
PCT/IB2016/055557 Invitation to Pay Additional Fees and, Where Applicable, Protest Fee dated Dec. 6, 2016.
PCT/IB2016/055559 International Preliminary Report on Patentability and Written Opinion dated Mar. 31, 2017.
PCT/IB2016/055559 International Preliminary Report on Patentability dated Mar. 29, 2018.
PCT/IB2016/055559 Invitation to Pay Additional Fees, and, Where Applicable, Protest Fee dated Dec. 5, 2016.
PCT/IB2017/051264 Invitation to Pay Additional Fees and, Where Applicable, Protest Fee dated May 22, 2017.
PCT/IB2017/051402 International Search Report and Written Opinion dated Aug. 8, 2017.
PCT/IB2017/05142 International Search Report and Written Opinion dated Aug. 8, 2017.
PCT/IB2017/05142 Invitation to Pay Additional Fees and, Where Applicable, Protest Fee dated Jun. 2, 2017.

(56) References Cited

OTHER PUBLICATIONS

PCT/IB2017/053289 International Search Report and Written Opinion dated Aug. 8, 2017.
PCT/IB2017051264 International Search Report and Written Opinion dated Aug. 8, 2017.
PCT/US2012/000274 International Preliminary Report of Patentability and Written Opinion dated Dec. 10, 2013.
PCT/US2012/000274 International Search Report dated Sep. 26, 2012.
PCT/US2013/058773 International Search Report and Written Opinion dated Apr. 16, 2014.
PCT/US2013/058773 Invitation to Pay Additional Fees and, Where Applicable, Protest Fee dated Jan. 23, 2014.
PCT/US2013/058773 Preliminary report on Patentability dated Mar. 19, 2015.
Perego, et al., "Heterogeneous phenotype of human melanoma cells with in vitro and in vivo features of tumor-initiating cells," *J Invest Dermatol*, 130(7):1877-1886, (Jul. 2010).
Petajaniemi, et al., "Localization of laminin alpha4-chain in developing and adult human tissues," *J Histochem Cytochem*, 50(8):1113-1130, (Aug. 2002).
Pickl, et al., "MUC18/MCAM (CD146), an activation antigen of human T lymphocytes," *J Immunol*, 158(5):2107-2115, (Mar. 1, 1997).
Pierce, et al., "Expression of Laminin α3, α4, and α5 Chains by Alveolar Epithelial Cells and Fibroblasts", American Journal of Respiratory Cell and Molecular Biology, vol. 19, pp. 237-244 (1998).
Pires, et al., "Mel-CAM (CD146) expression in parotid mucoepidermoid carcinoma," *Oral Oncology*, 39:277-281 (2003).
Prothena, "Prothena Reports Results of Phase 1 Single Ascending Dose Study of PRX003, Demonstrating Target Engagement of the Novel Anti-MCAM Antibody for Inflammatory Disease", Jun. 9, 2016, Retrieved from the Internet: URL:http://files.shareholder.com/downloads/AMDA-1GZ5QD/4888716237x0x895935/C8896509-F11C-4742-PFFD-AD031305F573/PRTA_News_2016_6_9_General_Releases.pdf retrieved on Jul. 31, 2017.
Pujades, et al., "Melanoma Cell Adhesion Molecule (MCAM) expression in the myogenic lineage during early chick embryonic development," *Int J Dev Biol*, 46(2):263-266, (Mar. 2002).
Rapanotti, et al., "Blood MUC-18/MCAM expression in patients with melanoma: a suitable marker of poor outcome," *Br J Dermatol*, 169(1):221-222, (Jul. 2013).
Rapanotti, et al., "Melanoma-associated markers expression in blood: MUC-18 is associated with advanced stages in melanoma patients," *Br J Dermatol*, 160(2):338-344, (Feb. 2008).
Reboldi, et al., "C-C chemokine receptor 6-regulated entry of TH-17 cells into the CNS through the choroid plexus is required for the initiation of EAE," *Nat Immunol*, 10(5):514-523, (May 2009).
Reid, et al., "Markers of circulating tumour cells in the peripheral blood of patients with melanoma correlate with disease recurrence and progression," *Br J Dermatol*, 168(1):85-92. (Jan. 2013).
Rice, et al., "Anti-α4 integrin therapy for multiple sclerosis", *Neurology*, 64:1336-1342 (2005).
Roep, et al., "The problems and promises of research into human immunology and autoimmune disease", Nature Medicine, 18(1):48-53 (2012).
Romagnani, et al., "Properties and origin of human Th17 cells," *Mol Immunol*, 47(1):3-7, (Nov. 2009).
Rose, "Prothena Ends an early Stage Psoriasis Drug After Data Failed to Wow its Researchers," *Filter News*, pp. 1-6, (Sep. 29, 2017).
Rose, Prothena Reports Results from Phase 1 b Multiple Ascending Dose Study of PRX003 in Patients with Psoriasis,Press Release, Sep. 28, 2017.
Rossi, et al., "Vascular inflammation in central nervous system diseases: adhesion receptors controlling leukocyte-endothelial interactions," Journal of Leukocyte Biology, 89:529-556 (2011).

Sato, et al., "Immunocytochemistry of CD146 is useful to discriminate between malignant pleural mesothelioma and reactive mesothelium," *Mod Pathol*, 23(11):1458-1466, (Nov. 2010).
Satyamoorthy, et al., "Mel-CAM-specific genetic suppressor elements inhibit melanoma growth and invasion through loss of gap junctional communication," *Oncogene*, 2;20(34):4676-4684, (Aug. 2001).
Schiano, et al., "Different expression of CD146 in human normal and osteosarcoma cell lines," *Med Oncol*, 29(4):2998-3002. (Dec. 2012).
Schlagbauer-Wadl, et al., "Influence of MUC18/MCAM/CD146 expression on human melanoma growth and metastasis in SCID mice," *Int J Cancer*, 11;81(6):951-955, (Jun. 1999).
Schrage, et al., "Murine CD146 is widely expressed on endothelial cells and is recognized by the monoclonal antibody ME-9F1," *Histochem Cell Biol*,129(4):441-451, (Apr. 2008).
Schwarz, et al., "Melanoma-associated adhesion molecule MUC18/MCam (CD146) and transcriptional regulator mader in normal human CNS," *Neuroimmunomodulation*, 5(5):270-276, (Sep.-Oct. 1998).
Sers, et al., "Genomic organization of the melanoma-associated glycoprotein MUC18: implications for the evolution of the immunoglobulin domains," *Proc Natl Acad Sci USA*, 15;90(18):8514-8518, (Sep. 1993).
Sers, et al., "MUC18, a melanoma-progression associated molecule, and its potential role in tumor vascularization and hematogenous spread," *Cancer Res*, 1; 54(21):5689-5694. (Nov. 1994).
Shih et al., "A New Mel-Cam (CD146)-Specific Monoclonal Antibody, MN-4, on Paraffin-Embedded Tissue",*Modern Pathology*, 11(11):1098-1106, (1998).
Shih, "The role of CD146 (Mel-CAM) in biology and pathology," *J Pathol*, 189(1):4-11, (Sep. 1999).
Shih, et al., "Melanoma cell-cell interactions are mediated through heterophilic Mel-CAM/ligand adhesion," *Cancer Res*, 1;57(17):3835-3840, (Sep. 1997).
Shih, et al., "Regulation of Mel-CAM/MUC18 expression on melanocytes of different stages of tumor progression by normal keratinocytes," *Am J Pathol*, 145(4):837-845, (Oct. 1994).
Shih, et al., "The cell-cell adhesion receptor Mel-CAM acts as a tumor suppressor in breast carcinoma," *Am J Pathol*, 151(3):745-751, (Sep. 1997).
Sixt, et al., "Endothelial cell laminin isoforms, laminins 8 and 10, play decisive roles in T cell recruitment across the blood-brain barrier in experimental autoimmune encephalomyelitis," *J Cell Biol*, 28;153(5):933-946, (May 2001).
Solovey, et al., "Identification and functional assessment of endothelial P1H12," *J Lab Clin Med*, 138(5):322-331, (Nov. 2001).
Stalin, et la., "Therapeutic and Diagnostic Antibodies to CD146: Thirty Years of Research on Its Potential for Detection and Treatment of Tumors," *Antibodies*, 6, 17, doi:10.33090/antib6040017, (2017.
Takaha, et al., "Expression of gicerin in development, oncogenesis and regeneration of the chick kidney," *Differentiation*, 58(5):313-320, (Jun. 1995).
Talts, et al., "Structural and Functional Analysis of the Recombinant G. Domain of the Laminin α4 Chain and Its Proteolytic Processing in Tissues", The Journal of Biological Chemistry, vol. 275, No. 45, pp. 35192-35199, (Nov. 10, 2000).
Taylor, "Prothena scratches MCAM psoriasis antibody after negative trial," *Gene Therapy & Immunotherapy; Alphabetical Glossary of Terms*, revised 22nd Edition, Sep. 29, 2017.
Tian, et al., "CD146 protein as a marker to predict postoperative liver metastasis in colorectal cancer," *Cancer Biother Radiopharm*, 28(6):466-470, (Jul.-Aug. 2013).
Tsuchiya, et al., Gicerin, a cell adhesion molecule, promotes the metastasis of lymphoma cells of the chicken, *Cell Tissue Res*, 314(3):389-397, (Dec. 2003).
Tsukamoto, aet al., "Involvement of gicerin, a cell adhesion molecule, in development and regeneration of oviduct and metastasis of oviductal adenocarcinomas of the chicken," *Exp Cell Res*, 247(2):329-338, (Mar. 15, 1999).

(56) References Cited

OTHER PUBLICATIONS

Tsukamoto, et al., "E. Gicerin, an Ig-superfamily cell adhesion molecule, promotes the invasive and metastatic activities of a mouse fibroblast cell line," *J Cell Physiol*, 197(1):103-109, (Oct. 2003).
Tsukamoto, et al., "Expression of gicerin enhances the invasive and metastatic activities of a mouse mammary carcinoma cell line," *Int J Oncol*, 23(6):1671-1677, (Dec. 2003).
Tsukamoto, et al., The role of gicerin, a novel cell adhesion molecule, in development, regeneration and neoplasia, *Histol Histobathol*, 16(2):563-571, (Apr. 2001).
U.S. Appl. No. 14/021,777 Final Office Action dated Jan. 29, 2016.
U.S. Appl. No. 14/021,777 Non-Final Office Action dated Sep. 16, 2015.
U.S. Appl. No. 14/021,777 Notice of Allowance dated Apr. 25, 2016.
U.S. Appl. No. 14/021,777 Restriction Requirement dated Apr. 14, 2015.
U.S. Appl. No. 14/124,620 Final Office Action dated Sep. 22, 2016.
U.S. Appl. No. 14/124,620 Non/Final Office Action dated Jan. 19, 2018.
U.S. Appl. No. 14/124,620 Non-Final Office Action dated Feb. 24, 2016.
U.S. Appl. No. 14/124,620 Non-Final Office Action dated May 23, 2018.
U.S. Appl. No. 14/124,620 Restriction Requirement dated Sep. 23, 2015.
U.S. Appl. No. 14/427,290 Final Office Action dated Feb. 2, 2017.
U.S. Appl. No. 14/656,596 Non/Final Office Action dated Feb. 1, 2018.
U.S. Appl. No. 14/656,596 Non-Final Office Action dated Aug. 2017.
U.S. Appl. No. 14/656,596 Restriction Requirement dated Feb. 14, 2017.
U.S. Appl. No. 14/656,596 Restriction Requirement dated May 11, 2017.
U.S. Appl. No. 14/656,619 Final Office Action dated Jun. 13, 2017.
U.S. Appl. No. 14/656,619 Non-Final Office Action dated Dec. 28, 2016.
U.S. Appl. No. 14/656,619 Notice of Allowance dated Feb. 27, 2018.
U.S. Appl. No. 14/656,619 Notice of Allowance dated Nov. 2, 2017.
U.S. Appl. No. 14/656,619 Restriction Requirement dated Aug. 11, 2016.
U.S. Appl. No. 15/125,270 Non-Final Office Action dated Apr. 27, 2018.
U.S. Appl. No. 15/125,570 Non-Final Office Action dated Apr. 27, 2018.
U.S. Appl. No. 15/125,570 Requirement for Restriction/Election dated Dec. 7, 2017.
U.S. Appl. No. 15/222,484 Non-Final Office Action dated Apr. 27, 2018.
U.S. Appl. No. 15/222,848 Requirement for Restriction/Election dated Nov. 16, 2017.
U.S. Appl. No. 15/222,849 Non-Final Office Action dated May 4, 2018.
U.S. Appl. No. 15/222,849 Requirement for Restriction/Election dated Nov. 16, 2017.
U.S. Appl. No. 15/268,178 Non-Final Office Action dated Apr. 27, 2018.
U.S. Appl. No. 15/268,178 Requirement for Restriction/Election dated Dec. 7, 2017.
U.S. Appl. No. 15/268,295 Restriction Requirement dated Mar. 12, 2018.
Vajdos, et al., "Comprehensive functinal Maps of the Antigen-binding Site of an Anti-ErbB2 Antibody Obtained with Shotgun Scanning Mutagenesis," *J. Mol. Biol.*, 320, 415-428, (2002).
Van Regenmortel, "Mapping Epitope Structure and Activity: From One-Dimensional Prediction to Four-Dimensional Description of Antigenic Specificity," *METHODS: A Comparison to Methods in Enzymology*, 9(3), 465-472, (1996).

Vaninio, et al., "HEMCAM, an adhesion molecule expressed by c-kit+ hemopoietic progenitors," *J Cell Biol*, 135(6 Pt 1):1655-1668, (Dec. 1996).
Wang, et al., "A novel 'pipeline' system for downstream preparation of therapeutic monoclonal antibodies", *Biotechmol Lett*, 35:1411-1419, (2013).
Wang, et al., "CD146, a multi-functional molecule beyond adhesion," *Cancer Lett*, 330(2):15-162, (Apr. 28, 2013).
Wang, et al., "Identification of CD146 expression, angiogenesis, and lymphangiogenesis as progression, metastasis and poor-prognosis related markers for gallbladder adenocarcinoma," *Tumor biol.*, 33:173-182 (2012).
Waston-Hurst, et al., "The role of N-cadherin, MCAM and beta3 integrin in melanoma progression, proliferation, migration and invasion," *Cancer Biol Ther*, 5(10):1375-1382, (Oct. 2006).
Wellbrock, et al., "CD146: a new partner for VEGFR2," *Blood*, 13;120(11):2164-2165, (Sep. 2012).
Weninger, et al., "Keratinocytes express the CD146 (Muc18/S-endo) antigen in tissue culture and during inflammatory skin diseases," *J Invest Dermatol*, 115(2):219-224, (Aug. 2000).
Witze, et al., "Wnt5a control of cellpolarity and directional movement by polarized redistribution of adhesion receptors," *Science*, 320(5874):365-369, (Apr. 2008).
Wong, et al., "The role of immunoglobulin superfamily cell adhesion molecules in cancer metastasis," *Int J Cell Biol*, ;2012:340296, (2012).
Wouters, et al., "Blau Syndrome, the prototypic auto-inflammatory granulomatous disease," *Pediatric Rheumotology*, 12:33 (2014).
Wu, et al., "Ectopical expression of human MUC18 increases metastasis of human prostate cancer cells," *Gene*, 327(2):201-213. (Mar. 2004).
Wu, et al., "Endothelial basement membrane laminin alpha5 selectively inhibits T lymphocyte extravasation into the brain," *Nat Med*, 15(5):519-27. (May 2009).
Wu, et al., "Enforced expression of MCAM/MUC18 increases invitro motility and invasiveness and in vivo metastasis of two mouse melanoma K1735 sublines in a syngeneic mouse model," *Mol Cancer Res*, 6(11):1666-1677 (Nov. 2008).
Wu, et al., "Enforced expression of METCAM/MUC18 increases tumorigenesis of human prostate cancer LNCaP cells in nude mice," *J Urol*, 185(4):1504-1512, (Apr. 2011).
Wu, et al., "Expression of a human cell adhesion molecule, MUC18, in prostate cancer cell lines and tissues," *Prostate*, 48(4):305-315 (Sep. 2001).
Wu, et al., "MCAM is a novel metastasis marker and regulates spreading, apoptosis and invasion of ovarian cancer cells," *Tumour Biol*, 33(5):1619-1628, (Oct. 2012).
Wu, et al., "Relationship of CD146 expression to secretion of interleukin (IL)-17, IL-22 and interferon-γ by CD4+ T cells in patients with inflammatory arthritis," *Clin Exp Immunol.*, 179(3):378-391, (2015).
Xie, et al., "Expression of MCAM/MUC18 by human melanoma cells leads to increased tumor growth and metastasis," *Cancer Res*, 1;57(11):2295-2303, (Jun. 1997).
Yamashita, et al., "Cryptic fragment α4 LEG4-5 derived from laminin α4 chain inhibits de novo adipogenesis by modulating the effect of fibroblast growth factor-2", Develop. Growth Differ. 50:97-107 (2008).
Yan, et al., "A novel anti-CD146 monoclonal antibody, AA98, inhibits angiogenesis and tumor growth," *Blood*, 1;102(1):184-191, (Jul. 2003).
Yang, et al., "Isolation and characterization of mouse MUC18 cDNA gene, and correlation of MUC18 expression in mouse melanoma cell lines with metastatic ability," *Gen*, 265(1-2):133-45, (Mar. 2001).
Yousif, et al., "Laminin isoforms in endothelial and perivascular basement membranes," *Cell Adh Migr*, 7(1):101-110, (Jan.-Feb. 2013).
Yun et al: "A Novel Antibody AA98 $V_H$/L Directed Against CD146 Efficiently Inhibits Angiogenesis", Anticancer Research, 27(6B):4219-4224, (2007).

(56) References Cited

OTHER PUBLICATIONS

Zabouo, et al., "CD146 expression is associated with a poor prognosis in human breast tumors and with enhanced motility in breast cancer cell lines," *Breast Cancer Res*, 11(1):R1, (2009).
Zeng, et al., "CD146, an epithelial-mesenchymal transition inducer, is associated with triple-negative breast cancer," *Proc Natl Acad Sci U S A*, 24;109(4):1127-1132, (Jan. 2012).
Zeng, et al., "Up-regulation of METCAM/MUC18 promotes motility, invasion, and tumorigenesis of human breast cancer cells," *BMC Cancer*, 30;11:113, (Mar. 2011).
Zhang, et al., "CD146 is a potential marker for the diagnosis of malignancy in cervical and endometrial cancer," *Oncol Lett*, 5(4):1189-1194, (Apr. 2013).
Zhang, et al., "Elevated Levels of soluble and Neurtrophil CD 146 in Active Systemic Vasculitis," *Science*, vol. 40, No. 6, pp. 351-356, (Jun. 2009).
Zhang, et al., "Generation and characterization of a panel of monoclonal antibodies against distinct epitopes of human CD146," *Hybridoma (Larchmt)*, 27(5):345-52, (Oct. 2008).
Zheng, et al., "Endothelial CD146 is required for in vitro tumor-induced angiogenesis: The role of a disulfide bond in signaling and dimerization," *The International Journal of Biochemistry & Cell Biology*, 41:2163-2172 (2009).
Zigler, et al., "Expression of Id-1 is regulated by MCAM/MUC18: a missing link in melanoma progression," *Cancer Res*, 15;71(10):3494-3504 (May 2011).
Zigler, et al., "Tumor immunotherapy in melanoma: strategies for overcoming mechanisms of resistance and escape," *Am J Clin Dermatol*, 9(5):307-311, (2008).
U.S. Appl. No. 15/125,568 Restriction Requirement dated Sep. 21, 2018.
U.S. Appl. No. 15/125,570 Final Office Action dated Sep. 24, 2018.
U.S. Appl. No. 15/222,849 Final Office Action dated Sep. 24, 2018.
PCT/IB2017/051402 International Preliminary Report on Patentability dated Sep. 20, 2018.
PCT/IB2017/051400 International Preliminary Report on Patentability dated Sep. 20, 2018.
Dajur, et al., "Secretion of interleukin-17 by CD8+ T cells expressing CD146 (MCAM)," *Clinical Immunology*, 152, 36-47, (2014).
Mayer, et al., "Sarcoidosis and Chronic Beryllium Disease: Similarities and Differences," *Semin Respir Crit Care Med*, 35:316-329, (2014).
Li, et al., "D38. Flying: Reaching New Heights in Sarconidosis," *American Journal of Respiratory and Critical Care Medicine*, 191, A5822, (2015).
PCT/US2013/058773 International Preliminary Report on Patentability dated Mar. 10, 2015.
U.S. Appl. No. 14/124,620 Final Office Action dated Oct. 16, 2018.
U.S. Appl. No. 14/124,620 Advisory Action dated Jan. 25, 2019.
U.S. Appl. No. 15/125,570 Advisory Action dated Jan. 31, 2019.
U.S. Appl. No. 15/222,848 Final Office Action dated Oct. 26, 2018.
U.S. Appl. No. 15/726,170 Non-Final Office Action dated Jan. 15, 2019.
U.S. Appl. No. 15/125,568 Non-Final Office Action dated Mar. 14, 2019.
Colman, "Effects of amino acid sequence changes on antibody-antigen interactions," Research in Immunology, 145:33-36, (1994).
Harding, et al., "The immunogenicity of humanized and fully human antibodies," mAbs, vol. 2, Issue 3, 256-265, (2010).
Chen, et al., "Enhancement and destruction of antibody function by somatic mutation: unequal occurrence is controlled by V gene combinatorial associations," The EMBO Journal, vol. 14, No. 12, pp. 2784-2794, (1995).
Kussie, et al., "A Single Engineered Amino Acid Substitution Changes Antibody Fine Specificity," Journal of Immunology, pp. 146-152, (1994).
Rudidof, et al., "Single amino acid substitution altering antigen-binding specificity," PNAS, 79: 1979-1983, (1982).
Steinman, "The discovery of natalizumab, a potent therapeutic for multiple sclerosis," J. Cell Rid., 199(3):413-416, (2012).

U.S. Appl. No. 14/124,620 Final Office Action dated May 22, 2019.
U.S. Appl. No. 15/222,848 Notice of Allowance dated Apr. 16, 2019.
U.S. Appl. No. 15/726,170 Final Office Action dated May 17, 2019.
U.S. Appl. No. 15/918,937 Requirement for Restriction/Election dated Jun. 14, 2019.
U.S. Appl. No. 15/125,570 Notice of Allowance dated Apr. 16, 2019.
EP 198155167.0 Extended European Search Report dated Jun. 21, 2019.
PCT/US2018/035894 International Search Report and Written Opinion dated Oct. 17, 2018.
U.S. Appl. No. 15/125,568 Non-Final Office Action dated Aug. 30, 2019.
Mayo Clinic, Multiple Sclerosis—Diagnosis, Treatment, mayoclinic.org/diseases-conditions/multiple-sclerosis/diagnosis-treament/drc-20350274?p=1, downloaded Aug. 26, 2019.
Mayo Clinic, Multiple Sclerosis—Overview, Symptoms, Disease Course, Causes, Risk Factors, Complications, mayoclinic.org/diseases-conditions/multiple-sclerosis/symptoms-causes/syc-20350269?p=1, downloaded Aug. 26, 2019.
Bachmeier et al., "Characterization and use of human brain microvascular endothelial cells to examine β-amyloid exchange in the blood-brain barrier," Cytotechnology, 62:519-529, (2010).
U.S. Appl. No. 15/726,170 Notice of Allowance dated Oct. 9, 2019.
U.S. Appl. No. 15/991,998 Non-Final Office Action dated Aug. 20, 2019.
U.S. Appl. No. 15/991,998 Notice of Allowance dated Jan. 10, 2020.
U.S. Appl. No. 15/125,568 Final Office Action dated Apr. 9, 2020.
PCT/US2018/035894 International Preliminary Report on Patentability dated Dec. 12, 2019.
U.S. Appl. No. 16/520,203 Restriction Requirement dated Jun. 29, 2020.
U.S. Appl. No. 15/222,848, filed Jul. 28, 2016; now issued as U.S. Pat. No. 10,407,507 on Sep. 10, 2019.
U.S. Appl. No. 15/222,849, filed Jul. 28, 2016; now issued as U.S. Pat. No. 10,414,825 on Sep. 17, 2019.
U.S. Appl. No. 14/021,777, filed Jun. 10, 2013; now issued as U.S. Pat. No. 9,447,190 on Sep. 20, 2016.
U.S. Appl. No. 15/726,170, filed Oct. 5, 2017; now issued as U.S. Pat. No. 10,584,177 on Mar. 10, 2020.
U.S. Appl. No. 14/656,619, filed Mar. 12, 2015; now issued as U.S. Pat. No. 10,059,761 on Aug. 28, 2018.
U.S. Appl. No. 15/125,570, filed Sep. 12, 2016, now issued as U.S. Pat. No. 10,407,506 on Sep. 10, 2019.
U.S. Appl. No. 15/991,998, filed May 29, 2018, now issued as U.S. Pat. No. 10,654,920 on May 19, 2020.
U.S. Appl. No. 16/520,203, filed Jul. 23, 2019.
U.S. Appl. No. 16/745,178, filed Jan. 16, 2020.
U.S. Appl. No. 16/691,525, filed Nov. 21, 2019.
U.S. Appl. No. 15/125,568, filed Sep. 12, 2016.
PCT/US2012/000274 filed Jun. 6, 2012.
U.S. Appl. No. 61/527,481, filed Aug. 25, 2011.
U.S. Appl. No. 61/493,780, filed Jun. 6, 2011.
PCT/US2013/058773 filed Sep. 9, 2013.
U.S. Appl. No. 61/698,916, filed Sep. 10, 2012.
U.S. Appl. No. 61/797,179, filed Nov. 30, 2012.
U.S. Appl. No. 61/797,356, filed Dec. 5, 2012.
U.S. Appl. No. 14/427,290, filed Mar. 10, 2015.
PCT/IB2015/051789 filed Mar. 12, 2015.
U.S. Appl. No. 61/952,129, filed Mar. 12, 2014.
U.S. Appl. No. 62/023,753, filed Jul. 11, 2014.
U.S. Appl. No. 62/068,286, filed Oct. 24, 2014.
U.S. Appl. No. 62/086,600, filed Dec. 2, 2014.
PCT/IB2015/051790 filed Mar. 12, 2015.
U.S. Appl. No. 61/952,132, filed Mar. 12, 2014.
U.S. Appl. No. 62/023,760, filed Jul. 11, 2014.
U.S. Appl. No. 62/068,349, filed Oct. 24, 2014.
U.S. Appl. No. 14/656,501, filed Mar. 12, 2015.
PCT/IB2015/051786 filed Mar. 12, 2015.
U.S. Appl. No. 61/952,123, filed Mar. 12, 2014.
U.S. Appl. No. 62/023,698, filed Jul. 11, 2014.
U.S. Appl. No. 62/068,438, filed Oct. 24, 2014.

(56) References Cited

OTHER PUBLICATIONS

PCT/IB2015/051787 filed Mar. 12, 2105.
U.S. Appl. No. 61/952,116, filed Mar. 12, 2014.
U.S. Appl. No. 61/952,833, filed Mar. 13, 2014.
U.S. Appl. No. 62/023,724, filed Jul. 11, 2014.
U.S. Appl. No. 62/068,419, filed Oct. 24, 2014.
PCT/IB2016/055559 filed Sep. 16, 2016.
U.S. Appl. No. 62/219,599, filed Sep. 16, 2015.
PCT/IB2016/055557 filed Sep. 16, 2016.
U.S. Appl. No. 62/219,611, filed Sep. 16, 2015.
U.S. Appl. No. 62/303,360, filed Mar. 3, 2016.
U.S. Appl. No. 62/303,369, filed Mar. 3, 2016.
U.S. Appl. No. 62/306,060, filed Mar. 9, 2016.
U.S. Appl. No. 62/345,732, filed Jun. 3, 2016.
U.S. Appl. No. 14/656,596, filed Mar. 12, 2015.
U.S. Appl. No. 15/268,178, filed Sep. 12, 2016.
U.S. Appl. No. 15/268,295, filed Sep. 12, 2016.
PCT/IB2017/051264 filed Mar. 3, 2017.
PCT/IB2017/051402 filed Mar. 9, 2017.
PCT/IB2017/053289 filed Jun. 2, 2017.
PCT/IB2017/051400 filed Mar. 9, 2017.
U.S. Appl. No. 62/306,061, filed Mar. 9, 2016.
U.S. Appl. No. 62/514,656, filed Jun. 2, 2017.
PCT/US2018/035894 filed Jun. 4, 2018.
U.S. Appl. No. 61/952,835, filed Mar. 13, 2014.
U.S. Appl. No. 62/023,577, filed Jul. 11, 2014.
PCT/IB2015/051785 filed Mar. 12, 2015.
U.S. Appl. No. 15/125,569, filed Sep. 12, 2016.
U.S. Appl. No. 14/124,620, filed Dec. 6, 2013.

\* cited by examiner

FIGURE 12A

Humanized 15F7 Vh Regions

| Chothia # | Kabat # | Linear # | Kabat FR or CDR | Murine 15F7 (SEQ ID NO:16) | Hu VH Acceptor FR (SEQ ID NO:96) Acc#ACF36857.1 | Hu VH Acceptor FR (SEQ ID NO:97) Acc#BAC01530.1 | 15F7 H1 (SEQ ID NO:57) | 15F7 H2 (SEQ ID NO:58) |
|---|---|---|---|---|---|---|---|---|
| 1 | 1 | 1 | Fr1 | Q | Q | Q | E | E |
| 2 | 2 | 2 | Fr1 | V | V | V | V | V |
| 3 | 3 | 3 | Fr1 | Q | Q | Q | Q | Q |
| 4 | 4 | 4 | Fr1 | L | L | L | L | L |
| 5 | 5 | 5 | Fr1 | Q | V | Q | Q | Q |
| 6 | 6 | 6 | Fr1 | Q | Q | Q | Q | Q |
| 7 | 7 | 7 | Fr1 | S | S | S | S | S |
| 8 | 8 | 8 | Fr1 | G | G | G | G | G |
| 9 | 9 | 9 | Fr1 | T | T | A | A | A |
| 10 | 10 | 10 | Fr1 | E | E | E | E | E |
| 11 | 11 | 11 | Fr1 | L | V | V | V | V |
| 12 | 12 | 12 | Fr1 | A | K | K | K | K |
| 13 | 13 | 13 | Fr1 | R | K | K | K | K |
| 14 | 14 | 14 | Fr1 | P | P | P | P | P |
| 15 | 15 | 15 | Fr1 | G | G | G | G | G |
| 16 | 16 | 16 | Fr1 | A | S | S | S | S |
| 17 | 17 | 17 | Fr1 | A | S | S | S | S |
| 18 | 18 | 18 | Fr1 | V | V | V | V | V |
| 19 | 19 | 19 | Fr1 | K | K | K | K | K |
| 20 | 20 | 20 | Fr1 | L | V | V | L | L |
| 21 | 21 | 21 | Fr1 | S | S | S | S | S |
| 22 | 22 | 22 | Fr1 | C | C | C | C | C |
| 23 | 23 | 23 | Fr1 | K | K | K | K | K |
| 24 | 24 | 24 | Fr1 | A | A | A | A | A |
| 25 | 25 | 25 | Fr1 | S | S | S | S | S |
| 26 | 26 | 26 | Fr1 | G | G | G | G | G |
| 27 | 27 | 27 | Fr1 | Y | G | G | Y | Y |
| 28 | 28 | 28 | Fr1 | T | T | T | T | T |
| 29 | 29 | 29 | Fr1 | F | F | F | F | F |
| 30 | 30 | 30 | Fr1 | T | S | S | T | T |
| 31 | 31 | 31 | CDR-H1 | S | S | S | S | S |

FIGURE 12B

Humanized 15F7 Vh Regions

| Chothia # | Kabat # | Linear # | Kabat FR or CDR | Murine 15F7 (SEQ ID NO:16) | Hu VH Acceptor FR (SEQ ID NO:96) | Hu VH Acceptor FR (SEQ ID NO:97) | 15F7 H1 (SEQ ID NO:57) | 15F7 H2 (SEQ ID NO:58) |
|---|---|---|---|---|---|---|---|---|
| 32 | 32 | 32 | CDR-H1 | Y | Y | Y | Y | Y |
| 33 | 33 | 33 | CDR-H1 | G | A | A | G | G |
| 34 | 34 | 34 | CDR-H1 | L | I | I | L | L |
| 35 | 35 | 35 | CDR-H1 | S | S | S | S | S |
| 36 | 36 | 36 | Fr2 | W | W | W | W | W |
| 37 | 37 | 37 | Fr2 | V | V | V | V | V |
| 38 | 38 | 38 | Fr2 | K | R | R | K | K |
| 39 | 39 | 39 | Fr2 | Q | Q | Q | Q | Q |
| 40 | 40 | 40 | Fr2 | R | A | A | R | R |
| 41 | 41 | 41 | Fr2 | A | P | P | A | P |
| 42 | 42 | 42 | Fr2 | G | G | G | G | G |
| 43 | 43 | 43 | Fr2 | Q | Q | Q | Q | Q |
| 44 | 44 | 44 | Fr2 | G | G | G | G | G |
| 45 | 45 | 45 | Fr2 | L | L | L | L | L |
| 46 | 46 | 46 | Fr2 | E | E | E | E | E |
| 47 | 47 | 47 | Fr2 | W | W | W | W | W |
| 48 | 48 | 48 | Fr2 | I | M | M | I | I |
| 49 | 49 | 49 | Fr2 | G | G | G | G | G |
| 50 | 50 | 50 | CDR-H2 | E | R | R | E | E |
| 51 | 51 | 51 | CDR-H2 | I | I | I | I | I |
| 52 | 52 | 52 | CDR-H2 | F | I | I | F | F |
| 52A | 52A | 53 | CDR-H2 | P | P | P | P | P |
| 53 | 53 | 54 | CDR-H2 | R | I | I | R | R |
| 54 | 54 | 55 | CDR-H2 | S | V | L | S | S |
| 55 | 55 | 56 | CDR-H2 | G | G | G | G | G |
| 56 | 56 | 57 | CDR-H2 | N | I | I | N | N |
| 57 | 57 | 58 | CDR-H2 | T | G | A | T | T |
| 58 | 58 | 59 | CDR-H2 | Y | N | N | Y | Y |
| 59 | 59 | 60 | CDR-H2 | Y | Y | Y | Y | Y |
| 60 | 60 | 61 | CDR-H2 | N | A | A | N | N |
| 61 | 61 | 62 | CDR-H2 | E | Q | Q | E | E |
| 62 | 62 | 63 | CDR-H2 | K | K | K | K | K |
| 63 | 63 | 64 | CDR-H2 | F | F | F | F | F |

FIGURE 12C

Humanized 15F7 Vh Regions

| Chothia # | Kabat # | Linear # | Kabat FR or CDR | Murine 15F7 (SEQ ID NO:16) | Hu VH Acceptor FR (SEQ ID NO:96) | Hu VH Acceptor FR (SEQ ID NO:97) | 15F7 H1 (SEQ ID NO:57) | 15F7 H2 (SEQ ID NO:58) |
|---|---|---|---|---|---|---|---|---|
| 64 | 64 | 65 | CDR-H2 | K | Q | Q | K | K |
| 65 | 65 | 66 | CDR-H2 | G | G | G | G | G |
| 66 | 66 | 67 | Fr3 | K | R | R | K | K |
| 67 | 67 | 68 | Fr3 | A | V | V | A | A |
| 68 | 68 | 69 | Fr3 | T | T | T | T | T |
| 69 | 69 | 70 | Fr3 | L | I | I | L | I |
| 70 | 70 | 71 | Fr3 | T | T | T | T | T |
| 71 | 71 | 72 | Fr3 | A | A | A | A | A |
| 72 | 72 | 73 | Fr3 | D | D | D | D | D |
| 73 | 73 | 74 | Fr3 | K | K | K | K | K |
| 74 | 74 | 75 | Fr3 | S | S | S | S | S |
| 75 | 75 | 76 | Fr3 | S | T | T | S | S |
| 76 | 76 | 77 | Fr3 | S | S | S | S | S |
| 77 | 77 | 78 | Fr3 | T | T | T | T | T |
| 78 | 78 | 79 | Fr3 | A | A | A | A | A |
| 79 | 79 | 80 | Fr3 | Y | Y | Y | Y | Y |
| 80 | 80 | 81 | Fr3 | M | M | M | M | M |
| 81 | 81 | 82 | Fr3 | E | E | E | E | E |
| 82 | 82 | 83 | Fr3 | L | L | L | L | L |
| 82A | 82A | 84 | Fr3 | R | S | S | R | R |
| 82B | 82B | 85 | Fr3 | S | S | S | S | S |
| 82C | 82C | 86 | Fr3 | L | L | L | L | L |
| 83 | 83 | 87 | Fr3 | T | R | R | R | R |
| 84 | 84 | 88 | Fr3 | S | S | S | S | S |
| 85 | 85 | 89 | Fr3 | E | E | E | E | E |
| 86 | 86 | 90 | Fr3 | D | D | D | D | D |
| 87 | 87 | 91 | Fr3 | S | T | T | T | T |
| 88 | 88 | 92 | Fr3 | A | A | A | A | A |
| 89 | 89 | 93 | Fr3 | V | V | V | V | V |
| 90 | 90 | 94 | Fr3 | Y | Y | Y | Y | Y |
| 91 | 91 | 95 | Fr3 | F | Y | Y | F | F |
| 92 | 92 | 96 | Fr3 | C | C | C | C | C |
| 93 | 93 | 97 | Fr3 | A | A | A | A | A |

FIGURE 12D

Humanized 15F7 Vh Regions

| Chothia # | Kabat # | Linear # | Kabat FR or CDR | Murine 15F7 (SEQ ID NO:16) | Hu VH Acceptor FR (SEQ ID NO:96) | Hu VH Acceptor FR (SEQ ID NO:97) | 15F7 H1 (SEQ ID NO:57) | 15F7 H2 (SEQ ID NO:58) |
|---|---|---|---|---|---|---|---|---|
| 94 | 94 | 98 | Fr3 | R | R | R | R | R |
| 95 | 95 | 99 | CDR-H3 | G | A | D | G | G |
| 96 | 96 | 100 | CDR-H3 | V | V | T | V | V |
| 97 | 97 | 101 | CDR-H3 | R | D | H | R | R |
| 98 | 98 | 102 | CDR-H3 | S | F | S | S | S |
| 99 | 99 | 103 | CDR-H3 | P | D | W | P | P |
| 100 | 100 | 104 | CDR-H3 | G | S | F | G | G |
| 100A | 100A | 105 | CDR-H3 | A | S | A | A | A |
| 100B | 100B | 106 | CDR-H3 | M | S | F | M | M |
|  |  |  |  |  | S |  |  |  |
|  |  |  |  |  | Y |  |  |  |
| 101 | 101 | 107 | CDR-H3 | D | S | D | D | D |
| 102 | 102 | 108 | CDR-H3 | Y | F | I | Y | Y |
| 103 | 103 | 109 | Fr4 | W | W | W | W | W |
| 104 | 104 | 110 | Fr4 | G | G | G | G | G |
| 105 | 105 | 111 | Fr4 | Q | Q | Q | Q | Q |
| 106 | 106 | 112 | Fr4 | G | G | G | G | G |
| 107 | 107 | 113 | Fr4 | T | T | T | T | T |
| 108 | 108 | 114 | Fr4 | S | L | M | L | L |
| 109 | 109 | 115 | Fr4 | V | V | V | V | V |
| 110 | 110 | 116 | Fr4 | T | T | T | T | T |
| 111 | 111 | 117 | Fr4 | V | V | V | V | V |
| 112 | 112 | 118 | Fr4 | S | S | S | S | S |
| 113 | 113 | 119 | Fr4 | S | S | S | S | S |

FIGURE 13A

Humanized 15F7 Vk Regions

| Chothia # | Kabat # | Linear # | Kabat FR or CDR | Murine 15F7 VL (SEQ ID NO:17) | Hu Vk Acceptor Fr (SEQ ID NO:53) Acc# AAY33350.1 | Hu Vk Acceptor Fr (SEQ ID NO:98) Acc# BAC01583.1 | 15F7 L1 (SEQ ID NO:59) | 15F7 L2 (SEQ ID NO:60) |
|---|---|---|---|---|---|---|---|---|
| 1 | 1 | 1 | Fr1 | D | D | D | D | D |
| 2 | 2 | 2 | Fr1 | I | I | I | I | I |
| 3 | 3 | 3 | Fr1 | Q | Q | Q | Q | Q |
| 4 | 4 | 4 | Fr1 | M | M | M | M | M |
| 5 | 5 | 5 | Fr1 | T | T | T | T | T |
| 6 | 6 | 6 | Fr1 | Q | Q | Q | Q | Q |
| 7 | 7 | 7 | Fr1 | S | S | S | S | S |
| 8 | 8 | 8 | Fr1 | S | P | P | S | P |
| 9 | 9 | 9 | Fr1 | S | S | S | S | S |
| 10 | 10 | 10 | Fr1 | S | S | S | S | S |
| 11 | 11 | 11 | Fr1 | F | L | L | L | L |
| 12 | 12 | 12 | Fr1 | S | S | S | S | S |
| 13 | 13 | 13 | Fr1 | V | A | A | A | A |
| 14 | 14 | 14 | Fr1 | S | S | S | S | S |
| 15 | 15 | 15 | Fr1 | L | V | V | V | V |
| 16 | 16 | 16 | Fr1 | G | G | G | G | G |
| 17 | 17 | 17 | Fr1 | D | D | D | D | D |
| 18 | 18 | 18 | Fr1 | R | R | R | R | R |
| 19 | 19 | 19 | Fr1 | V | V | V | V | V |
| 20 | 20 | 20 | Fr1 | T | T | T | T | T |
| 21 | 21 | 21 | Fr1 | I | I | I | I | I |
| 22 | 22 | 22 | Fr1 | T | T | T | T | T |
| 23 | 23 | 23 | Fr1 | C | C | C | C | C |
| 24 | 24 | 24 | CDR-L1 | K | R | R | K | K |
| 25 | 25 | 25 | CDR-L1 | A | A | A | A | A |
| 26 | 26 | 26 | CDR-L1 | S | S | G | S | S |
| 27 | 27 | 27 | CDR-L1 | E | Q | Q | E | E |
| 28 | 28 | 28 | CDR-L1 | D | S | G | D | D |
| 29 | 29 | 29 | CDR-L1 | I | I | I | I | I |
| 30 | 30 | 30 | CDR-L1 | Y | S | S | Y | Y |
| 31 | 31 | 31 | CDR-L1 | N | S | N | N | N |

FIGURE 13B

Humanized 15F7 Vk Regions

| Chothia # | Kabat # | Linear # | Kabat FR or CDR | Murine 15F7 VL (SEQ ID NO:17) | Hu Vk Acceptor Fr (SEQ ID NO:53) Acc# AAY33350.1 | Hu Vk Acceptor Fr (SEQ ID NO:98) Acc# BAC01583.1 | 15F7 L1 (SEQ ID NO:59) | 15F7 L2 (SEQ ID NO:60) |
|---|---|---|---|---|---|---|---|---|
| 32 | 32 | 32 | CDR-L1 | R | Y | S | R | R |
| 33 | 33 | 33 | CDR-L1 | L | L | L | L | L |
| 34 | 34 | 34 | CDR-L1 | A | N | A | A | A |
| 35 | 35 | 35 | Fr2 | W | W | W | W | W |
| 36 | 36 | 36 | Fr2 | Y | Y | Y | Y | Y |
| 37 | 37 | 37 | Fr2 | Q | Q | Q | Q | Q |
| 38 | 38 | 38 | Fr2 | Q | Q | Q | Q | Q |
| 39 | 39 | 39 | Fr2 | K | K | K | K | K |
| 40 | 40 | 40 | Fr2 | P | P | P | P | P |
| 41 | 41 | 41 | Fr2 | G | G | G | G | G |
| 42 | 42 | 42 | Fr2 | N | K | K | N | N |
| 43 | 43 | 43 | Fr2 | A | A | A | A | A |
| 44 | 44 | 44 | Fr2 | P | P | P | P | P |
| 45 | 45 | 45 | Fr2 | R | K | K | R | K |
| 46 | 46 | 46 | Fr2 | L | L | L | L | L |
| 47 | 47 | 47 | Fr2 | L | L | L | L | L |
| 48 | 48 | 48 | Fr2 | I | I | L | I | I |
| 49 | 49 | 49 | Fr2 | S | Y | Y | S | S |
| 50 | 50 | 50 | CDR-L2 | G | A | A | G | G |
| 51 | 51 | 51 | CDR-L2 | A | A | A | A | A |
| 52 | 52 | 52 | CDR-L2 | T | S | S | T | T |
| 53 | 53 | 53 | CDR-L2 | S | S | R | S | S |
| 54 | 54 | 54 | CDR-L2 | L | L | L | L | L |
| 55 | 55 | 55 | CDR-L2 | E | Q | E | E | E |
| 56 | 56 | 56 | CDR-L2 | T | S | S | T | T |
| 57 | 57 | 57 | Fr3 | G | G | G | G | G |
| 58 | 58 | 58 | Fr3 | V | V | V | V | V |
| 59 | 59 | 59 | Fr3 | P | P | P | P | P |
| 60 | 60 | 60 | Fr3 | S | S | S | S | S |
| 61 | 61 | 61 | Fr3 | R | R | R | R | R |
| 62 | 62 | 62 | Fr3 | F | F | F | F | F |

FIGURE 13C

Humanized 15F7 Vk Regions

| Chothia # | Kabat # | Linear # | Kabat FR or CDR | Murine 15F7 VL (SEQ ID NO:17) | Hu Vk Acceptor Fr (SEQ ID NO:53) Acc# AAY33350.1 | Hu Vk Acceptor Fr (SEQ ID NO:98) Acc# BAC01583.1 | 15F7 L1 (SEQ ID NO:59) | 15F7 L2 (SEQ ID NO:60) |
|---|---|---|---|---|---|---|---|---|
| 63 | 63 | 63 | Fr3 | S | S | S | S | S |
| 64 | 64 | 64 | Fr3 | G | G | G | G | G |
| 65 | 65 | 65 | Fr3 | S | S | S | S | S |
| 66 | 66 | 66 | Fr3 | G | G | G | G | G |
| 67 | 67 | 67 | Fr3 | S | S | S | S | S |
| 68 | 68 | 68 | Fr3 | G | G | G | G | G |
| 69 | 69 | 69 | Fr3 | K | T | T | K | K |
| 70 | 70 | 70 | Fr3 | D | D | D | D | D |
| 71 | 71 | 71 | Fr3 | Y | F | Y | Y | F |
| 72 | 72 | 72 | Fr3 | T | T | T | T | T |
| 73 | 73 | 73 | Fr3 | L | L | L | L | L |
| 74 | 74 | 74 | Fr3 | S | T | T | T | T |
| 75 | 75 | 75 | Fr3 | I | I | I | I | I |
| 76 | 76 | 76 | Fr3 | T | S | S | S | S |
| 77 | 77 | 77 | Fr3 | S | S | S | S | S |
| 78 | 78 | 78 | Fr3 | L | L | L | L | L |
| 79 | 79 | 79 | Fr3 | Q | Q | Q | Q | Q |
| 80 | 80 | 80 | Fr3 | T | P | P | T | P |
| 81 | 81 | 81 | Fr3 | E | E | E | E | E |
| 82 | 82 | 82 | Fr3 | D | D | D | D | D |
| 83 | 83 | 83 | Fr3 | V | F | F | F | F |
| 84 | 84 | 84 | Fr3 | A | A | A | A | A |
| 85 | 85 | 85 | Fr3 | T | T | T | T | T |
| 86 | 86 | 86 | Fr3 | Y | Y | Y | Y | Y |
| 87 | 87 | 87 | Fr3 | Y | Y | Y | Y | Y |
| 88 | 88 | 88 | Fr3 | C | C | C | C | C |
| 89 | 89 | 89 | CDR-L3 | Q | Q | Q | Q | Q |
| 90 | 90 | 90 | CDR-L3 | Q | Q | Q | Q | Q |
| 91 | 91 | 91 | CDR-L3 | Y | S | Y | Y | Y |
| 92 | 92 | 92 | CDR-L3 | W | Y | Y | W | W |
| 93 | 93 | 93 | CDR-L3 | S | S | S | S | S |

FIGURE 13D

Humanized 15F7 Vk Regions

| Chothia # | Kabat # | Linear # | Kabat FR or CDR | Murine 15F7 VL (SEQ ID NO:17) | Hu Vk Acceptor Fr (SEQ ID NO:53) Acc# AAY33350.1 | Hu Vk Acceptor Fr (SEQ ID NO:98) Acc# BAC01583.1 | 15F7 L1 (SEQ ID NO:59) | 15F7 L2 (SEQ ID NO:60) |
|---|---|---|---|---|---|---|---|---|
| 94 | 94 | 94 | CDR-L3 | I | T | T | I | I |
| 95 | 95 | 95 | CDR-L3 | P | P | P | P | P |
| 96 | 96 | 96 | CDR-L3 | Y | L | Q | Y | Y |
| 97 | 97 | 97 | CDR-L3 | T | T | T | T | T |
| 98 | 98 | 98 | Fr4 | F | F | F | F | F |
| 99 | 99 | 99 | Fr4 | G | G | G | G | G |
| 100 | 100 | 100 | Fr4 | G | G | Q | G | G |
| 101 | 101 | 101 | Fr4 | G | G | G | G | G |
| 102 | 102 | 102 | Fr4 | T | T | T | T | T |
| 103 | 103 | 103 | Fr4 | N | K | K | K | K |
| 104 | 104 | 104 | Fr4 | L | L | L | L | V |
| 105 | 105 | 105 | Fr4 | E | E | E | E | E |
| 106 | 106 | 106 | Fr4 | I | I | I | I | I |
| 107 | 107 | 107 | Fr4 | K | K | K | K | K |
| 108 | 108 | 108 | Fr4 | R | R | R | R | R |

US 10,889,636 B2

ANTI-LAMININ4 ANTIBODIES SPECIFIC FOR LG4-5

CROSS REFERENCE TO RELATED APPLICATIONS

This application is a divisional of U.S. Ser. No. 14/656,619 filed Mar. 12, 2015, which claims the benefit of U.S. 61/952,132, filed Mar. 12, 2014, U.S. 62/023,760 filed Jul. 11, 2014, and U.S. 62/068,349 filed Oct. 24, 2014, each of which is incorporated herein by reference in its entirety for all purposes.

REFERENCE TO A SEQUENCE LISTING

The Sequence Listing written in file 510136SEQLST.txt is 144,516 bytes, was created on Mar. 12, 2018, and is hereby incorporated by reference.

BACKGROUND

Cancer is a major public health problem. One in four deaths in the United States is due to cancer, and the lifetime probability of being diagnosed with an invasive cancer is approximately 40%. Siegel et al., CA Cancer J. Clin. 62:10-29 (2012). An estimated 500,000 Americans die from cancer each year (Siegel et al., CA Cancer J. Clin. 62:10-29 (2012)). Lack of specificity of conventional chemotherapies and consequent side effects limit the delivery of drug dosages needed to eliminate the majority of cancer cells.

Laminin proteins containing the laminin α4 chain have been reported to be expressed in some types of cancer. Syndecans, which are reported binding partners of laminin α4, have also been reported to be expressed in some types of cancer.

SUMMARY OF THE CLAIMED INVENTION

The invention provides antibodies that specifically binds to an epitope within the LG4-5 modules of the G domain of laminin α4. Some antibodies do not inhibit binding of laminin α4 to MCAM. Some antibodies bind to an epitope within LG4. Some antibodies bind to an epitope within LG5. Some antibodies bind to an epitope to which both LG5 and LG4 contribute residues. Some antibodies inhibit binding of laminin α4 to a heparan sulfate proteoglycan, such as syndecan-1, -2, -3, -4, a glypican, a betaglycan, CD44, perlecan, agrin, or collagen XVIII.

Some of the above antibodies selectively binds to a biological sample comprising cancer cells, such as melanoma cells, when compared to a control sample, optionally wherein the control sample and the biological sample comprise cells of the same tissue origin and optionally wherein binding of the antibody to the biological sample is at least 2-fold or 5-fold greater than the binding of the antibody to the control sample.

Some of the above antibodies compete for binding to laminin α4 with antibody 15F7 characterized by a mature heavy chain variable region of SEQ ID NO:16 and mature light chain variable region of SEQ ID NO:17, or antibody 6C12 characterized by a mature heavy chain variable region of SEQ ID NO:26 and mature light chain variable region of SEQ ID NO:27, or antibody 13G10 characterized by a mature heavy chain variable region of SEQ ID NOS:36 or 37 and mature light chain variable region of SEQ ID NO:38. Some of the above antibodies compete for binding to laminin α4 with antibody 15F7 characterized by a mature heavy chain variable region of SEQ ID NO:16 and mature light chain variable region of SEQ ID NO:17, or antibody 6C12 characterized by a mature heavy chain variable region of SEQ ID NO:26 and mature light chain variable region of SEQ ID NO:27 or 94, or antibody 13G10 characterized by a mature heavy chain variable region of SEQ ID NOS:36 or 37 and mature light chain variable region of SEQ ID NO:38.

Some of the above antibodies binds to the same epitope on laminin α4 as 15F7, 6C12, or 13G10.

Some of the above antibodies comprising three light chain CDRs and three heavy chain CDRs, wherein each CDR has at least 90% sequence identity to a corresponding CDR from the heavy and light chain variable regions of 15F7 (SEQ ID NOS:16 and 17, respectively), 6C12 (SEQ ID NOS:26 and 27, respectively), or 13G10 (SEQ ID NOS:36/37 and 38, respectively). Some of the above antibodies comprising three light chain CDRs and three heavy chain CDRs, wherein each CDR has at least 90% sequence identity to a corresponding CDR from the heavy and light chain variable regions of 15F7 (SEQ ID NOS:16 and 17, respectively), 6C12 (SEQ ID NOS:26 and 27/94, respectively), or 13G10 (SEQ ID NOS:36/37 and 38, respectively).

Some of the above antibodies comprise three heavy chain CDRs and three light chain CDRs of 15F7, 6C12, or 13G10.

Some of the above antibodies are monoclonal. Some of the above antibodies are chimeric, humanized, veneered, or human. Some of the above antibodies have human IgG1 kappa isotype.

The invention further provides a humanized or chimeric 15F7 antibody that specifically binds to laminin α4, wherein 15F7 is a mouse antibody characterized by a mature heavy chain variable region of SEQ ID NO:16 and a mature light chain variable region of SEQ ID NO:17. Optionally the humanized antibody comprises a humanized heavy chain comprising three CDRs of the 15F7 heavy chain variable region (SEQ ID NO:16) and a humanized light chain comprising three CDRs of the 15F7 light chain variable region (SEQ ID NO:17). Optionally the humanized antibody comprises a humanized mature heavy chain variable region having an amino acid sequence at least 90% identical to SEQ ID NO:58 and a humanized mature light chain variable region having an amino acid sequence at least 90% identical to SEQ ID NO:59. Optionally, the humanized antibody comprises a humanized heavy chain comprising three CDRs of the 15F7 heavy chain variable region (SEQ ID NO:16) and a humanized light chain comprising three CDRs of the 15F7 light chain variable region (SEQ ID NO:17). Optionally, any differences in CDRs of the mature heavy chain variable region and mature light chain variable region from SEQ ID NOS:16 and 17, respectively reside in positions H60-H65. In some humanized antibodies at least one of positions L42, L49, and L69 is occupied by N, S, and K, respectively, and at least one of positions H1, H20, H27, H30, H38, H40, H48, H66, H67, H75, H82A, and H91 is occupied by E, L, Y, T, K, R, I, K, A, S, R, and F, respectively. In some humanized antibodies positions L42, L49, and L69 are occupied by N, S, and K, respectively, and H1, H20, H27, H30, H38, H40, H48, H66, H67, H75, H82A, and H91 are occupied by E, L, Y, T, K, R, I, K, A, S, R, and F, respectively. In some humanized antibodies at least one of positions L8, L45, and L80 is occupied by S, R, and T, respectively. In some humanized antibodies at least one of positions L8, L45, L80, and L104 is occupied by S, R, T, and V, respectively. In some humanized antibodies at least one of positions H41 and H69 is occupied by A and L, respectively. In some humanized antibodies positions L8, L45, and L80 are occupied by S, R, and T, respectively. In some humanized antibodies position L104 is occupied by V. In some humanized antibodies positions H41 and H69 are occupied by A and L, respectively. Some humanized antibodies comprise a mature heavy chain variable region having an amino acid sequence at least 95% identical to SEQ ID NO:58 and a mature light chain variable region having an amino acid sequence at least 95% identical to SEQ ID NO:59. In some humanized antibodies, the mature heavy chain variable region has an amino acid sequence of SEQ ID NO:57 and the mature light chain variable region has an amino acid sequence of SEQ ID NO:59. In some humanized antibodies, the mature heavy chain variable region has an amino acid sequence of SEQ ID NO:57 and the mature light chain variable region has an amino acid sequence of SEQ ID NO:60. In some humanized antibodies, the mature heavy chain variable region has an amino acid sequence of SEQ ID NO:58 and the mature light chain variable region has an amino acid sequence of SEQ ID NO:59. In some humanized antibodies, the mature heavy chain variable region has an amino acid sequence of SEQ ID NO:58 and the mature light chain variable region has an amino acid sequence of SEQ ID NO:60.

Any of the above described antibodies can be an intact antibody, a single-chain antibody, Fab, or Fab'2 fragment. In any of the antibodies, the mature light chain variable region can be fused to a light chain constant region and the mature heavy chain variable region can be fused to a heavy chain constant region. Optionally, the heavy chain constant region is a mutant form of a natural human heavy chain constant region which has reduced binding to a Fcγ receptor relative to the natural human heavy chain constant region. Optionally the heavy chain constant region is of IgG1 isotype. Optionally, the mature heavy chain variable region is fused to a heavy chain constant region having the sequence of SEQ ID NO:61 and/or the mature light chain variable region is fused to a light chain constant region having the sequence of SEQ ID NO:62. Optionally, the mature heavy chain variable region is fused to a heavy chain constant region having the sequence of SEQ ID NO:61, 89, or 101 and/or the mature light chain variable region is fused to a light chain constant region having the sequence of SEQ ID NO:62 or 90. Any of the above antibodies can be conjugated to a therapeutic or cytotoxic agent, such as saporin or a radioisotope.

The invention further provides pharmaceutical composition comprising any of the above antibodies and a pharmaceutically acceptable carrier.

The invention further provides a nucleic acid encoding the heavy and/or light chain(s) of any of the above described antibodies, such as any of SEQ ID NOS:63-64, 67-68, 71-73, and 77-80. The invention further provides a nucleic acid encoding the heavy and/or light chain(s) of any of the above described antibodies, such as any of SEQ ID NOS: 63-64, 67-68, 71-73, 77-80, 92-93, 99-100, or 102.

The invention further provides a recombinant expression vector comprising a nucleic acid as above described and a host cell transformed with such a recombinant expression vector.

The invention further provides a method of humanizing an antibody, the method comprising: (a) determining the sequences of the heavy and light chain variable regions of a mouse antibody; (b) synthesizing a nucleic acid encoding a humanized heavy chain comprising CDRs of the mouse antibody heavy chain and a nucleic acid encoding a humanized light chain comprising CDRs of the mouse antibody light chain; (c) expressing the nucleic acids in a host cell to produce a humanized antibody; wherein the mouse antibody is 15F7, 6C12, or 13G10.

The invention further provides a method of producing a humanized, chimeric, or veneered antibody, the method comprising: (a) culturing cells transformed with nucleic acids encoding the heavy and light chains of the antibody, so that the cells secrete the antibody; and (b) purifying the antibody from cell culture media; wherein the antibody is an antibody is a humanized, chimeric, or veneered form of 15F7, 6C12, or 13G10.

The invention further provides a method of producing a cell line producing a humanized, chimeric, or veneered antibody, the method comprising: (a) introducing a vector encoding heavy and light chains of an antibody and a selectable marker into cells; (b) propagating the cells under conditions to select for cells having increased copy number of the vector; (c) isolating single cells from the selected cells; and (d) banking cells cloned from a single cell selected based on yield of antibody; wherein the antibody is a humanized, chimeric, or veneered form of 15F7, 6C12, or 13G10. Optionally, the method further comprises propagating the cells under selective conditions and screening for cell lines naturally expressing and secreting at least 100 mg/L/$10^6$ cells/24 h.

The invention further provides a method of treating or effecting prophylaxis of a cancer in a patient having or at risk for the cancer, the method comprising administering to the patient an effective regime of any of the above described antibodies. In some methods, the patient has a cancer, and the cancer is melanoma, breast cancer, lung cancer, or colorectal cancer.

The invention further provides a method of inhibiting cell adhesion in a biological sample, the method comprising contacting the biological sample with an effective amount of any of the above described antibodies. In some methods, the cell adhesion is mediated by the LG4-5 modules of the G domain of laminin α4. In some methods, the biological sample comprises cancer cells.

The invention further provides a method for detecting the presence of a cancer, such as melanoma, in a biological sample, the method comprising: (a) contacting the biological sample with any of the above antibodies; (b) detecting binding of the antibody to the biological sample; (c) contacting a control sample with the antibody; (d) detecting binding of the antibody to the control sample; and (e) comparing binding of the antibody to the biological sample with binding of the antibody to the control sample, whereby increased binding of the antibody to the biological sample compared to the control sample indicates the presence of cancer in the biological sample. Optionally the control sample and the biological sample comprise cells of the same tissue origin. Optionally binding of the antibody to the biological sample is at least 2-fold or 5-fold greater than the binding of the antibody to the control sample.

The invention further provides a method of evaluating the efficacy of a therapeutic agent in a patient diagnosed with a cancer, the method comprising: (a) contacting a first biological sample from the patient, obtained prior to treatment with the therapeutic agent, with any of the above antibodies; (b) detecting binding of the antibody to the first biological sample; (c) contacting a second biological sample from the patient, obtained following treatment with the therapeutic agent, with the antibody; (d) detecting binding of the antibody to the second biological sample; (e) comparing binding of the antibody to the first biological sample with binding of the antibody to the second biological sample, whereby decreased binding of the antibody to the second biological sample compared to the first biological sample indicates that the therapeutic agent is effective in treating the cancer in the patient.

The invention further provides a method of inhibiting binding of laminin α4 to a heparan sulfate proteoglycan in a biological sample, the method comprising contacting the biological sample with any of the above antibodies. Optionally, the heparan sulfate proteoglycan is syndecan-1, -2, -3, or -4 or glypican, a betaglycan, CD44, perlecan, agrin, or collagen XVIII.

The invention further provides a method of treating or effecting prophylaxis of a disease in which the LG4-5 modules of the G domain of laminin α4 contribute to progression of the disease, the method comprising administering to a patient having or at risk of the disease an effective regime of any of the above antibodies. Optionally, the disease is a cancer, such as melanoma, breast cancer, lung cancer, or colorectal cancer. Optionally the LG4-5 modules of the G domain of laminin α4 contribute to progression of the disease by means of interaction with a heparan sulfate proteoglycan. Optionally, the heparan sulfate proteoglycan is syndecan-1, -2, -3, or -4. Optionally, the disease is psoriasis, sarcoidosis, multiple sclerosis, or psoriatic arthritis.

The invention further provides a method of treating or effecting prophylaxis of an autoimmune disease in a patient having or at risk for the autoimmune disease, the method comprising administering to the patient an effective regime of any of the above described antibodies. Optionally, the disease is diabetes, Crohn's disease, ulcerative colitis, multiple sclerosis, stiff man syndrome, rheumatoid arthritis, myasthenia gravis, systemic lupus erythematosus, celiac disease, psoriasis, psoriatic arthritis, sarcoidosis, ankylosing spondylitis, Sjogren's syndrome, or uveitis.

The invention further provides a method of inhibiting angiogenesis in a patient, the method comprising administering to a patient an effective regime of any of the above described antibodies. Optionally the patient has a cancer.

The invention further provides a method of treating or effecting prophylaxis of obesity or an obesity-related disease in a patient having or at risk for obesity or the obesity-related disease, the method comprising administering to the patient an effective regime of any of the above described antibodies. Optionally, the obesity-related disease is non-alcoholic steatohepatitis (NASH), Prader-Willi syndrome, craniopharyngioma, Bardet-Biedl syndrome, Cohen syndrome, or MOMO syndrome.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 11A shows the ratio for each individual sample, and FIG. 11B shows averages and standard errors for each group (n=3).

FIGS. 12A-D show exemplary humanized 15F7 Vh designs, with backmutations and other mutations based on selected human frameworks. The gray-shaded areas in the first column indicate the CDRs as defined by Chothia, and the gray-shaded areas in the remaining columns indicate the CDRs as defined by Kabat.

FIGS. 13A-D show exemplary humanized 15F7 Vk designs, with backmutations and other mutations based on selected human frameworks. The gray-shaded areas in the first column indicate the CDRs as defined by Chothia, and the gray-shaded areas in the remaining columns indicate the CDRs as defined by Kabat.

BRIEF DESCRIPTION OF THE SEQUENCES

Figure 1:
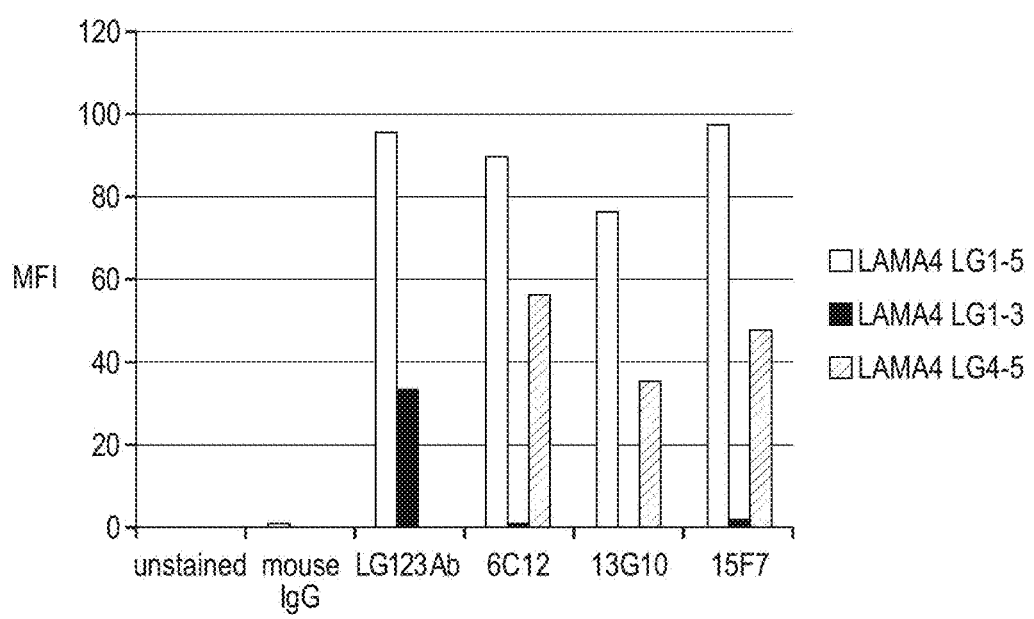
FIG. 1 shows binding as assessed by flow cytometry of a LG1-3-specific LAMA4 antibody and the 6C12, 13G10, and 15F7 antibodies to 293 cells displaying LAMA4 fragments containing LG1-5, LG1-3, and LG4-5.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO:1 sets forth the amino acid sequence of laminin α4 as provided by UniProt Number Q16363.

SEQ ID NO:2 sets forth the amino acid sequence of laminin α4 as provided by GenBank Accession Number NP001098676.

SEQ ID NO:3 sets forth the amino acid sequence of laminin α4 as provided by GenBank Accession Number NP001098677.

SEQ ID NO:4 sets forth the amino acid sequence of the G domain of laminin α4.

SEQ ID NO:5 sets forth the amino acid sequence of the LG1 module of the G domain of laminin α4.

SEQ ID NO:6 sets forth the amino acid sequence of the LG2 module of the G domain of laminin α4.

SEQ ID NO:7 sets forth the amino acid sequence of the LG3 module of the G domain of laminin α4.

SEQ ID NO:8 sets forth the amino acid sequence of the LG1-3 modules of the G domain of laminin α4.

SEQ ID NO:9 sets forth the amino acid sequence of the LG4 module of the G domain of laminin α4.

SEQ ID NO:10 sets forth the amino acid sequence of the LG5 module of the G domain of laminin α4.

SEQ ID NO:11 sets forth the amino acid sequence of the LG4-5 modules of the G domain of laminin α4.

SEQ ID NO:12 sets forth the amino acid sequence of syndecan-1 as provided by UniProt Number P18827.

SEQ ID NO:13 sets forth the amino acid sequence of syndecan-2 as provided by UniProt Number P34741.

SEQ ID NO:14 sets forth the amino acid sequence of syndecan-3 as provided by UniProt Number O75056.

SEQ ID NO:15 sets forth the amino acid sequence of syndecan-4 as provided by UniProt Number P31431.

SEQ ID NO:16 sets forth the amino acid sequence of mouse 15F7 mature heavy chain variable region.

SEQ ID NO:17 sets forth the amino acid sequence of mouse 15F7 mature light chain variable region.

SEQ ID NO:18 sets forth the amino acid sequence of the 15F7 heavy chain variable region signal peptide.

SEQ ID NO:19 sets forth the amino acid sequence of the 15F7 light chain variable region signal peptide.

SEQ ID NO:20 sets forth the amino acid sequence of CDR1, as defined by Kabat, of the mouse 15F7 heavy chain.

SEQ ID NO:21 sets forth the amino acid sequence of CDR2, as defined by Kabat, of the mouse 15F7 heavy chain.

SEQ ID NO:22 sets forth the amino acid sequence of CDR3, as defined by Kabat, of the mouse 15F7 heavy chain.

SEQ ID NO:23 sets forth the amino acid sequence of CDR1, as defined by Kabat, of the mouse 15F7 light chain.

SEQ ID NO:24 sets forth the amino acid sequence of CDR2, as defined by Kabat, of the mouse 15F7 light chain.

SEQ ID NO:25 sets forth the amino acid sequence of CDR3, as defined by Kabat, of the mouse 15F7 light chain.

SEQ ID NO:26 sets forth the amino acid sequence of mouse 6C12 mature heavy chain variable region.

SEQ ID NO:27 sets forth the amino acid sequence of mouse 6C12 mature light chain variable region, version 1.

SEQ ID NO:28 sets forth the amino acid sequence of the 6C12 heavy chain variable region signal peptide.

SEQ ID NO:29 sets forth the amino acid sequence of the 6C12 light chain variable region signal peptide.

SEQ ID NO:30 sets forth the amino acid sequence of CDR1, as defined by Kabat, of the mouse 6C12 heavy chain.

SEQ ID NO:31 sets forth the amino acid sequence of CDR2, as defined by Kabat, of the mouse 6C12 heavy chain.

SEQ ID NO:32 sets forth the amino acid sequence of CDR3, as defined by Kabat, of the mouse 6C12 heavy chain.

SEQ ID NO:33 sets forth the amino acid sequence of CDR1, as defined by Kabat, of the mouse 6C12 light chain, version 1.

SEQ ID NO:34 sets forth the amino acid sequence of CDR2, as defined by Kabat, of the mouse 6C12 light chain.

SEQ ID NO:35 sets forth the amino acid sequence of CDR3, as defined by Kabat, of the mouse 6C12 light chain.

SEQ ID NO:36 sets forth the amino acid sequence of mouse 13G10 mature heavy chain variable region, version 1.

SEQ ID NO:37 sets forth the amino acid sequence of mouse 13G10 mature heavy chain variable region, version 2.

SEQ ID NO:38 sets forth the amino acid sequence of mouse 13G10 mature light chain variable region.

SEQ ID NO:39 sets forth the amino acid sequence of the 13G10 heavy chain variable region signal peptide, version 1.

SEQ ID NO:40 sets forth the amino acid sequence of the 13G10 heavy chain variable region signal peptide, version 2.

SEQ ID NO:41 sets forth the amino acid sequence of the 13G10 light chain variable region signal peptide.

SEQ ID NO:42 sets forth the amino acid sequence of CDR1, as defined by Kabat, of the mouse 13G10 heavy chain, version 1.

SEQ ID NO:43 sets forth the amino acid sequence of CDR2, as defined by Kabat, of the mouse 13G10 heavy chain, version 1.

SEQ ID NO:44 sets forth the amino acid sequence of CDR3, as defined by Kabat, of the mouse 13G10 heavy chain, version 1.

SEQ ID NO:45 sets forth the amino acid sequence of CDR1, as defined by Kabat, of the mouse 13G10 heavy chain, version 2.

SEQ ID NO:46 sets forth the amino acid sequence of CDR2, as defined by Kabat, of the mouse 13G10 heavy chain, version 2.

SEQ ID NO:47 sets forth the amino acid sequence of CDR3, as defined by Kabat, of the mouse 13G10 heavy chain, version 2.

SEQ ID NO:48 sets forth the amino acid sequence of CDR1, as defined by Kabat, of the mouse 13G10 light chain.

SEQ ID NO:49 sets forth the amino acid sequence of CDR2, as defined by Kabat, of the mouse 13G10 light chain.

SEQ ID NO:50 sets forth the amino acid sequence of CDR3, as defined by Kabat, of the mouse 13G10 light chain.

SEQ ID NO:51 sets forth the amino acid sequence of a human VH acceptor FR as provided by NCBI Accession Code ACF36857.1, version 1.

SEQ ID NO:52 sets forth the amino acid sequence of a human VH acceptor FR as provided by NCBI Accession Code BAC01530.1, version 1.

SEQ ID NO:53 sets forth the amino acid sequence of a human VL acceptor FR as provided by NCBI Accession Code AAY33350.1.

SEQ ID NO:54 sets forth the amino acid sequence of a human VL acceptor FR as provided by NCBI Accession Code BAC01583.1, version 1.

SEQ ID NO:55 sets forth the amino acid sequence of humanized 15F7 heavy chain variable region with no back-mutations or other mutations.

SEQ ID NO:56 sets forth the amino acid sequence of humanized 15F7 light chain variable region with no back-mutations or other mutations.

SEQ ID NO:57 sets forth the amino acid sequence of humanized 15F7 heavy chain variable region version 1 (H1).

SEQ ID NO:58 sets forth the amino acid sequence of humanized 15F7 heavy chain variable region version 2 (H2).

SEQ ID NO:59 sets forth the amino acid sequence of humanized 15F7 light chain variable region version 1 (L1).

SEQ ID NO:60 sets forth the amino acid sequence of humanized 15F7 light chain variable region version 2 (L2).

SEQ ID NO:61 sets forth the amino acid sequence of an exemplary human IgG1 constant region.

SEQ ID NO:62 sets forth the amino acid sequence of an exemplary human kappa light chain constant region without a N-terminal arginine.

SEQ ID NO:63 sets forth the nucleic acid sequence of the murine 15F7 heavy chain variable region.

SEQ ID NO:64 sets forth the nucleic acid sequence of the murine 15F7 light chain variable region version.

SEQ ID NO:65 sets forth the nucleic acid sequence of the 15F7 heavy chain variable region signal peptide.

SEQ ID NO:66 sets forth the nucleic acid sequence of the 15F7 light chain variable region signal peptide.

SEQ ID NO:67 sets forth the nucleic acid sequence of the murine 6C12 heavy chain variable region.

SEQ ID NO:68 sets forth the nucleic acid sequence of the murine 6C12 light chain variable region, version 1.

SEQ ID NO:69 sets forth the nucleic acid sequence of the 6C12 heavy chain variable region signal peptide.

SEQ ID NO:70 sets forth the nucleic acid sequence of the 6C12 light chain variable region signal peptide.

SEQ ID NO:71 sets forth the nucleic acid sequence of the murine 13G10 heavy chain variable region, version 1.

SEQ ID NO:72 sets forth the nucleic acid sequence of the murine 13G10 heavy chain variable region, version 2.

SEQ ID NO:73 sets forth the nucleic acid sequence of the murine 13G10 light chain variable region.

SEQ ID NO:74 sets forth the nucleic acid sequence of the 13G10 heavy chain variable region signal peptide, version 1.

SEQ ID NO:75 sets forth the nucleic acid sequence of the 13G10 heavy chain variable region signal peptide, version 2.

SEQ ID NO:76 sets forth the nucleic acid sequence of the 13G10 light chain variable region signal peptide.

SEQ ID NO:77 sets forth the nucleic acid sequence of humanized 15F7 heavy chain variable region version 1 (H1).

SEQ ID NO:78 sets forth the nucleic acid sequence of humanized 15F7 heavy chain variable region version 2 (H2).

SEQ ID NO:79 sets forth the nucleic acid sequence of humanized 15F7 light chain variable region version 1 (L1), version 1.

SEQ ID NO:80 sets forth the nucleic acid sequence of humanized 15F7 light chain variable region version 2 (L2).

SEQ ID NO:81 sets forth the nucleic acid sequence of the G domain of laminin α4.

SEQ ID NO:82 sets forth the nucleic acid sequence of the LG1 module of the G domain of laminin α4.

SEQ ID NO:83 sets forth the nucleic acid sequence of the LG2 module of the G domain of laminin α4.

SEQ ID NO:84 sets forth the nucleic acid sequence of the LG3 module of the G domain of laminin α4.

SEQ ID NO:85 sets forth the nucleic acid sequence of the LG1-3 modules of the G domain of laminin α4.

SEQ ID NO:86 sets forth the nucleic acid sequence of the LG4 module of the G domain of laminin α4.

SEQ ID NO:87 sets forth the nucleic acid sequence of the LG5 module of the G domain of laminin α4.

SEQ ID NO:88 sets forth the nucleic acid sequence of the LG4-5 modules of the G domain of laminin α4.

SEQ ID NO:89 sets forth the amino acid sequence of an exemplary human IgG1 constant region of the IgG1 G1m3 allotype.

SEQ ID NO:90 sets forth the amino acid sequence of an exemplary human kappa light chain constant region with a N-terminal arginine.

SEQ ID NO:91 sets forth the amino acid sequence of an exemplary human IgG1 constant region without a C-terminal lysine.

SEQ ID NO:92 sets forth the nucleic acid sequence of an exemplary human IgG1 constant region of the IgG1 G1m3 allotype.

SEQ ID NO:93 sets forth the nucleic acid sequence of an exemplary human kappa light chain constant region with a N-terminal arginine.

SEQ ID NO:94 sets forth the amino acid sequence of mouse 6C12 mature light chain variable region, version 2.

SEQ ID NO:95 sets forth the amino acid sequence of CDR1, as defined by Kabat, of the mouse 6C12 light chain, version 2.

SEQ ID NO:96 sets forth the amino acid sequence of a human VH acceptor FR as provided by NCBI Accession Code ACF36857.1, version 2.

SEQ ID NO:97 sets forth the amino acid sequence of a human VH acceptor FR as provided by NCBI Accession Code BAC01530.1, version 2.

SEQ ID NO:98 sets forth the amino acid sequence of a human VL acceptor FR as provided by NCBI Accession Code BAC01583.1, version 2.

SEQ ID NO:99 sets forth the nucleic acid sequence of the murine 6C12 light chain variable region, version 2.

SEQ ID NO:100 sets forth the nucleic acid sequence of humanized 15F7 light chain variable region version 1 (L1), version 2.

SEQ ID NO:101 sets forth the amino acid sequence of an exemplary human IgG1 constant region of the IgG1 G1m3 allotype.

SEQ ID NO:102 sets forth the nucleic acid sequence of an exemplary human kappa light chain constant region without a N-terminal arginine.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology* (Paul, W., ed., 2nd ed. Raven Press, N.Y., 1989), Ch. 7 (incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)). In some bispecific antibodies, the two different heavy/light chain pairs include a humanized 15F7 heavy chain/light chain pair and a heavy chain/light chain pair specific for a different epitope on laminin α4 than that bound by 15F7.

In some bispecific antibodies, one heavy chain light chain pair is a humanized 15F7 antibody as further disclosed below and the heavy light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal. et al., Sci. Trans. Med. 3, 84ra43, 2011; Yu et al., Sci. Trans. Med. 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include cancerous cells, or at least not known or suspect to include cancerous cells of a given type. Control samples can be obtained from individuals not afflicted with cancer or a specifically chosen type of cancer. Alternatively, control samples can be obtained from patients afflicted with cancer or a specifically chosen type of cancer. Such samples can be obtained at the same time as a biological sample thought to comprise the cancer or on a different occasion. A biological sample and a control sample can both be obtained from the same tissue (e.g., a tissue section containing both tumor tissue and surrounding normal tissue). Preferably, control samples consist essentially or entirely of normal, healthy cells and can be used in comparison to a biological sample thought to comprise cancer cells or a particular type of cancer cells. Preferably, the cells in the control sample have the same tissue origin as the cancer cells thought to be in the biological sample (e.g., lung or brain). Preferably, the cancer cells thought to be in the biological sample arise from the same cell type (e.g., neuronal, epithelial, mesenchymal, hematopoietic) as the type of cells in the control sample.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

Statistical significance means $p \leq 0.05$.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that specifically bind to the LG4-5 modules of the G domain of laminin α4. The antibodies have the ability selectively to stain cancer cells relative to normal tissue. The antibodies also have the ability to inhibit laminin-α4-mediated cancer or tumor cell adhesion. The antibodies can be used for detecting cancer, evaluating the efficacy of a cancer therapy, treating cancer, and treating obesity or obesity-related diseases, among other applications.

II. Target Molecules

Laminins are a family of extracellular matrix glycoproteins and are the major non-collagenous constitutent of basement membranes. They have been reported to be involved in biological processes including cell adhesion, differentiation, migration, signaling, neurite outgrowth, and metastasis, among other processes. Laminins are heterotrimeric proteins of three chains: an alpha chain, a beta chain, and a gamma chain. The three chains form a cruciform structure consisting of three short arms, each formed by a different chain, and a long arm composed of all three chains. In mammals, five different alpha chains, three different beta chains, and three different gamma chains have been identified that can assemble into fifteen different heterotrimeric combinations.

The laminin alpha chains have a large C-terminal globular domain (G domain) that has five tandem homologous laminin G-like modules (LG1-5) of about 200 amino acids. For example, the G domain of laminin α4 is defined by UniProt sequence Q16363 as amino acid positions 833-1820 (SEQ ID NO:4), and the five LG modules of laminin α4 are defined by UniProt sequence Q16363 as follows: LG1 (SEQ ID NO:5) includes amino acid positions 833-1035, LG2 (SEQ ID NO:6) includes amino acid positions 1047-1227, LG3 (SEQ ID NO:7) includes amino acid positions 1234-1402, LG4 (SEQ ID NO:9) includes amino acid positions 1469-1640, and LG5 (SEQ ID NO:10) includes amino acid positions 1647-1820. In some cases, the G domain can be SEQ ID NO:4; in other cases it can include amino acid positions 833-1820 of UniProt sequence Q16363. In some cases, the LG1 module can be SEQ ID NO:5; in other cases it can include amino acid positions 833-1035 of UniProt sequence Q16363. In some cases, the LG2 module can be SEQ ID NO:6; in other cases it can include amino acid positions 1047-1227 of UniProt sequence Q16363. In some cases, the LG3 module can be SEQ ID NO:7; in other cases it can include amino acid positions 1234-1402 of UniProt sequence Q16363. In some cases, the LG4 module can be SEQ ID NO:9; in other cases it can include amino acid positions 1469-1640 of UniProt sequence Q16363. In some cases, the LG5 module can be SEQ ID NO:10; in other cases it can include amino acid positions 1647-1820 of UniProt sequence Q16363. The LG1-3 modules (SEQ ID NO:8) are connected to the LG4-5 modules (SEQ ID NO:11) by a linker domain. The laminin α4 chain (also known as LAMA4, laminin subunit α4, laminin-14 subunit alpha, laminin-8 subunit alpha, and laminin-9 subunit alpha) is 200 kDa and is the shortest variant. Compared to the α1, α2, and α5 chains, laminin α4 has a truncated N-terminus. Laminin α4 is widely distributed both in adults and during development. It is present in laminin-8 (laminin 411 or alpha4/beta1/gamma1), laminin-9 (laminin 421 or alpha4/beta2/gamma1), and laminin-14 (laminin 411 or alpha4/beta1/gamma1).

Unless otherwise apparent from context, reference to laminin α4 or its fragments, domains, or modules includes the natural human amino acid sequences including isoforms and allelic variants thereof. Exemplary human sequences are designated UniProt Number Q16363 and GenBank Accession Numbers NP001098676 and NP001098677 (SEQ ID NOS:1, 2, and 3, respectively). Some antibodies bind to an epitope within the LG4-5 modules of the G domain of laminin α4. The epitope can be in LG4, in LG5, or split so that residues forming the epitope come from both LG4 and LG5.

Laminin α4 has been reported to be a binding partner for syndecans. For example, cells overexpressing syndecan-2 or -4 have been reported to bind to the LG4 module of the G domain of laminin α4. See Matsuura et al., J. Invest. Dermatol. 122:614-620 (2004). Syndecans are transmembrane heparan sulfate proteoglycan receptors that constitute the major physiological form of heparan sulfate on the cell surface. There are four reported members of the syndecan protein family: syndecan-1 (also known as SYND1, SDC1, SDC, or CD138), syndecan-2 (also known as SYND2, SDC2, fibroglycan, heparan sulfate proteoglycan core protein, HSPG, HSPG1, and CD362), syndecan-3 (also known as SYND3 and SDC3), and syndecan-4 (also known as SYND4, SDC4, amphiglycan, and ryudocan core protein). Syndecans have a short cytoplasmic domain, a single-span transmembrane domain, and an extracellular domain. They have been reported to bind to growth factors, cytokines, and extracellular matrix proteins. Syndecans have many reported biological roles including regulating cell growth, differentiation, angiogenesis, and adhesion, among other processes. Unless otherwise apparent from context, reference to a syndecan or its fragments or domains includes the natural human amino acid sequences including isoforms and allelic variants thereof. Exemplary human sequences are designated UniProt Numbers P18827 (syndecan-1), P34741 (syndecan-2), O75056 (syndecan-3), and P31431 (syndecan-4) (SEQ ID NOS:12-15, respectively).

The LG4 and LG5 modules of the G domain of laminin α4 also bind to other heparan sulfate proteoglycans including cell surface proteins such as glypicans, betaglycans, and CD44 (e.g., Swiss Prot. P16070), and matrix proteins such as perlecan (e.g., Swiss Prot. P98160), agrin (e.g., Swiss Prot. Q00468), and collagen XVIII (e.g., Swiss Prot. P39060). Binding of the LG4-5 modules of the G domain of laminin α4 to any or all of these or other proteoglycans may contribute to its growth promoting characteristics, inflammation, angiogenesis, and growth and metastasis of cancers.

III. Cancers

The above target molecules are involved in the development and/or progression of cancers. Cancer is a physiological condition in mammals that is typically characterized by unregulated cell growth and proliferation. Cancers can be hematopoietic malignancies or solid tumors, i.e., masses of cells that result from excessive cell growth or proliferation, including pre-cancerous legions. Metastatic cancer refers to a cancer that has spread from the place where it first started to another place in the body. Tumors formed by metastatic cancer cells are called a metastatic tumor or a metastasis, which is a term also used to refer to the process by which cancer cells spread to other parts of the body. In general, metastatic cancer has the same name and same type of cancer cells as the original, or primary, cancer. Examples solid tumors include melanoma, carcinoma, blastoma, and sarcoma. Hematologic malignancies include leukemia or lymphoid malignancies, such as lymphoma. More particular examples of such cancers include squamous cell cancer or carcinoma, lung cancer, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

IV. Antibodies

A. Binding Specificity and Functional Properties

The invention provides antibodies binding to epitopes within the LG4-5 modules of the G domain of laminin α4. For example, as defined by laminin α4 UniProt sequence Q16363, LG4 (SEQ ID NO:9) includes amino acid positions 1469-1640, LG5 (SEQ ID NO:10) includes amino acid positions 1647-1820, and LG4-5 (SEQ ID NO:11) includes amino acid positions 1469-1820. The epitope can be in LG4, in LG5, or split so that residues forming the epitope come from both LG4 and LG5. The epitope can be in particular segments within LG4-5, such as segments from laminin α4 UniProt sequence Q16363 ranging from positions 1469-1519, 1520-1570, 1571-1621, 1622-1672, 1673-1723, 1724-1774, and 1775-1820. The epitope can be linear, such as an epitope of, for example, 2-5, 3-5, 3-10, 3-15, 3-20, 5-10, 5-15, or 5-20 contiguous amino acids from LG4, LG5, LG4-5, or any of the segments or pairs of adjoining segments specified above. The epitope can also be a conformational epitope including, for example, 2-5, 3-5, 3-10, 3-15, 3-20, 5-10, 5-15, or 5-20 non-contiguous amino acids from any combination of LG4, LG5, LG4-5, and any of the segments specified above.

Antibodies designated 15F7, 6C12, and 13G10 are three such exemplary mouse antibodies. These three monoclonal antibodies each specifically bind to an epitope within the LG4 and/or LG5 modules of the G domain of laminin α4. These antibodies are further characterized by their lack of significant binding to the LG1-3 modules of the G domain of laminin α4 (e.g., same within experimental error as an irrelevant control antibody, or binding that is at least 2-fold, 3-fold, 4-fold, 5-fold, or 10-fold less (e.g., as measured by a flow cytometric binding assay) than an antibody specific for the LG1-3 modules). Some antibodies are characterized by their lack of significant binding to other laminin alpha chains, e.g., laminin α1, laminin α2, laminin α3, and laminin α5 (e.g., same within experimental error as an irrelevant control antibody, or binding that is at least 2-fold, 3-fold, 4-fold, 5-fold, or 10-fold less (e.g., as measured by a flow cytometric binding assay) than an antibody specific for the relevant other laminin alpha chain). Some antibodies are further characterized by their capacity selectively to bind a biological sample comprising cancer cells (e.g., a sample of tumor tissue) when compared to control sample (e.g., binding of the antibody to the biological sample is at least 1.5-fold, 2-fold, 5-fold, or 10-fold greater than binding of the antibody to the control sample), as shown in Example 2 with melanoma samples. Preferably, the control sample and the biological sample comprise cells of the same tissue origin. Ability to bind to specific proteins, modules, or domains can be demonstrated using exemplary assay formats provided in the examples. Likewise, ability to selectively bind and stain tumor tissue can be demonstrated using exemplary assay formats provided in the examples.

Some antibodies binding within LG4-5 lack capacity to inhibit binding of laminin α4 to MCAM (i.e., extent of inhibition the same within experimental error as an irrelevant control antibody). Some antibodies inhibit binding of laminin α4 to a syndecan, such as syndecan-1, syndecan-2, syndecan-3, or syndecan-4. Some antibodies inhibit binding of laminin α4 to other heparan sulfate proteoglycans including several other cell surface proteins including any or all of glypicans, betaglycans, and CD44, and matrix proteins such as perlecan, agrin, and collagen XVIII. Some of the disclosed antibodies can inhibit binding of the LG4-5 modules of the G domain of laminin α4 to any or all of these proteoglycans, and consequently or otherwise inhibit angiogenesis, inflammation and growth and metastasis of cancers.

Inhibition of binding of laminin α4 to a binding partner, for example a syndecan or other proteoglycan, can be tested in a binding assay in which an antibody is pre-incubated with recombinant laminin α4 protein, laminin-α4-positive tissue, or laminin-α4-displaying cells, after which recombinant proteoglycan or proteoglycan-expressing cells are then assessed for their ability to bind to laminin α4. Optionally, inhibition of a test antibody can be demonstrated in comparison to an irrelevant control antibody not binding within the LG4-5 modules of the G domain of laminin α4 or in comparison to vehicle lacking any antibody.

Some antibodies have the capacity to inhibit laminin-α4-mediated cell adhesion of cancer cells, preferably cell adhesion mediated by the LG4-5 modules of the G domain of laminin α4. An exemplary cell adhesion assay is described in the examples.

Some antibodies also have the capacity to inhibit laminin-α4-induced pAkt activation. An exemplary assay is described in the examples.

Inhibition means an inhibition of at least 10%, 20%, 25%, 30%, 40%, 50%, or 75%, (e.g., 10%-75% or 30%-70%) of binding, cell adhesion and/or other functional activity mediated by laminin α4, either alone or in combination with a syndecan or anything else contributing (e.g., other proteoglycan) to any of its functional activities. Inhibition can usually demonstrated when the antibody is present at a concentration of about 20 ug/ml. The antibodies can show inhibition of at least 30% of laminin-α4-mediated cell adhesion, such as, for example, cell adhesion mediated by the LG4-5 modules of the G domain of laminin α4.

Preferred antibodies inhibit cancer development or progression, or any aspect thereof, such as metastasis, as shown in an animal model or clinical trial. Animal models of cancer in which human cancer cells are injected into an immuno-deficient laboratory animal, such as a mouse or rat, or transgenic models in which a laboratory animal expresses a human oncogene or has a knocked out tumor suppressor gene, are widely available. In addition, cell-based assays for particular characteristics of cancer cells, such as proliferation assays, growth assays, survival assays, migration assays, invasion assays, and others, are widely available.

Some antibodies bind to the same or overlapping epitope as an antibody designated 15F7, 6C12, or 13G10. The sequences of the heavy and light chain mature variable regions of these antibodies are designated SEQ ID NOS:16 and 17, 26 and 27, and 36/37 and 38, respectively. Another version of the light chain mature variable region of 6C12 is SEQ ID NO:94. Other antibodies having such a binding specificity can be produced by immunizing mice with laminin α4, or a portion thereof including the desired epitope, and screening resulting antibodies for binding to the LG4-5 modules of the G domain of laminin α4, optionally in competition with 15F7, 6C12, or 13G10. Antibodies identified by such assays can then be screened for ability to specifically bind to the LG4-5 modules but not the LG1-3 modules of the G domain of laminin α4 as described in the examples or otherwise. Antibodies can also be screened for ability to selectively stain tumor tissue as described in the examples or otherwise. Antibodies can also be screened for ability to inhibit laminin-α4-mediated tumor cell adhesion as described in the examples or otherwise.

Antibodies binding to an epitope that includes one or more specified residues can be generated by immunizing with a fragment of laminin α4 that includes these one or more residues. The fragment can, for example, have no more than 100, 50, 25, 10 or 5 contiguous amino acids from SEQ ID NO:11. Such fragments usually have at least 5, 6, 7, 8 or 9 contiguous residues of SEQ ID NO:11. The fragments can be linked to a carrier that helps elicit an antibody response to the fragment and/or be combined with an adjuvant that helps elicit such a response. Alternatively, antibodies binding to a desired residue can be obtained by immunizing with a full-length laminin α4 (SEQ ID NO:1) or the full-length G domain of laminin α4 (SEQ ID NO:4) or the LG4-5 modules of the G domain of laminin α4 (SEQ ID NO:11) or fragments of any of these. Such antibodies can then be screened for differential binding to versions of laminin α4 containing different LG modules of the G domain, such as LG1-3, LG1-5, LG4-5, LG4, or LG5 (SEQ ID NOS:8, 4, 11, 9, and 10, respectively) or differential binding to wild type laminin α4 compared with mutants of specified residues. The screen against versions of laminin α4 with different LG modules of the G domain maps antibody binding to certain LG modules within the G domain of laminin α4. The screen against mutants more precisely defines the binding specificity to allow identification of antibodies whose binding is inhibited by mutagenesis of particular residues and which are likely to share inhibitor properties of other exemplified antibodies.

Human antibodies having the binding specificity of a selected murine antibody (e.g., 15F7, 6C12, or 13G10) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for the LG4-5 modules of the G domain of laminin α4 (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for the LG4-5 modules of the G domain of laminin α4 are selected. The resulting antibodies usually have the same or similar epitope specificity as the murine starting material.

Other antibodies can be obtained by mutagenesis of cDNA encoding the heavy and light chains of an exemplary antibody, such as 15F7, 6C12, or 13G10. Monoclonal antibodies that are at least 70%, 80%, 90%, 95%, 96%, 97%, 98%, or 99% identical to 15F7, 6C12, or 13G10 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by Kabat that are 90%, 95%, 99% or 100% identical to corresponding CDRs of 15F7, 6C12, or 13G10 are also included.

The invention also provides antibodies having some or all (e.g., 3, 4, 5, and 6) CDRs entirely or substantially from 15F7, 6C12, or 13G10. Such antibodies can include a heavy chain variable region that has at least two, and usually all three, CDRs entirely or substantially from the heavy chain variable region of 15F7, 6C12, or 13G10 and/or a light chain variable region having at least two, and usually all three, CDRs entirely or substantially from the light chain variable region of 15F7, 6C12, or 13G10. The antibodies can include both heavy and light chains. A CDR is substantially from a corresponding 15F7, 6C12, or 13G10 CDR when it contains no more than 4, 3, 2, or 1 substitutions, insertions, or deletions, except that CDRH2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 15F7, 6C12, or 13G10 in the amino acid sequence of the mature heavy and/or light chain variable regions and maintain their functional properties, and/or differ from 15F7, 6C12, or 13G10 by a small number of functionally inconsequential amino acid substitutions (e.g., conservative substitutions), deletions, or insertions.

B. Non-Human Antibodies

The production of other non-human antibodies, e.g., murine, guinea pig, primate, rabbit or rat, against the LG4-5 modules of the G domain of laminin α4 can be accomplished by, for example, immunizing the animal with laminin α4 or a fragment thereof. See Harlow & Lane, *Antibodies, A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to the LG4-5 modules of the G domain of laminin α4. Such screening can be accomplished by determining binding of an antibody to a collection of laminin α4 variants, such as laminin α4 variants containing the LG1-3 modules of the G domain, the LG1-5 modules of the G domain, and the LG4-5 modules of the G domain, and determining which laminin α4 variants bind to the antibody. Binding can be assessed, for example, by Western blot, FACS or ELISA.

C. Humanized Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs) from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Examples of acceptor sequences for the heavy chain are the human mature heavy chain variable regions with NCBI accession codes ACF36857.1 and BAC01530.1 (SEQ ID NOS:51 and 52, respectively). Other versions of ACF36857.1 and BAC01530.1 are SEQ ID NOS:96 and 97, respectively. These acceptor sequences include two CDRs having the same canonical form as mouse 15F7 heavy chain. Examples of acceptor sequences for the light chain are the human mature light chain variable regions with NCBI accession codes AAY33350.1 and BAC01583.1 (SEQ ID NOS:53 and 54, respectively). Another version of BAC01583.1 is SEQ ID NO:98. These acceptor sequences include three CDRs having the same canonical form as mouse 15F7 light chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region or within a CDR as defined by Chothia but not Kabat,
(3) otherwise interacts with a CDR region (e.g. is within about 6 Å of a CDR region), (e.g., identified by modeling the light or heavy chain on the solved structure of a homologous known immunoglobulin chain), or
(4) is a residue participating in the VL-VH interface.

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, J. Mol. Biol. 196:901-917 (1987); Thornton & Martin, J. Mol. Biol. 263:800-815 (1996)). Framework residues that support antigen-binding loop conformations and play a role in fine-tuning the fit of an antibody to antigen are sometimes referred to as vernier residues (Foote & Winter, J. Mol. Viol 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Exemplary humanized antibodies are humanized forms of the mouse 15F7 antibody, designated Hu15F7. The mouse antibody comprises mature heavy and light chain variable regions having amino acid sequences comprising SEQ ID NO:16 and SEQ ID NO:17, respectively. The invention provides two exemplified humanized mature heavy chain variable regions: Hu15F7VHv1 (H1; SEQ ID NO:57) and Hui5F7VHv2 (H2; SEQ ID NO:58). The invention further provides two exemplified human mature light chain variable regions: Hui5F7VLv1 (L1; SEQ ID NO:59) and Hui5F7VLv2 (L2; SEQ ID NO:60).

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 20 variable region framework positions were considered as candidates for substitutions in the two exemplified human mature light chain variable regions and the two exemplified human mature heavy chain variable regions, as further specified in the examples: L8 (P8S), L42 (K42N), L45 (K45R), L49 (Y49S), L69 (T69K), L80 (P80T), H1 (Q1E), H20 (V20L), H27 (G27Y), H30 (S30T), H38 (R38K), H40 (A40R), H41 (P41A), H48 (M48I), H66 (R66K), H67 (V67A), H69 (I69L), H75 (T75S), H82A (S(82A)R), and H91 (Y91F). In addition, L104 (L104V) was considered as a candidate for substitution in the two exemplified human mature light chain variable regions.

Here, as elsewhere, the first-mentioned residue is the residue of a humanized antibody formed by grafting Kabat CDRs into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions (e.g., VHv1/VLv1 or H1L1, VHv1/VLv2 or H1L2, VHv2/VLv1 or H2L1, and VHv2/VLv2 or H2L2).

Figure 8:
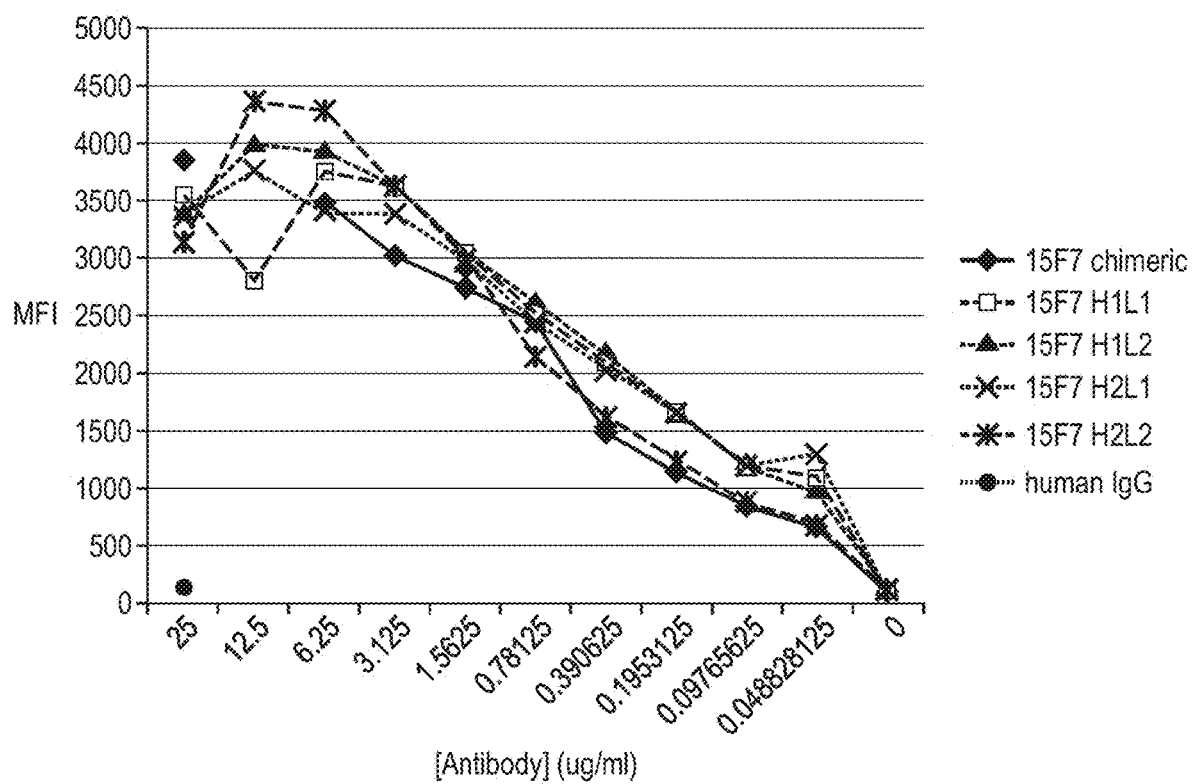
FIG. 8 shows the capacity of serially diluted chimeric 15F7 and humanized 15F7 variants H1L1, H1L2, H2L1, and H2L2 to bind to LAMA4-displaying cells as assessed by flow cytometry.

For example, the H1L1 antibody, which includes 14 heavy chain backmutations or other mutations and 6 light chain backmutations as described below, binds to laminin α4 and inhibits MCAM binding to laminin α4 at a level that is substantially the same as, if not superior to, a chimeric 19C12 antibody (see FIGS. 8-10). Comparable results are seen with the H1L2, H2L1, and H2L2 antibodies (see FIGS. 8-10).

The invention provides variants of the H1L1 humanized 15F7 antibody in which the humanized mature heavy chain variable region shows at least 90%, 95%, 96%, 97%, 98%, or 99% identity to H1 (SEQ ID NO:57) and the humanized mature light chain variable region shows at least 90%, 95%, 96%, 97%, 98%, or 99% identity to L1 (SEQ ID NO:59). In some such antibodies at least 1, 2, 3, 4, 5, 6, 7, 8, 9, 10, 11, 12, 13, 14, 15, 16, 17, 18, 19, or all 20 of the backmutations or other mutations in H1L1 are retained. The invention also provides variants of the H2L1 humanized 15F7 antibody in which the humanized mature heavy chain variable region shows at least 90%, 95%, 96%, 97%, 98%, or 99% identity to H2 (SEQ ID NO:58) and the humanized mature light chain variable region shows at least 90%, 95%, 96%, 97%, 98%, or 99% identity to L1 (SEQ ID NO:59). In some such antibodies at least 1, 2, 3, 4, 5, 6, 7, 8, 9, 10, 11, 12, 13, 14, 15, 16, 17, or all 18 of the backmutations or other mutations in H2L1 are retained. In some antibodies, at least one of positions H1, H20, H27, H30, H38, H40, H48, H66, H67, H75, H82A, and H91 in the Vh region is occupied by E, L, Y, T, K, R, I, K, A, S, R, and F, respectively. In some antibodies, positions H1, H20, H27, H30, H38, H40, H48, H66, H67, H75, H82A, and H91 in the Vh region are occupied by E, L, Y, T, K, R, I, K, A, S, R, and F, respectively, such as in version H2. In some antibodies, at least one of positions H41 and H69 in the Vh region is occupied by A and L, respectively. In some antibodies, positions H41 and H69 in the Vh region are occupied by A and L, respectively, such as in version H1. In some antibodies, at least one of positions L42, L49, and L69 in the Vk region is occupied by N, S, and K, respectively. In some antibodies, positions L42, L49, and L69 in the Vk region are occupied by N, S, and K, respectively, such as in version L2. In some antibodies, at least one of positions L8, L45, and L80 in the Vk region is occupied by S, R, and T, respectively. In some antibodies, at least one of positions L8, L45, L80, and L104 in the Vk region is occupied by S, R, T, and V, respectively. In some antibodies, positions L8, L45, and L80 in the Vk region are occupied by S, R, and T, respectively, such as in version L1. In some antibodies, L104 is occupied by V, such as in version L2. The CDR regions of such humanized antibodies can be identical or substantially identical to the CDR regions of H1L1, which are the same as those of the mouse donor antibody. The CDR regions can be defined by any conventional definition (e.g., Chothia) but are preferably as defined by Kabat.

The invention also provides variants of the other exemplified Hu15F7 antibodies. Such variants have mature light and heavy chain variable regions showing at least 90%, 95%, 96%, 97%, 98%, or 99% sequence identity to the mature light and heavy chain variable regions of the exemplified humanized 15F7 H1L2, H2L1, or H2L2 antibodies. The CDR regions of such humanized antibodies can be identical or substantially identical to those of the mouse donor antibody. The CDR regions can be defined by any conventional definition (e.g., Chothia) but are preferably defined by Kabat. Variable regions framework positions are in accordance with Kabat numbering unless otherwise stated. Other such variants typically differ from the sequences of the exemplified Hu15F7 antibodies by a small number (e.g., typically no more than 1, 2, 3, 5, 10, or 15) of replacements, deletions or insertions. Such differences are usually in the framework but can also occur in the CDRs.

A possibility for additional variation in humanized 15F7 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in Hu15F7 (whether or not conservative) have no substantial effect on the binding affinity or potency of the humanized mAb, that is, its ability to bind to laminin α4 or the LG4-5 modules of the G domain of laminin α4 (e.g., the potency in some or all of the assays described in the present examples of the variant humanized 15F7 antibody is essentially the same, i.e., within experimental error, as that of murine 15F7 or H1L1).

D. Chimeric and Veneered Antibodies

The invention further provides chimeric and veneered forms of non-human antibodies, particularly the 15F7, 6C12, or 13G10 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 15F7 antibody are included in the invention.

E. Human Antibodies

Human antibodies against the LG4-5 modules of the G domain of laminin α4 are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of laminin α4, such as a laminin α4 variant containing only the LG4-5 modules of the G domain, as the target antigen, and/or by screening antibodies against a collection of laminin α4 variants, such as laminin α4 variants containing the LG1-3 modules of the G domain, the LG1-5 modules of the G domain, and the LG4-5 modules of the G domain.

Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991)) and phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332).

F. Selection of Constant Region

The heavy and light chain variable regions of chimeric, humanized (including veneered), or human antibodies can be linked to at least a portion of a human constant region. The choice of constant region depends, in part, on whether antibody-dependent complement and/or cellular mediated cytotoxicity is desired. For example, human isotypes IgG1 and IgG3 have complement-mediated cytotoxicity and human isotypes IgG2 and IgG4 do not. Human IgG1 and IgG3 also induce stronger cell mediated effector functions than human IgG2 and IgG4. A human IgG1 constant region suitable for inclusion in the antibodies can have the sequence of SEQ ID NO:61. The C-terminal lysine of SEQ ID NO:61 can be omitted, in which case the IgG1 constant region has the amino acid sequence of SEQ ID NO:91. Light chain constant regions can be lambda or kappa. A human kappa light chain constant region suitable for inclusion in the antibodies can have the sequence of SEQ ID NO:90. SEQ ID NO:90 can be encoded by the nucleic acid sequence of SEQ ID NO:93. The N-terminal arginine of SEQ ID NO:90 can be omitted, in which case the kappa light chain constant region has the amino acid sequence of SEQ ID NO:62. SEQ ID NO:62 can be encoded by the nucleic acid sequence of SEQ ID NO:102. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of the IgG1 G1m3 allotype and has the amino acid sequence of SEQ ID NO:89. SEQ ID NO:89 can be encoded by the nucleic acid sequence of SEQ ID NO:92. Another heavy chain constant region of the IgG1 G1m3 allotype has the amino acid sequence of SEQ ID NO:101. Reference to a human constant region includes a constant region with any natural allotype or any permutation of residues occupying polymorphic positions in natural allotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering) for increasing the half-life of an antibody. Substitution at any of positions 234, 235, 236 and/or 237 reduces affinity for Fcγ receptors, particularly FcγRI receptor (see, e.g., U.S. Pat. No. 6,624,821). An alanine substitution at positions 234, 235, and 237 of human IgG1 can be used for reducing effector functions. Optionally, positions 234, 236 and/or 237 in human IgG2 are substituted with alanine and position 235 with glutamine. See, e.g., U.S. Pat. No. 5,624,821. In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine, such as in SEQ ID NO:101. In some antibodies, the isotype is human IgG2 or IgG4.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NO:61, which encodes a human IgG1 constant region, and SEQ ID NO:62, which encodes a human kappa light chain constant region.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464, 6,114,148, 6,063,598, 7,569,339, WO2004/050884, WO2008/012142, WO2008/012142, WO2005/019442, WO2008/107388, and WO2009/027471, and U.S. Pat. No. 5,888,809).

H. Nucleic Acids

The invention further provides nucleic acids encoding any of the heavy and light chains described above (e.g., SEQ ID NOS:63-64, 67-68, 71-73, and 77-80). SEQ ID NOS:92-93, 99-100, and 102 are additional examples of nucleic acids encoding heavy and light chains described above. Typically, the nucleic acids also encode a signal peptide fused to the mature heavy and light chains (e.g., signal peptides having amino acid sequences of SEQ ID NOS:18, 28, 39, and 40 (heavy chain) and 19, 29, and 41 (light chain) that can be encoded by SEQ ID NOS:65, 69, 74, and 75, respectively (heavy chain) and 66, 70, and 76, respectively (light chain)). Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

I. Conjugated Antibodies

Antibodies that specifically bind to antigens, such as the LG4-5 modules of the G domain of laminin α4, that are preferentially present in cancers and tumors are useful in targeting cancer or tumor cells for destruction. Likewise, antibodies that specifically bind the LG4-5 modules of the G domain of laminin α4 can be useful in targeting cells involved in autoimmune diseases or any other diseases mediated at least in part by expression of the LG4-5 modules of the G domain of laminin α4. For example, such antibodies can be conjugated with other therapeutic or cytotoxic agents. See WO 03/057838. Likewise, such antibodies can be conjugated with other proteins, other antibodies, and/or detectable labels. See WO 03/057838; U.S. Pat. No. 8,455, 622. Such therapeutic agents can be any agent that can be used to treat, combat, ameliorate, prevent, or improve an unwanted condition or disease in a patient. Examples of such conditions or diseases include cancers and autoimmune diseases. Therapeutic agents include cytotoxic agents, cytostatic agents, radiotherapeutic agents, immunomodulators, or any biologically active agents that facilitate or enhance the activity of the antibody. Such cytotoxic agents can be any agent that is toxic to a cell. A cytostatic agent can be any agent that inhibits cell proliferation. An immunomodulator can be any agent that stimulates or inhibits the development or maintenance of an immunologic response. A radiotherapeutic agent can be any molecule or compound that emits radiation. If such therapeutic or cytotoxic agents are coupled to a tumor-specific antibody, such as the antibodies described herein, the coupled therapeutic or cytotoxic agents will have a specific affinity for tumor cells or cancer cells over normal cells. Likewise, the coupled therapeutic or cytotoxic agents will have a specific affinity for laminin-α4-expressing cells over other cells. Consequently, administration of the conjugated antibodies directly targets cancer cells with minimal damage to surrounding normal, healthy tissue. This can be particularly useful for therapeutic or cytotoxic agents that are too toxic to be administered on their own. In addition, smaller quantities of the therapeutic or cytotoxic agents can be used.

Antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio)propionate for ricin. See Pietersz et al., Cancer Res. 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., Leukemia 18:1215-1222 (2004).

Radioisotopes can also be linked to antibodies, such as, for example, yttrium$^{90}$ (90Y), indium$^{111}$ (111In), $^{131}$I, $^{99m}$Tc, radiosilver-111, radiosilver-199, and Bismuth$^{213}$. Linkage of radioisotopes to antibodies may be performed with conventional bifunction chelates. For radiosilver-11 and radiosilver-199 linkage, sulfur-based linkers may be used. See Hazra et al., Cell Biophys. 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, Cancer Chemother. Pharmacol., 48 Suppl 1:S91-S95 (2001).

Other therapeutic agents may also be linked to antibodies. Therapeutic agents are usually cytotoxic or cytostatic. For example, antibodies can be conjugated with toxic chemotherapeutic drugs such as maytansine, geldanamycin, tubulin inhibitors, such as tubulin binding agents (e.g., auristatins), or minor groove binding agents, such as calicheamicin. Other representative therapeutic agents include agents known to be useful for treatment, management, or amelioration of a cancer or an autoimmune disease or symptoms of a cancer or an autoimmune disease. Examples of such therapeutic agents are disclosed elsewhere herein.

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., J. Biol. Chem. 282:3196-3204 (2007); Bertschinger et al., Protein Eng. Des. Sel. 20:57-68 (2007); Schlatter et al., MAbs. 4:497-508 (2011); Banner et al., Acta. Crystallogr. D. Biol. Crystallogr. 69(Pt6):1124-1137 (2013); and Brack et al., Mol. Cancer Ther. 13:2030-2039 (2014).

The antibodies disclosed herein can also be coupled or conjugated to one or more other antibodies (e.g., to form antibody heteroconjugates). Such other antibodies can bind to different epitopes within the LG4-5 modules of the G domain of laminin α4, or can bind to a different target antigen.

Antibodies can also be coupled with a detectable label. Such antibodies can be used, for example, for diagnosing a cancer or an autoimmune disease, for monitoring progression of a cancer or an autoimmune disease, and/or for assessing efficacy of treatment. Such antibodies can be useful for performing such determinations in subjects having or being susceptible to a cancer or an autoimmune disease, or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I), carbon ($^{14}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$5 n, and $^{117}$Tin; positron emitting metals using various positron emission tomographies; nonradioactive paramagnetic metal ions; and molecules that are radiolabelled or conjugated to specific radioisotopes.

Therapeutic agents, other proteins, other antibodies, and/or detectable labels may be coupled or conjugated, directly or indirectly through an intermediate (e.g., a linker), to a murine, chimeric, veneered, or humanized antibody using techniques known in the art. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp.

623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., Immunol. Rev., 62:119-58 (1982). Suitable linkers include, for example, cleavable and non-cleavable linkers. Different linkers that release the drugs under acidic or reducing conditions or on exposure to specific proteases can be employed. Likewise, different linkers that release the coupled therapeutic agents, proteins, antibodies, and/or detectable labels under acidic or reducing conditions, on exposure to specific proteases, or under other defined conditions can be employed.

V. Therapeutic Applications

The above antibodies can be used for treating or effecting prophylaxis of a disease in a patient having or at risk for the disease mediated at least in part by expression of the LG4-5 modules of the G domain of laminin α4. In some such diseases, the LG4-5 modules of the G domain of laminin α4 contribute to progression of the disease by means of interaction with a heparan sulfate proteoglycan, such as syndecan-1, syndecan-2, syndecan-3, or syndecan-4.

Such a disease can be a cancer. Exemplary cancers to be treated have been described above. The methods are particularly amenable to treatment of a cancer showing a detectable level of the LG4-5 modules of the G domain of laminin α4 (e.g., by immunoassay using one of the disclosed antibodies). Some such cancers show an increased expression of laminin α4 compared with noncancerous tissue of the same type. Some such cancers are those that have been reported to be associated with laminin α4 expression, including glioma and glial tumors (see, e.g., Nagato et al., Int. J. Cancer 117:41-50 (2005); Ljubimova et al., Cancer 101(3):604-612 (2004)), hepatocellular carcinoma (see, e.g., Huang et al., J Cancer Res. Clin. Oncol. 134(6):705-14 (2008)), renal cell carcinoma (see, e.g., Vainionpaa et al., Lab Invest. 87(8):780-791 (2007)), oral squamous cell carcinoma (see, e.g., Takkunen et al., Histochem. Cell Biol. 130(3):509-525 (2008)), prostate cancer (see, e.g., Sprenger et al., Neoplasia 10(12):1350-1361 (2008)), and melanoma (see, e.g., Lugassy et al., J. Cutan. Pathol. 36(12):1237-1243 (2009)). Some such cancers are those associated with expression of one or more syndecans, such as breast cancer, cancer of the uterine cervix, colorectal cancer, endometrial cancer, fibrosarcoma, gallbladder cancer, gastric cancer, glioma, head and neck cancer, hepatocellular carcinoma, juvenile nasopharyngeal angiofibroma, lung cancer, melanoma, mesothelioma, myeloma, neuroendocrine tumors, oral cancer, oral squamous cell carcinoma, osteosarcoma, ovarian cancer, pancreatic cancer, and prostate cancer. See, e.g., Theocharis et al., FEBS Journal 277:3904-3923 (2010). Some of the above antibodies are useful for the treatment of melanoma, breast cancer, lung cancer, and colorectal cancer. Some antibodies may be useful for the treatment of uterine cancer, cervical cancer, endometrial cancer, fibrosarcoma, gallbladder cancer, gastric cancer, glioma, head and neck cancer, hepatoceullular carcinoma, juvenile nasopharyngeal angiofibroma, mesothelioma, myeloma, neuroendocrine, tumors, oral cancer, squamous cell carcinoma, oral squamous cell carcinoma, osteosarcoma, pancreatic cancer and/or prostate cancer. Some antibodies may be useful in treating metastatic tumors. In some instances the patient has a brain cancer or another type of CNS or intracranial tumor. For example, the patient can have an astrocytic tumor (e.g., astrocytoma, anaplastic astrocytoma, glioblastoma, pilocytic astrocytoma, subependymal giant cell astrocytoma, pleomorphic xanthoastrocytoma), oligodendroglial tumor (e.g., oligodendroglioma, anaplastic oligodendroglioma), ependymal cell tumor (e.g., ependymoma, anaplastic ependymoma, myxopapillary ependymoma, subependymoma), mixed glioma (e.g., mixed oligoastrocytoma, anaplastic oligoastrocytoma), neuroepithelial tumor of uncertain origin (e.g., polar spongioblastoma, astroblastoma, gliomatosis cerebri), tumor of the choroid plexus (e.g., choroid plexus papilloma, choroid plexus carcinoma), neuronal or mixed neuronal-glial tumor (e.g., gangliocytoma, dyplastic gangliocytoma of cerebellum, ganglioglioma, anaplastic ganglioglioma, desmoplastic infantile ganglioma, central neurocytoma, dysembryoplastic neuroepithelial tumor, olfactory neuroblastoma), pineal parenchyma tumor (e.g., pineocytoma, pineoblastoma, mixed pineocytoma/pineoblastoma), or tumor with mixed neuroblastic or glioblastic elements (e.g., medulloepithelioma, medulloblastoma, neuroblastoma, retinoblastoma, ependymoblastoma). Some antibodies may be useful in treating other cancers.

Such a disease can be an autoimmune disease. Autoimmune diseases include systemic autoimmune diseases, organ- or tissue-specific autoimmune diseases, and diseases that exhibit autoimmune-type expressions. In these diseases, the body develops a cellular and/or humoral immune response against one of its own antigens, leading to destruction of that antigen and potentially crippling and/or fatal consequences. The cellular response if present can be B-cell or T-cell or both. TH17 cells, a lineage T helper cells characterized by production of interleukin (IL)-17 and IL-22, have been reported to enter tissues to facilitate pathogenic autoimmune responses, including multiple sclerosis in humans and experimental autoimmune encephalomyelitis (EAE) in mice. See, e.g., Cua et al., Nature 421: 744-748 (2003); Ivonov et al., Cell 126: 1121-1133 (2006). TH17 cells may initiate or propagate an inflammatory response by their specific recruitment to and infiltration of tissue.

Examples of autoimmune diseases include Graves' disease, Hashimoto's thyroiditis, autoimmune polyglandular syndrome, insulin-dependent diabetes mellitus (type 1 diabetes), insulin-resistant diabetes mellitus (type 2 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, idiopathic thrombocytopenic purpura, autoimmune thrombocytopenic purpura, pernicious anemia, myasthenia gravis, Guillain-Barre syndrome, stiff man syndrome, acute rheumatic fever, sympathetic ophthalmia, Goodpasture's syndrome, autoimmune uveitis, temporal arteritis, Bechet's disease, inflammatory bowel diseases, Crohn's disease, ulcerative colitis, primary biliary cirrhosis, autoimmune hepatitis, autoimmune oophoritis, fibromyalgia, polymyositis, dermatomyostis, ankylosing spondylitis, Takayashu arteritis, panniculitis, pemphigoid, vasculitis of unknown origin, anca negative vasculitis, anca positive vasculitis, systemic lupus erythematosus, psoriatic arthritis, rheumatoid arthritis, scleroderma, systemic necrotizing vasculitis, Wegener's granulomatosis, CREST syndrome, antiphospholipid syndrome, Sjogren's syndrome, eosinophilic gastroenteritis, atypical topical dermatitis, cardiomyopathy, post-infectious syndromes, postinfectious endomyocarditis, celiac disease, multiple sclerosis, sarcoidosis, and psoriasis Although an understanding of mechanism is not required for practice, it is believed that any or all of the following mechanisms may contribute to treatment of cancer. The antibodies may treat the cancer by inhibiting tumor cell adhesion, inhibiting laminin-α4-mediated signaling events, or inhibiting interaction of laminin α4 with a syndecan. The antibodies may additionally or alternatively treat cancer by inducing processing or clearance of the LG4-5 modules of the G domain of laminin α4. The antibodies may additionally or alternatively inhibit metastasis or cancer cell invasion. Binding of antibodies to LG4-5 modules of the G domain of laminin α4 may also affect cell adhesion, signaling mechanisms involved in cell proliferation, growth, resisting cell death, angiogenesis, or other characteristics of cancers. The antibodies may inhibit tumor growth via inhibiting Akt activation and subsequent cell survival/proliferation signaling. In some instances, the antibodies disrupt or inhibit angiogenesis by altering endothelial Dll4/Notch signaling. In some cases, the disruption or inhibition of angiogenesis by the antibodies involves disrupting the interaction between laminin α4 and integrins, such as integrins comprising integrin α2, integrin α6, or integrin β1. Antibody-drug conjugates have additional mechanisms of action including the cytotoxic or cytostatic effect of the linked agent, typically after uptake within a cancer cell. Antibody-drug conjugates can also act by such mechanisms of action in other targeted cells. Antibody-drug conjugates may also induce tumor-associated macrophage toxicity.

Other diseases treatable by antibodies of the invention include obesity and obesity-related diseases, such as obesity-related orphan diseases. Obesity is a disease caused by excessive food energy intake, lack of physical activity, and/or genetic susceptibility. A body mass index (BMI) >35 indicates severe obesity, a BMI >40 indicates morbid obesity, and a BMI >45 indicates super obesity. Obesity-related diseases include diseases and disorders that are associated with, are caused by, or result from obesity. Examples of obesity-related diseases include cardiovascular diseases, type 2 diabetes, sleep apnea, cancer, osteoarthritis, asthma, fatty liver, and non-alcoholic steatohepatitis (NASH).

NASH is characterized by hepatic inflammation and fat accumulation. The primary risk factors are obesity, diabetes, and dyslipidemia. There is a strong link with cirrhosis and hepatocarcinoma. NASH is associated with elevated AST/ALT (ratio of concentration of aspartate transaminase (AST) and alanine transaminase (ALT)), often without symptoms. Treatments for NASH include lifestyle changes (diet and exercise), bariatric surgery, and pharmaceuticals with mechanisms including absorption reduction (Xenical/Alli (lipase inhibitor)), appetite suppression (Belviq, Byetta, Symlin, Qsymia), and metabolic stimulation (Beloranib).

Examples of obesity-related orphan diseases include Prader-Willi syndrome (e.g., with hyperphagia), craniopharyngioma (e.g., with hyperphagia), Bardet-Biedl syndrome, Cohen syndrome, and MOMO syndrome. Prader-Willi syndrome is a rare genetic disease caused by gene deletion/silencing on chromosome 15. The symptoms include neurocognitive symptoms (intellectual disability, autistic behaviors, uncontrolled appetite (hypothalamic)), slow metabolism, and endocrine disorders (e.g., growth hormone deficiency (GHD), adrenal deficiency (AD)).

Antibodies are administered in an effective regime meaning a dosage, route of administration and frequency of administration that delays the onset, reduces the severity, inhibits further deterioration, and/or ameliorates at least one sign or symptom of a disorder being treated (e.g., cancer). If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-20, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with antibodies described herein can be combined with other treatments effective against the disorder being treated. When used in treating cancer, the antibodies can be combined with chemotherapy, radiation, stem cell treatment, surgery, or treatment with other biologics including Herceptin® (trastuzumab) against the HER2 antigen, Avastin® (bevacizumab) against VEGF, or antibodies to the EGF receptor, such as (Erbitux®, cetuximab), and Vectibix® (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine.

VI. Other Applications

The antibodies can be used for detecting laminin α4 in the context of clinical diagnosis or treatment or in research. More specifically, the antibodies can also be used for detecting the LG4-5 modules of the G domain of laminin α4, or fragments thereof, in the context of clinical diagnosis or treatment or in research. For example, the antibodies can be used to detect the presence of the LG4-5 modules of the G domain of laminin α4 in a biological sample as an indication that the biological sample comprises cancer cells or tumor cells. Binding of the antibodies to the biological sample can be compared to binding of the antibodies to a control sample. The control sample and the biological sample can comprise cells of the same tissue origin. In some assays, the cancer cells that may be present in the biological sample arose from the same cell type as the type of cells in the control sample. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of the LG4-5 modules of the G domain of laminin α4) to the biological sample(s) is increased, decreased, or the same relative to antibody binding to the control sample(s). Increased binding of the antibody to the biological sample(s) relative to the control sample(s) indicates the presence of cancer in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of the LG4-5 modules of the G domain of laminin α4 in a biological sample to monitor and evaluate the efficacy of a therapeutic agent being used to treat a patient diagnosed with cancer. A biological sample from a patient diagnosed with cancer is evaluated to establish a baseline for the binding of the antibodies to the sample (i.e., a baseline for the presence of the LG4-5 modules of the G domain of laminin α4 in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of the LG4-5 modules of the G domain of laminin α4) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of the LG4-5 modules of the G domain of laminin α4) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of the LG4-5 modules of the G domain of laminin α4 has decreased), it can be concluded that the therapeutic agent was effective in treating the cancer in the patient. Preferably, the decrease in antibody binding is statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of cancer.

The antibodies can also be used as research reagents for laboratory research in detecting laminin α4, or more specifically, the LG4-5 modules, or fragments thereof, of the G domain of laminin α4. In such uses, antibodies can be labeled with fluorescent molecules, spin-labeled molecules, enzymes, or radioisotopes, and can be provided in the form of kit with all the necessary reagents to perform the assay for laminin α4, or more specifically, the LG4-5 modules of the G domain of laminin α4, or fragments thereof. The antibodies can also be used to purify laminin α4, laminins containing laminin α4, or binding partners of laminin α4, e.g., by affinity chromatography.

The antibodies can also be used for inhibiting cell adhesion in a biological sample. Preferably, the cell adhesion is dependent on laminin α4. For example, the cell adhesion is mediated by the LG4-5 modules of the G domain of laminin α4. The biological sample can comprises a tumor, cancer, or cells derived therefrom. Optionally, the tumor or cancer is melanoma. An exemplary cell adhesion assay is described in the examples. In some instances, cell adhesion is inhibited by at least 10%, 20%, 25%, 30%, 40%, 50%, or 75%, (e.g., 10%-75% or 30%-70%)

The antibodies can also be used for inhibiting binding of laminin α4 to a syndecan in a biological sample. Optionally, the syndecan is syndecan-1, syndecan-2, syndecan-3, or syndecan-4. Inhibition may be demonstrated in a binding assay assessing the ability of syndecan-expressing cells to bind laminin α4 in the presence or absence of the antibodies. Optionally, inhibition of a test antibody can be demonstrated in comparison to an irrelevant control antibody not binding to the LG4-5 modules of the G domain of laminin α4 or in comparison to vehicle lacking any antibody. For example, binding of laminin α4 to the syndecan is inhibited by at least 10%, 20%, 25%, 30%, 40%, 50%, or 75%, (e.g., 10%-75% or 30%-70%).

The antibodies can also be used for inhibiting laminin-α4-induced pAkt activation in a biological sample. An exemplary assay is described in the examples. In some methods, laminin-α4-induced pAkt activation is inhibited by at least 10%, 20%, 25%, 30%, 40%, 50%, or 75%, (e.g., 10%-75% or 30%-70%).

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of LG4-5-Domain-Specific Anti-LAMA4 Monoclonal Antibodies LAMA4 tumor expression has been reported to correlate with tumor grade, recurrence, and survival, while down-regulation has been reported to inhibit tumor invasion in vitro and in vivo. See, e.g., Ljubimova et al., Cancer 101: 604-612 (2004) and Nagato et al., Int J Cancer 117: 41-50 (2005). Interestingly, the LG4-5 modules of the G domain of LAMA4 homologue LAMA3 have been reported to be exclusively found in squamous cell carcinomas (SCC) but absent/processed in normal healthy tissue. Furthermore, the LG4-5 modules of the G domain of LAMA3 have been reported to be necessary for SCC tumor growth, as a polyclonal antibody has been reported to inhibit tumor growth in a SCC xenograft mouse model. See, e.g., Tran et al., Cancer Res. 68: 2885-2894 (2008). It was thus of great interest to determine (1) if LAMA4 is processed in a similar fashion in tumors and (2) whether an LG4-5-specific anti-LAMA4 antibody could be efficacious in LAMA4-positive tumors.

Monoclonal antibodies against the LG4-5 modules of the G domain of LAMA4 were generated as described in Materials and Methods. The specific binding between the monoclonal antibodies and the LG4-5 modules of the G domain of LAMA4 was confirmed by assessing the monoclonal antibodies' ability to stain LAMA4-fragment-displaying human embryonic kidney 293 cells by flow cytometry. Fluorescent signal was assessed via flow cytometric analyses and plotted as mean fluorescence intensity (MFI) as shown in FIG. 1. A LG1-3-specific LAMA4 antibody was able to bind 293 cells displaying LG1-5 and LG1-3, but not LG4-5 of the LAMA4 protein. Conversely, clones 6C12, 13G10, and 15F7 were able to specifically bind 293 cells displaying LG1-5 and LG4-5, but not LG1-3.

Figure 2A:
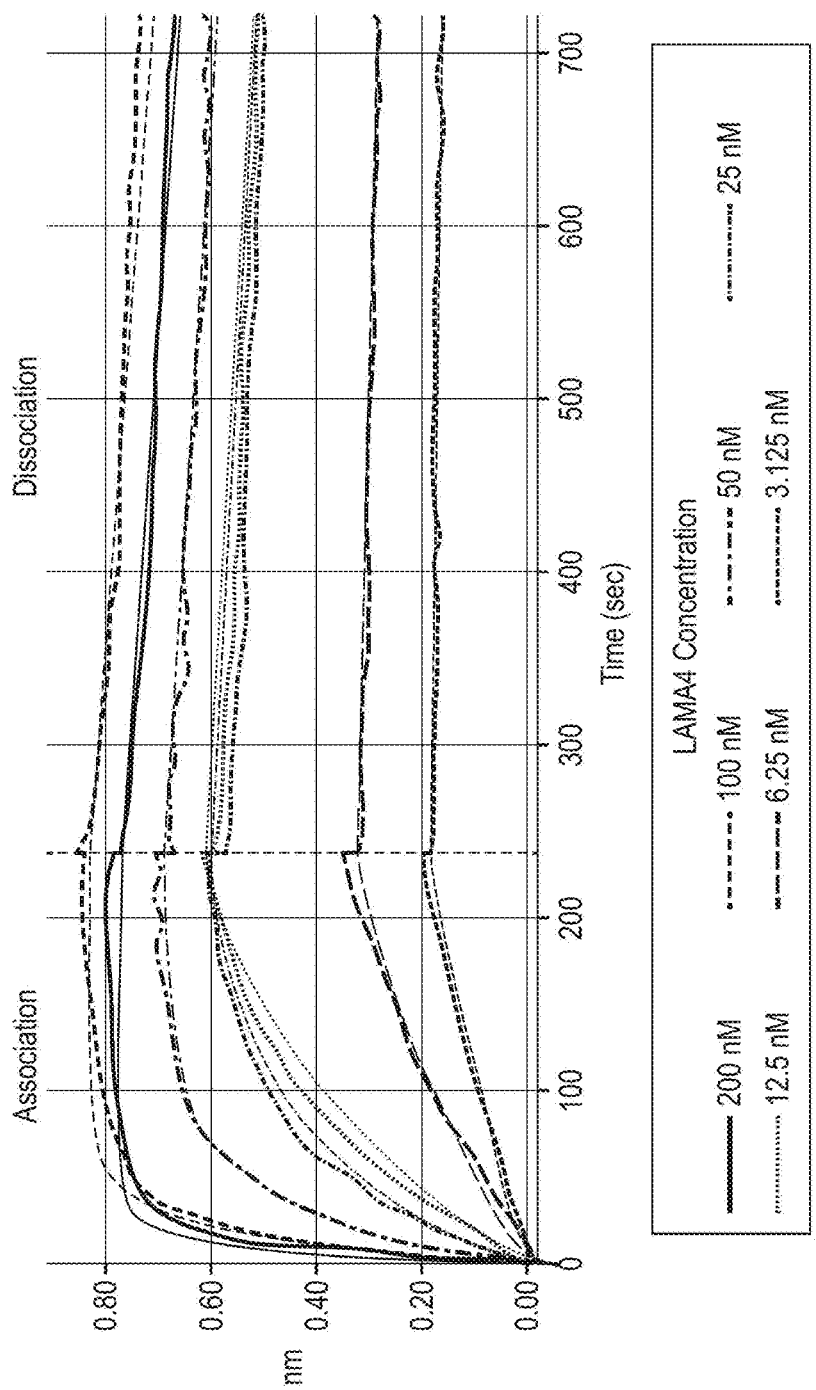
FIG. 2A-C show relative binding and on/off rates for the 15F7, 6C12, and 13G10 antibodies, respectively, as assessed by ForteBio.
Figure 2B:
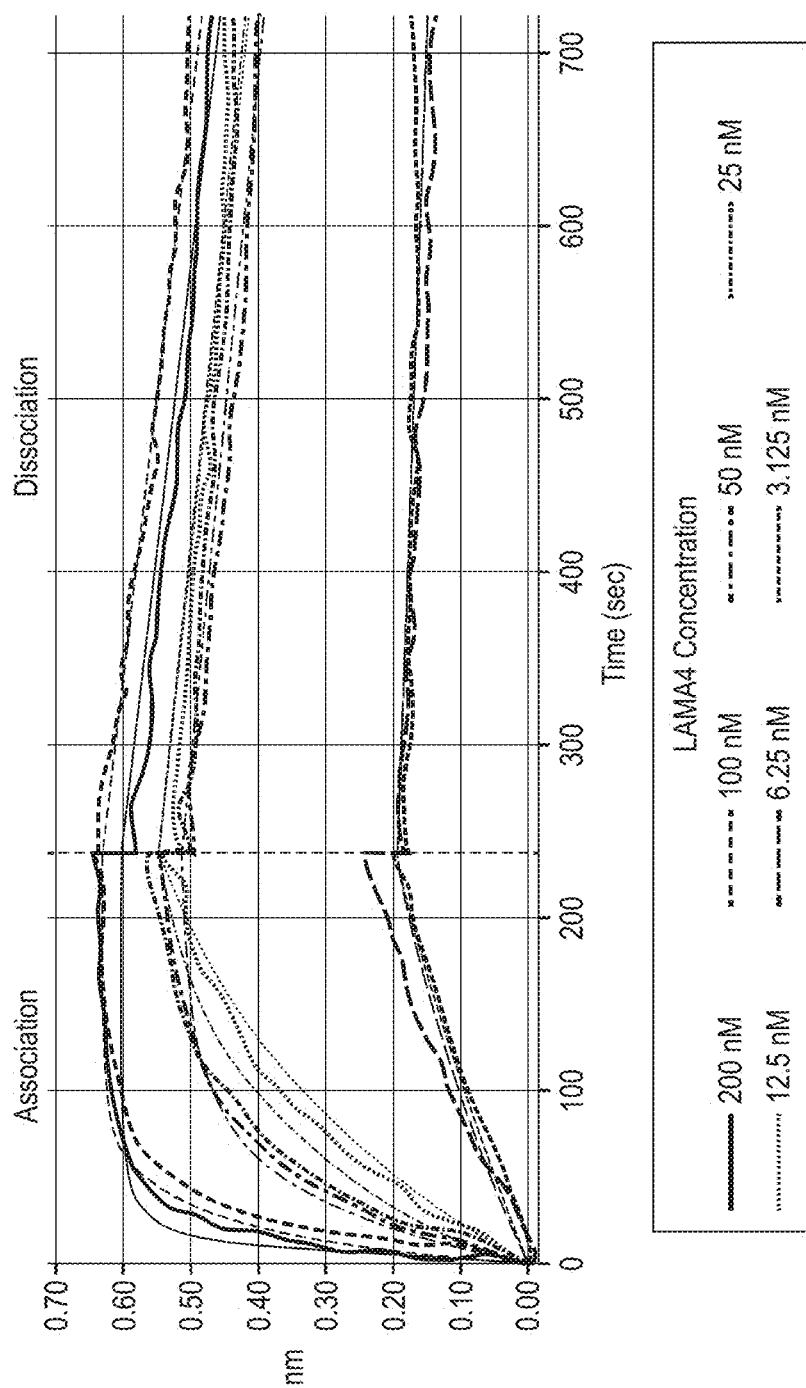
Figure 2C:
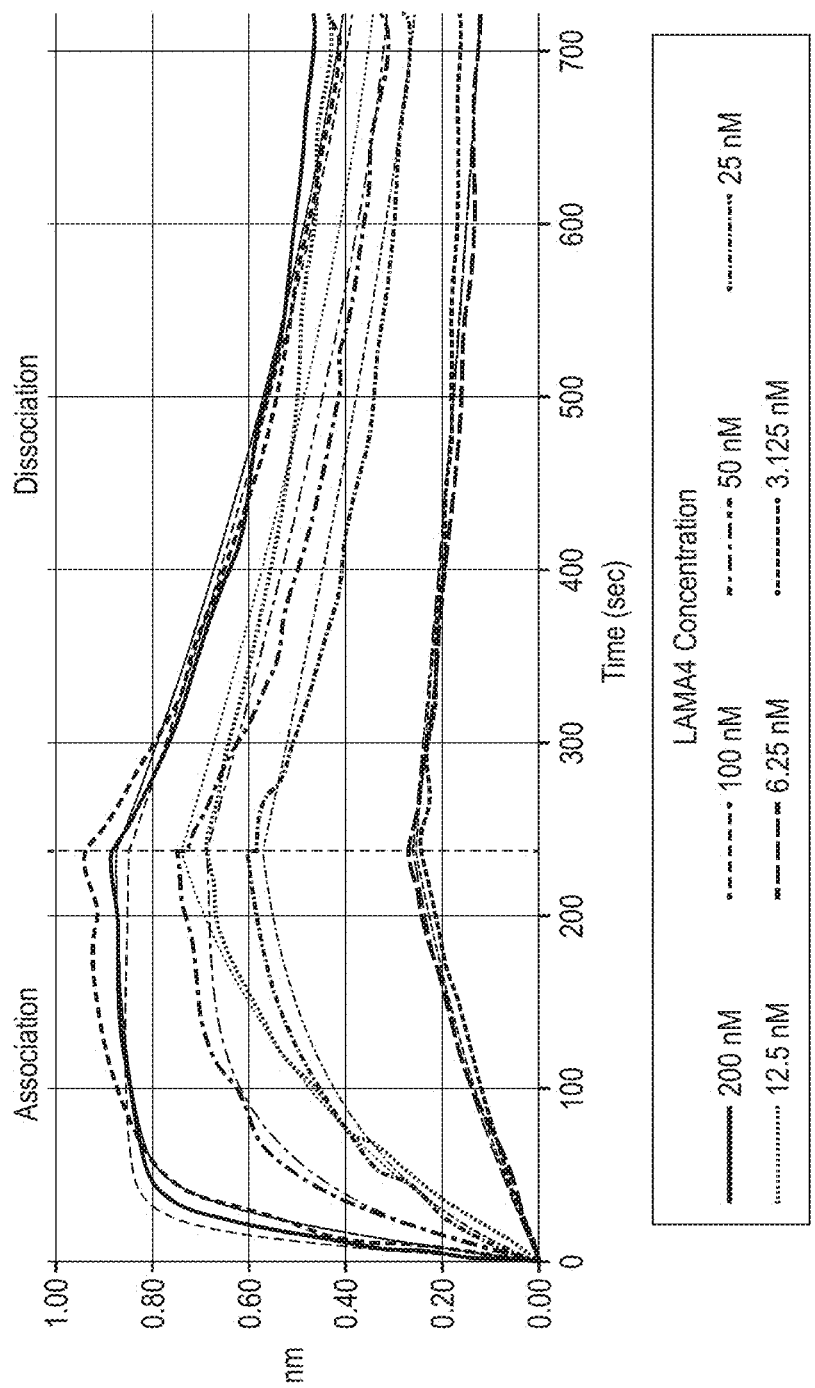

Relative binding and on/off rates for the 15F7, 6C12, and 13G10 antibodies were analyzed by ForteBio as shown in FIG. 2A-C, respectively. Antibody concentrations were kept constant at 100 nM, and the concentration of LAMA4 was varied as indicated in FIG. 2A-C. For each concentration of LAMA4, two lines are presented in FIG. 2A-C: a bolded line representing the raw data and a non-bolded line representing the statistical fitting of the raw data. Detailed binding kinetic parameters (association rate (1c), dissociation rate ($k_d$), and binding affinity constant ($K_D$)) were determined by Biacore for 13G10, 15F7, and 6C12, as shown in Table 1. The 15F7 antibody displayed the highest binding magnitude and slowest off rates in the ForteBio and Biacore assays.

TABLE 1

Biacore Assay Comparing Binding of 15F7, 13G10, and 6C12 to LAMA4

| Antibody | Human LAMA4 | | | Murine LAMA4 | | |
|---|---|---|---|---|---|---|
| | $k_a$ (M$^{-1}$s$^{-1}$) | $k_d$ (s$^{-1}$) | $K_D$ (M) | $k_a$ (M$^{-1}$s$^{-1}$) | $k_d$ (s$^{-1}$) | $K_D$ (M) |
| 13G10 | $3.02 \times 10^5$ | $7.4 \times 10^{-3}$ | $2.44 \times 10^{-8}$ | $3.78 \times 10^5$ | $4.49 \times 10^{-3}$ | $1.19 \times 10^{-8}$ |
| 15F7 | $1.14 \times 10^6$ | $7.81 \times 10^{-4}$ | $6.84 \times 10^{-10}$ | $1.05 \times 10^6$ | $6.58 \times 10^{-4}$ | $6.27 \; 10^{-10}$ |
| 6C12 | $3.28 \times 10^5$ | $1.02 \times 10^{-3}$ | $3.11 \times 10^{-9}$ | $4.69 \times 10^5$ | $1.11 \times 10^{-3}$ | $2.38 \times 10^{-9}$ |

Figure 3:
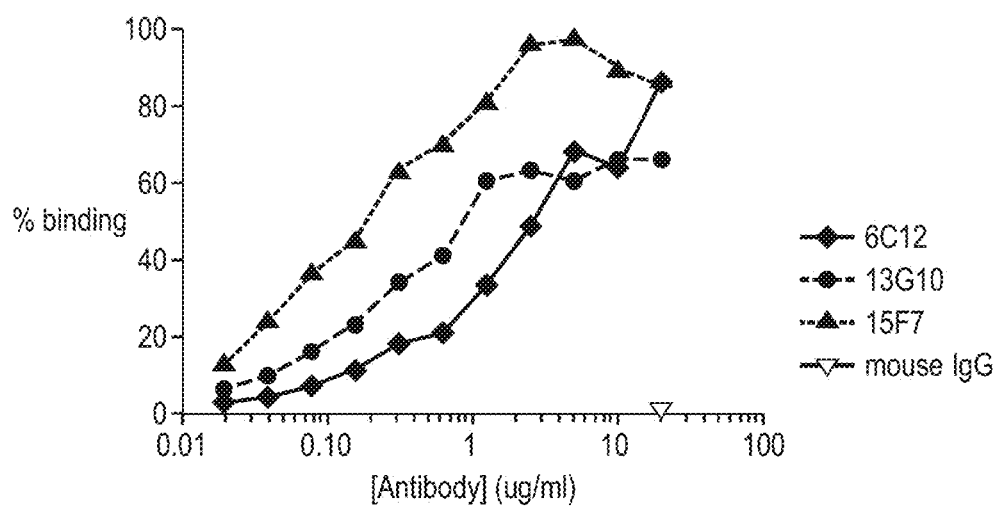
FIG. 3 shows the capacity of serially diluted 6C12, 13G10 and 15F7 antibodies to bind to LAMA4-displaying 293 cells as assessed by flow cytometry.

The 6C12, 13G10, and 15F7 antibodies, along with mouse IgG control, were tested for their ability to bind LAMA4-displaying cells. To test LAMA4 binding capacity, serially diluted antibodies were pre-incubated with LAMA4-displaying human 293 cells, followed by anti-human-650 secondary antibody incubation as described in the Materials and Methods. Binding capacity was assessed by flow cytometry as shown in FIG. 3. 15F7 again displayed the highest binding magnitude.

Figure 4A:
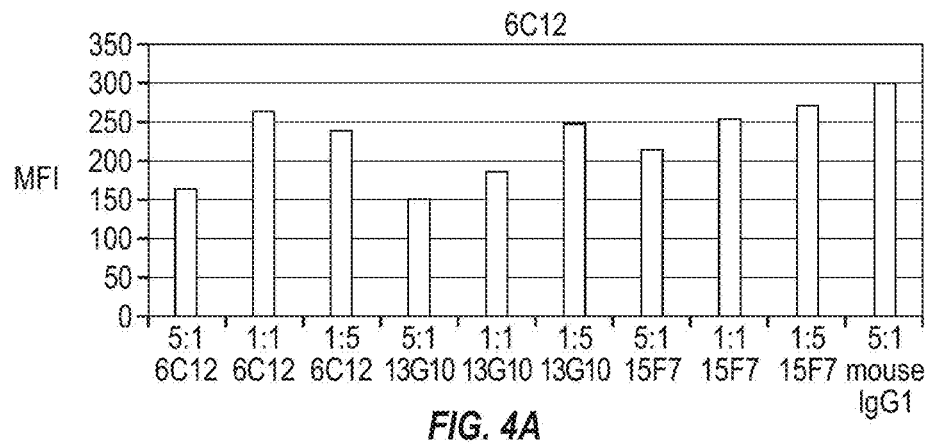
FIG. 4A-C show assessment of binding by FACS analysis of the 6C12, 13G10, and 15F7 antibodies, respectively, to LAMA4-displaying 293 cells in the presence of decreasing ratios (5:1, 1:1, and 1:5) of competing blocking antibodies.
Figure 4B:
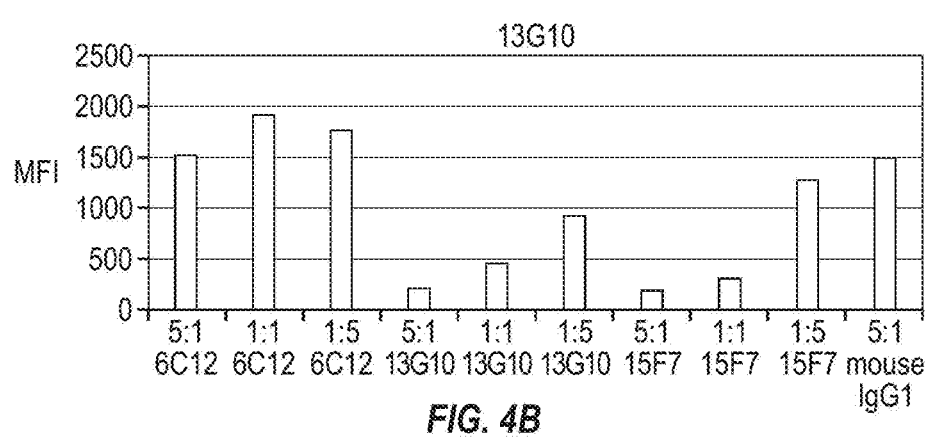
Figure 4C:
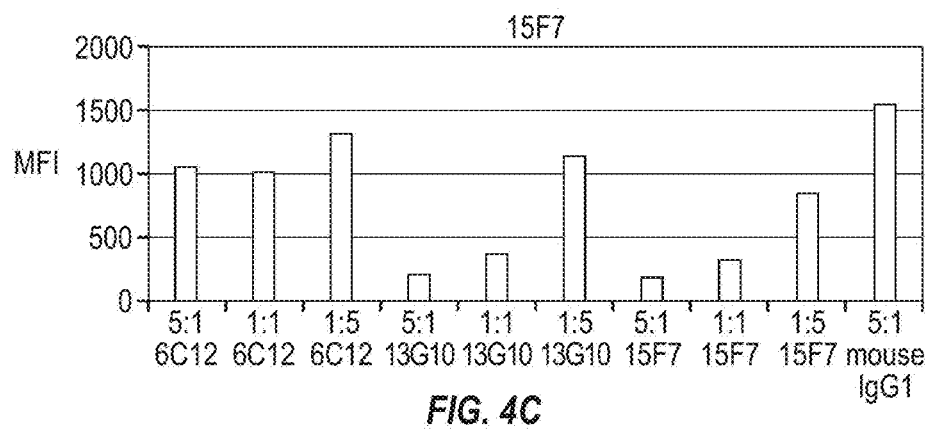

Competition experiments were carried out to differentiate the 6C12, 13G10, and 15F7 antibodies by epitope binding. Binding of the antibodies to LAMA4-displaying 293 cells was assessed using decreasing ratios (5:1, 1:1, and 1:5) of blocking antibody to binding antibody, with mouse IgG1 being used as a negative control. Binding of the 6C12, 13G10, and 15F7 antibodies was assessed by flow cytometery as shown in FIG. 4A-C, respectively. Fluorescent signal was assessed via flow cytometric analyses and plotted as mean fluorescence intensity (MFI). All three antibodies were able to compete with each other for LG4-5 binding, with each being having higher blocking efficacy at the 5:1 ratio ((blocking antibody):(binding antibody)) and lower blocking efficacies as the ratio decreases. These results indicate that these antibodies all bind similar epitopes on the LAMA4 protein.

Example 2. LG4-5-Domain-Specific Anti-LAMA4 Monoclonal Antibody Exclusively Stains Human and Mouse Melanoma Tissue To determine whether the LG4-5 modules of the G domain of LAMA4 are exclusively found in tumor tissue, WM-266-4 human melanoma cells were tested for LAMA4 expression with polyclonal anti-LAMA4 antibodies. Staining was undertaken for both MCAM and LAMA4. MCAM-positive WM-266-4 cells were positive for LAMA4 expression.

WM-266-4 tumors were implanted subcutaneously in nude mice and allowed to grow for five weeks. Following transcardiac perfusion with PBS, tumors and healthy tissue were frozen, sectioned, and stained with mouse IgG control, LG1-3-specific, and LG4-5-specific monoclonal antibodies 6C12, 13G10, and 15F7 as described in Materials and Methods. LG1-3-specific and LG4-5-specific antibodies were both able to stain WM-266-4 subcutaneous tumors and vasculature.

Additional subcutaneous tumor experiments were performed using a mouse melanoma cell line, B16. B16 mouse melanoma cells were subcutaneously injected or intravenously injected into mice and allowed to metastasize to the lungs. Staining of B16 tumor tissue and healthy mouse brain, liver, kidney, and lung tissues was undertaken with a LG1-3-specific antibody, with mouse IgG1 used as a control. The LG1-3-specific antibody was able to robustly stain all tissue types tested. Staining of B16 tumor tissue and healthy mouse brain, liver, kidney, and lung tissues was also undertaken with the LG4-5-specific antibodies, 6C12, 13G10, and 15F7. In contrast to the LG1-3-specific antibody, these three LG4-5-specific antibodies exclusively stained the B16 tumor vasculature in the primary subcutaneous tumors and were not able to robustly stain any of the healthy tissues. Staining of a sample containing B16 lung metastatic foci and healthy adjacent lung tissue was undertaken with the LG1-3-specific antibody, the LG4-5-specific antibodies (6C12, 13G10, and 15F7), and a control mouse IgG1. The LG1-3-specific antibody was able to robustly stain both the metastatic foci and the healthy adjacent tissue. In contrast, the 6C12, 13G10, and 15F7 antibodies were not able to stain the healthy adjacent lung tissue and exclusively stained B16 tumor vasculature in metastatic foci.

Samples of healthy human skin and skin melanoma from two distinct patients were stained with a LG4-5-specific antibody, 15F7. Consistent with the staining results described above, 15F7 was able to stain both skin melanoma samples but was unable to stain the healthy skin tissue.

Figure 5C:
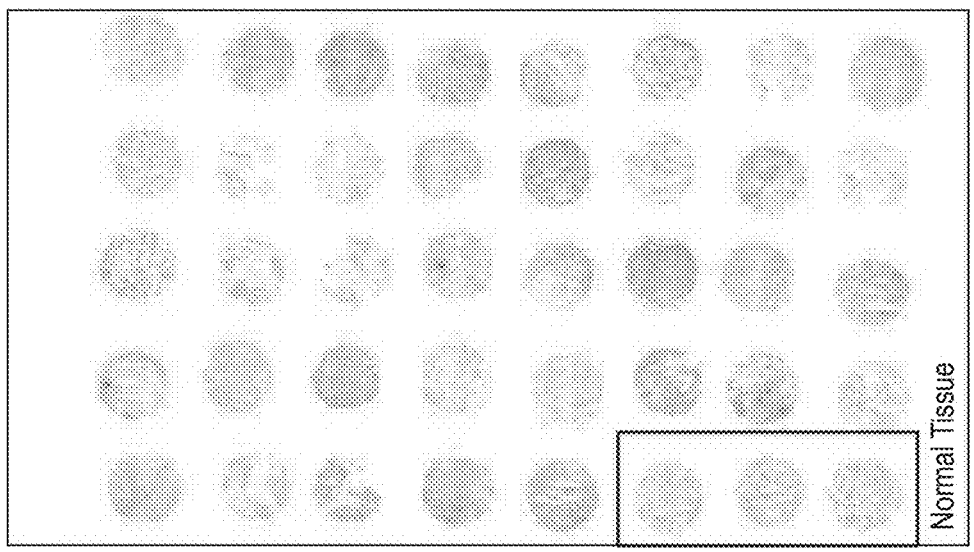
FIG. 5A-C show staining of tumor microarray slides for human breast, colon, and lung tumors, respectively, with the 15F7 antibody.
Figure 5B:
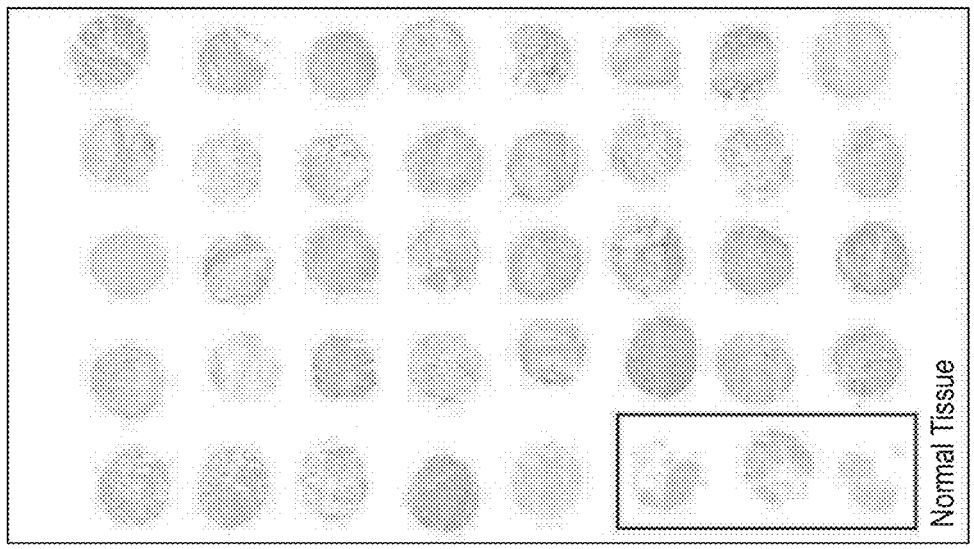
Figure 5A:
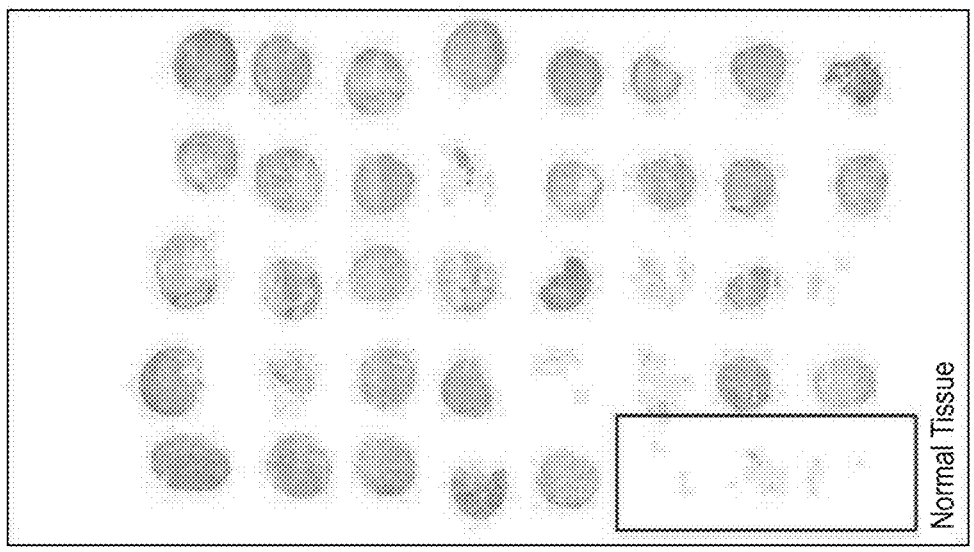

Other human tumor types were stained as well. As shown in FIG. 5A-C, a LG-4-5-specific antibody, 15F7, was used to stain tumor microarray slides for human breast, colon, and lung tumors, respectively. Normal tissue controls are enclosed in the white rectangles. Consistent with the staining of the melanomas described above, 15F7 preferentially stained the majority of tumor patient samples in the tumor microarray slides for human breast, colon, and lung cancers. These results are consistent with a model whereby the LG4-5 modules of the G domain of LAMA4 are exclusively found in various human and mouse tumor types, indicating that the LG4-5 modules of the G domain of LAMA4 can be a tumor-specific marker for diagnostics and targeted tumor therapeutics.

Figure 6:
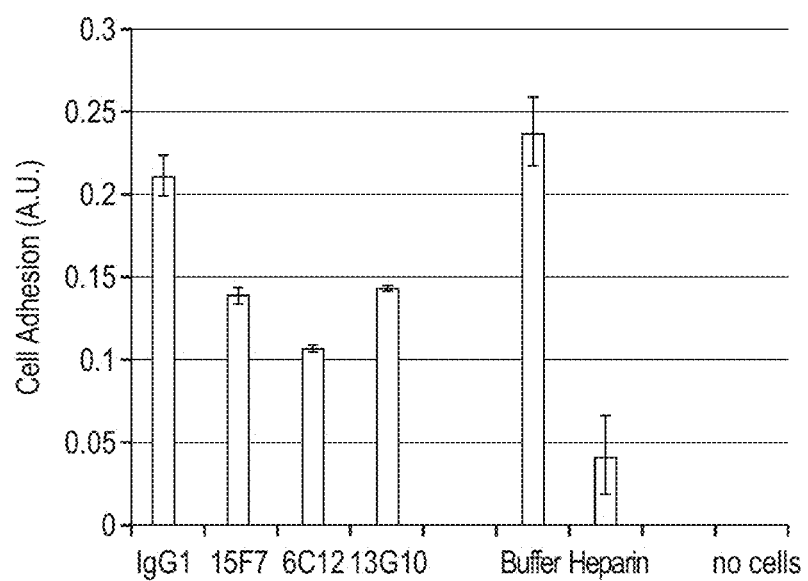
FIG. 6 shows a cell adhesion assay in which recombinant LG4-5-coated ELISA plates were incubated with 20 ug/ml 15F7, 6C12, 13G10, and mouse IgG1 control and then assayed for their ability to bind to WM-266-4 human melanoma cells.

Example 3. LG4-5-Domain-Specific Anti-LAMA4 Monoclonal Antibody Inhibits Human Melanoma Cell Adhesion and Drives Antibody-Drug Conjugate Cell Toxicity To determine the functional consequences of targeting the LG4-5 modules of the G domain of LAMA4 with anti-LG4-5 antibodies, recombinant LG4-5-coated ELISA plates were incubated with 20 ug/ml 15F7, 6C12, and 13G10 (or mouse IgG1 control) and were then assayed for their ability to bind human melanoma cell line WM-266-4 as described in Materials and Methods. Buffer was used as a negative control and heparin was used as a positive control. A sample with no cells was used as an additional negative control. The results of the cell adhesion assay are shown in FIG. 6. The results are presented in arbitrary units (A.U.) on the y-axis. Although mouse IgG1 control failed to block LAMA4-mediated cell adhesion, all three anti-LG4-5 antibodies were able to inhibit LAMA4-mediated human melanoma cell adhesion by approximately 35% or greater, indicating that anti-LG4-5 antibodies can block cell adhesion events necessary for tumor cell adhesion, proliferation, and metastasis.

Figure 7:
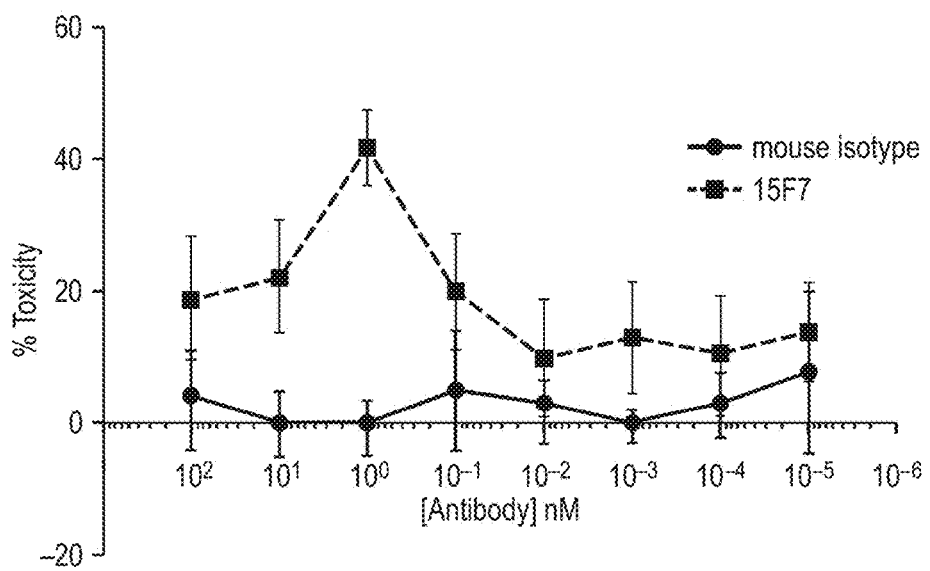
FIG. 7 shows toxicity to WM-266-4 cells when incubated with the 15F7 antibody and a saporin-conjugated anti-mouse secondary antibody.

Because the LG4-5 domain of LAMA4 is highly enriched in various human tumor tissues when compared to healthy human tissue, we tested anti-LG4-5 antibodies as candidates for antibody-drug conjugate targeting strategies. As shown in FIG. 7, LAMA4+WM-266-4 cells were incubated with the 15F7 anti-LG4-5 antibody or a mouse isotype control along with ribosomal toxin saporin-conjugated anti-mouse secondary. Although LAMA4 LG4-5 is a soluble extracellular matrix protein, 15F7 was able to strongly mediate saporin-mediated cell toxicity.

These data indicate that anti-LG4-5 antibodies block WM-266-4 human melanoma cell adhesion and are strong candidates for antibody-drug conjugate therapeutic approaches. Targeting LG4-5 could be efficacious in slowing tumor growth and metastasis.

Example 4. Design of Humanized 15F7 Antibodies

The starting point or donor antibody for humanization was the mouse antibody 15F7. The heavy chain variable amino acid sequence of mature m15F7 is provided as SEQ ID NO:16. The light chain variable amino acid sequence of mature m15F7 is provided as SEQ ID NO:17. The heavy chain CDR1, CDR2, and CDR3 amino acid sequences are provided as SEQ ID NOS:20, 21, and 22, respectively (as defined by Kabat). The light chain CDR1, CDR2, and CDR3 amino acid sequences are provided as SEQ ID NOS:23, 24, and 25, respectively (as defined by Kabat). Kabat numbering is used throughout in this Example.

The variable kappa (Vk) of m15F7 belongs to mouse Kabat subgroup 5, which corresponds to human Kabat subgroup 1. The variable heavy (Vh) of m15F7 belongs to mouse Kabat subgroup 5a, which corresponds to Kabat subgroup 1. See Kabat et al. Sequences of Proteins of Immunological Interest, Fifth Edition. NIH Publication No. 91-3242, 1991. The 11-residue CDR-L1 belongs to canonical class 1, the 7-residue CDR-L2 belongs to canonical class1, and the 9-residue CDR-L3 belongs to canonical class 1 in Vk. See Martin & Thornton, J. Mol. Biol. 263:800-15, 1996. The 5-residue CDR-H1 (as defined by Kabat) belongs to canonical class 1, and the 17-residue CDR-H2 belongs to canonical class 1. See Martin & Thornton, J Mol. Biol. 263:800-15, 1996. The CDR-H3 has no canonical classes, but the 10-residue loop probably has a kinked base according to the rules of Shirai et al., FEBS Lett. 455:188-97 (1999).

The residues at the interface between the Vk and Vh domains are usual.

A search was made over the protein sequences in the PDB database (Deshpande et al., Nucleic Acids Res. 33: D233-7, 2005) to find structures which would provide a rough structural model of 15F7. The crystal structure of the antibody against monocyte chemoattractant proteins (MCPs) was used for Vk structure. It retains the same canonical structure for the loop as 15F7 (pdb code 2BDN, resolution 2.53A). The heavy chain of the antibody against LeuT mutants (pdb code 3TT1, resolution 3.1A) was used for Vh structure. It contains the same canonical structures for CDR-H1 and CDR-H2 as that of 15F7 VH, and also the same length CDR-H3 with a kinked base. BioLuminate was used to model a rough structure of 15F7 Fv.

A search of the non-redundant protein sequence database from NCBI with CDR"X"ed 15F7 Fv allowed selection of suitable human frameworks into which to graft the murine CDRs. For Vh, two human Ig heavy chains, ACF36857.1 and BAC01530.1 (SEQ ID NOS:96 and 97, respectively) were chosen. They share the canonical form of 15F7 CDR-H1 and H2, and H3 of BAC01530.1 is 10 residues long with a predicted kinked base. For Vk, two human kappa light chains, having NCBI accession codes AAY33350.1 and BAC01583.1 (SEQ ID NOS:53 and 98, respectively), were chosen. They have the same canonical classes for CDR-L1, L2, and L3 as that for the parental Vk. Humanized 15F7 heavy and light chain variable region sequences having no backmutations or other mutations are provided as SEQ ID NOS:55 and 56.

Two humanized heavy chain variable region variants and two humanized light chain variable region variants were constructed containing different permutations of substitutions (Hu15F7VHv1-2 (SEQ ID NOS:57 and 58, respectively) and Hu15F7VLv1-2 (SEQ ID NOS:59 and 60, respectively)) (FIGS. 12A-D, FIGS. 13A-D). The exemplary humanized Vh and Vk designs, with backmutations and other mutations based on selected human frameworks, are shown in FIGS. 12A-D and FIGS. 13A-D, respectively. The gray-shaded areas in the first column in FIGS. 12A-D and FIGS. 13A-D indicate the CDRs as defined by Chothia, and the gray-shaded areas in the remaining columns in FIGS. 12A-D and FIGS. 13A-D indicate the CDRs as defined by Kabat. SEQ ID NOS:57-60 contain backmutations and other mutations as shown in Table 2. The amino acids at positions H1, H20, H27, H30, H38, H40, H41, H48, H66, H67, H69, H75, H82A, H91, L8, L42, L45, L49, L69, and L80 in Hu15F7VHv1-2 and Hu15F7VLv1-2 are listed in Table 3. The amino acids at position L104 in Hu15F7VLv1-2 are also listed in Table 3.

TABLE 2

$V_H$, $V_L$ Backmutations and Other Mutations

| $V_L$ Variant | $V_L$ Exon Acceptor Sequence | Donor Framework Residues |
| --- | --- | --- |
| Hu15F7VLv1 (SEQ ID NO: 59) | NCBI accession codes AAY33350.1 and BAC01583.1 (SEQ ID NOS: 53 and 98) | L8, L42, L45, L49, L69, L80 |
| Hu15F7VLv2 (SEQ ID NO: 60) | NCBI accession codes AAY33350.1 and BAC01583.1 (SEQ ID NOS: 53 and 98) | L42, L49, L69, L104 |
| Hu15F7VHv1 (SEQ ID NO: 57) | NCBI accession codes ACF36857.1 and BAC01530.1 (SEQ ID NOS: 96 and 97) | H1, H20, H27, H30, H38, H40, H41, H48, H66, H67, H69, H75, H82A, H91 |
| Hu15F7VHv2 (SEQ ID NO: 58) | NCBI accession codes ACF36857.1 and BAC01530.1 (SEQ ID NOS: 96 and 97) | H1, H20, H27, H30, H38, H40, H48, H66, H67, H75, H82A, H91 |

TABLE 3

Kabat Numbering of Framework Residues for Backmutations and Other Mutations in Humanized 15F7 Antibodies

| Residue | AAY33350.1 light chain | BAC01583.1 light chain | ACF36857.1 heavy chain | BAC01530.1 heavy chain | Mouse 15F7 | Hu15F 7VL1 | Hu15F 7VL2 | Hu15F 7VH1 | Hu15F 7VH2 |
| --- | --- | --- | --- | --- | --- | --- | --- | --- | --- |
| L8 | P | P | — | — | S | S | P | — | — |
| L42 | K | K | — | — | N | N | N | — | — |
| L45 | K | K | — | — | R | R | K | — | — |
| L49 | Y | Y | — | — | S | S | S | — | — |
| L69 | T | T | — | — | K | K | K | — | — |
| L80 | P | P | — | — | T | T | P | — | — |
| L104 | L | L | — | — | L | L | V | — | — |
| H1 | — | — | Q | Q | Q | — | — | E | E |
| H20 | — | — | V | V | L | — | — | L | L |
| H27 | — | — | G | G | Y | — | — | Y | Y |
| H30 | — | — | S | S | T | — | — | T | T |
| H38 | — | — | R | R | K | — | — | K | K |
| H40 | — | — | A | A | R | — | — | R | R |
| H41 | — | — | P | P | A | — | — | A | P |
| H48 | — | — | M | M | I | — | — | I | I |
| H66 | — | — | R | R | K | — | — | K | K |
| H67 | — | — | V | V | A | — | — | A | A |
| H69 | — | — | I | I | L | — | — | L | I |
| H75 | — | — | T | T | S | — | — | S | S |
| H82A | — | — | S | S | R | — | — | R | R |
| H91 | — | — | Y | Y | F | — | — | F | F |

The rationales for selection of the above positions in the light chain variable region as candidates for substitution are as follows.

P8S: P is more frequent than S in the human IgG framework, but because proline cis-trans isomerization affects protein folding, P was tried in one version and S in the other version.

K42N: N contacts interface residue F91 in VH and is therefore critical for maintaining antibody structure.

K45R: R and K have similar frequency in the human IgG framework, so R was tried in one version and K in the other version.

Y49S: S contacts LCDR2 and is critical.

T69K: K contacts LCDR1 and is critical.

P80T: P is more frequent than T in the human IgG framework, but because proline cis-trans isomerization affects protein folding, P was tried in one version and T was tried in the other version.

L104V: L was tried in one version, and V was tried in the other version.

The rationales for selection of the above positions in the heavy chain variable region as candidates for substitution are as follows.

Q1E: This is a mutation but not a backmutation. Glutamate (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control.

V20L: L is more frequent than V in the human IgG framework.

G27Y: This residue is within HCDR1 as defined by Chothia, so Y was used to maintain binding ability.

S30T: This residue is within HCDR1 as defined by Chothia, so T was used to maintain binding ability.

R38K: K contacts two interface residues, L45 and W47, in VH and is therefore critical.

A40R: R is located at the end of the KQRAGQG (VH amino acids 38-44) loop, which supports the two interface residues, V37 and L45 in VH. It is important for maintaining antibody folding.

P41A: P is more frequent than A in the human IgG framework, but introduction of P into the framework may cause some conformational changes, so P was tried in one version and A was tried in the other version.

M48I: I contacts HCDR2 and interface residues V37 and L45 in VH.

R66K: K contacts HCDR2.

V67A: A contacts HCDR2.

I69L: I is more frequent than L in the human IgG framework, but L contacts HCDR1 and HCDR2, so I was tried in one version and L was tried in the other version.

T75S: Both T and S are frequent in the human framework.

S(82A)R: R contacts HCDR2 and is critical.

Y91F: F is an interface residue and is important to support antibody folding.

The two humanized light chain variable region variants and two humanized heavy chain variable region variants are as follows:

Hu15F7VL version 1 (P8S, K42N, K45R, Y49S, T69K, and P80T backmutations in lowercase):

(SEQ ID NO: 59)
DIQMTQSsSSLSASVGDRVTITCKASEDIYNRLAWYQQKPGnAPrLLIs

GATSLETGVPSRFSGSGSGkDYTLTISSLQtEDFATYYCQQYWSIPYTF

GGGTKLEIKR.

Hu15F7VL version 2 (K42N, Y49S, and T69K backmutations and L104V mutation in lowercase):

(SEQ ID NO: 60)
DIQMTQSPSSLSASVGDRVTITCKASEDIYNRLAWYQQKPGnAPKLLIs

GATSLETGVPSRFSGSGSGkDFTLTISSLQPEDFATYYCQQYWSIPYTF

GGGTKvEIKR.

Hu15F7VH version 1 (Q1E mutation and V20L, G27Y, S30T, R38K, A40R, P41A, M48I, R66K, V67A, I69L, T75S, S(82A)R, and Y91F backmutations in lowercase):

(SEQ ID NO: 57)
eVQLQQSGAEVKKPGSSVKlSCKASGyTFtSYGLSWVkQraGQGLEWiG

EIFPRSGNTYYNEKFKGkaTlTADKSsSTAYMELrSLRSEDTAVYfCAR

GVRSPGAMDYWGQGTLVTVSS.

Hu15F7VH version 2 (Q1E mutation and V20L, G27Y, S30T, R38K, A40R, M48I, R66K, V67A, T75S, S(82A)R, and Y91F backmutations in lowercase):

(SEQ ID NO: 58)
eVQLQQSGAEVKKPGSSVKlSCKASGyTFtSYGLSWVkQrPGQGLEWiG

EIFPRSGNTYYNEKFKGkaTITADKSsSTAYMELISLRSEDTAVYfCAR

GVRSPGAMDYWGQGTLVTVSS.

Example 5. Binding Kinetic Analysis of Humanized 15F7 Antibodies

Binding kinetics of humanized 15F7 antibodies comprising a heavy chain selected from Hu15F7VHv1-2 (H1 and H2) and a light chain selected from Hu15F7VLv1-2 (L1 and L2) were characterized.

Chimeric 15F7, H1L1, H1L2, H2L1, H2L2, and buffer alone were tested for their ability to bind to LAMA4-fragment-displaying cells. To test LAMA4 binding capacity, serially diluted antibodies were pre-incubated with human 293 cells displaying LG4-5, followed by anti-human-650 secondary antibody incubation as described in the Materials and Methods. Fluorescent signal was assessed via flow cytometric analyses and plotted as mean fluorescence intensity (MFI) as shown in FIG. 8. The serially diluted H1L1, H1L2, H2L1, and H2L2 antibodies each showed binding capacity that is comparable to chimeric 15F7.

Figure 9:
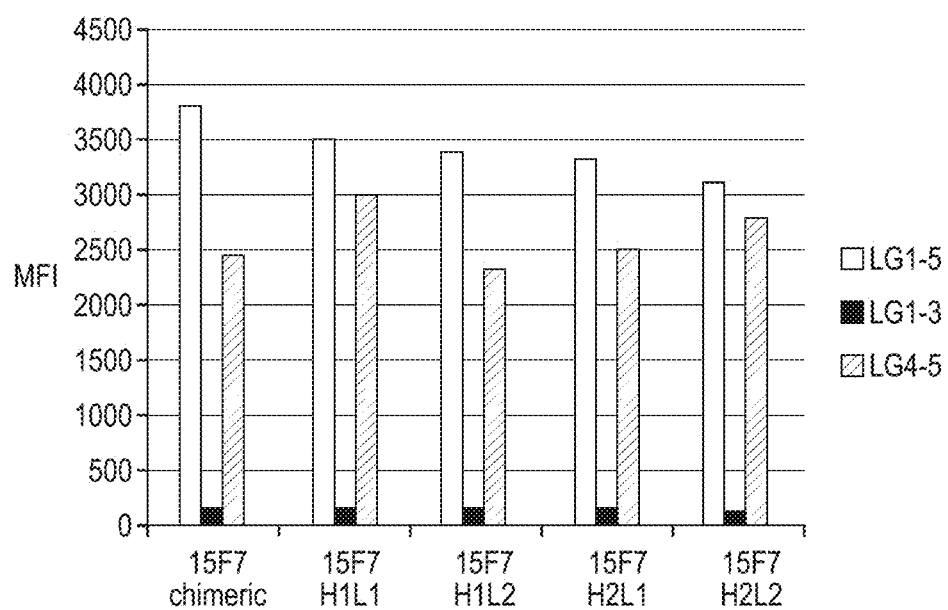
FIG. 9 shows binding as assessed by flow cytometry of chimeric 15F7 and humanized 15F7 variants H1L1, H1L2, H2L1, and H2L2 to 293 cells displaying LAMA4 fragments containing LG1-5, LG1-3, and LG4-5.

The specific binding of the chimeric 15F7, H1L1, H1L2, H2L1, and H2L2 antibodies to the LG4-5 modules of the G domain of LAMA4 was tested by assessing the antibodies' ability to stain LAMA4-fragment-displaying 293 cells by flow cytometry, as shown in FIG. 9. Each of the antibodies was able to specifically bind 293 cells displaying LG1-5 and LG4-5, but not LG1-3.

Figure 10A:
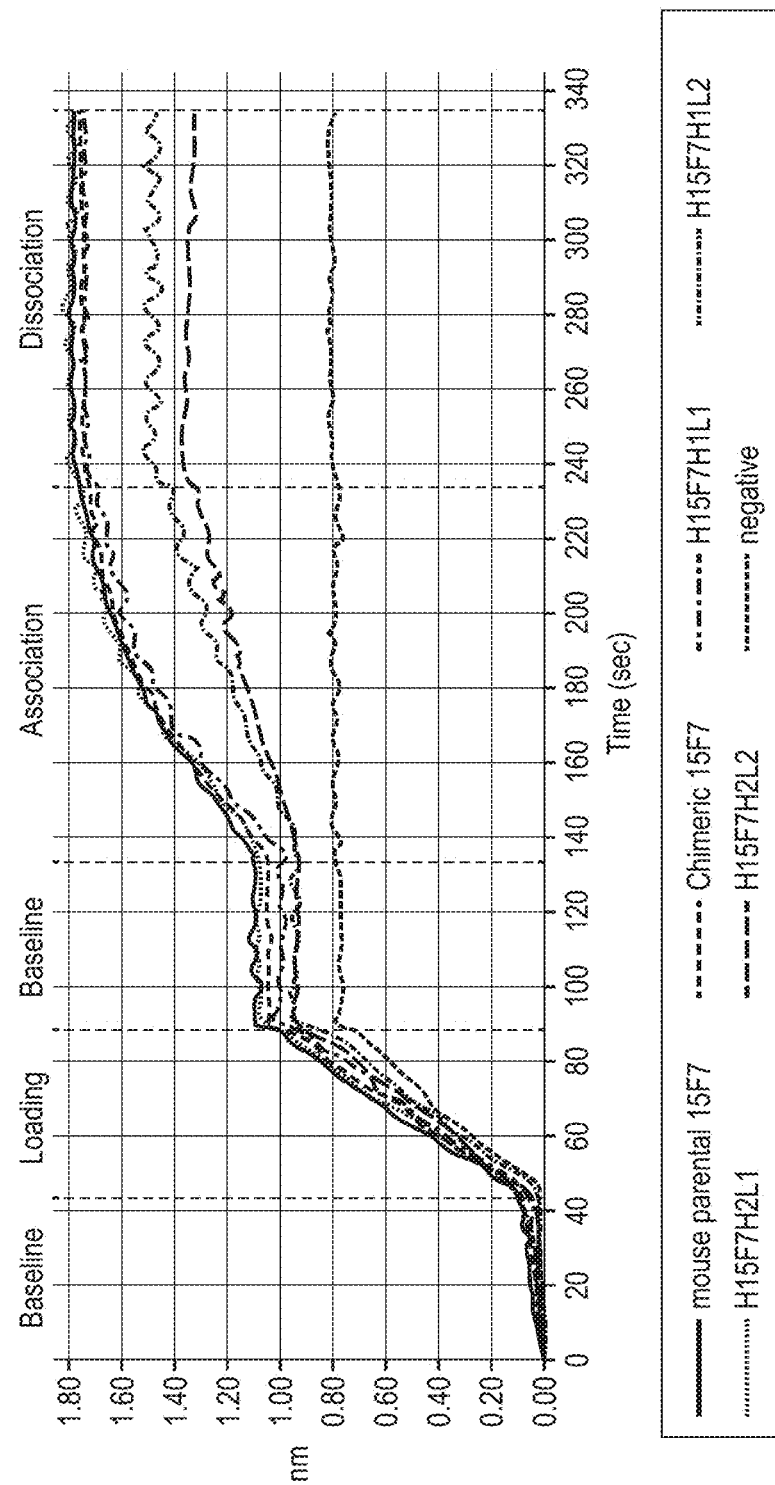
FIG. 10A-B show relative binding and on/off rates for m15F7, chimeric 15F7 and humanized 15F7 variants H1L1, H1L2, H2L1, and H2L2 as assessed by ForteBio, with the anti-His sensor being loaded with His-LAMA4 followed by association and dissociation of the 15F7 antibodies in 10A, and the goat anti-human Fc sensor being loaded with the antibodies followed by association and dissociation of His-LAMA4 in 10B.
Figure 10B:
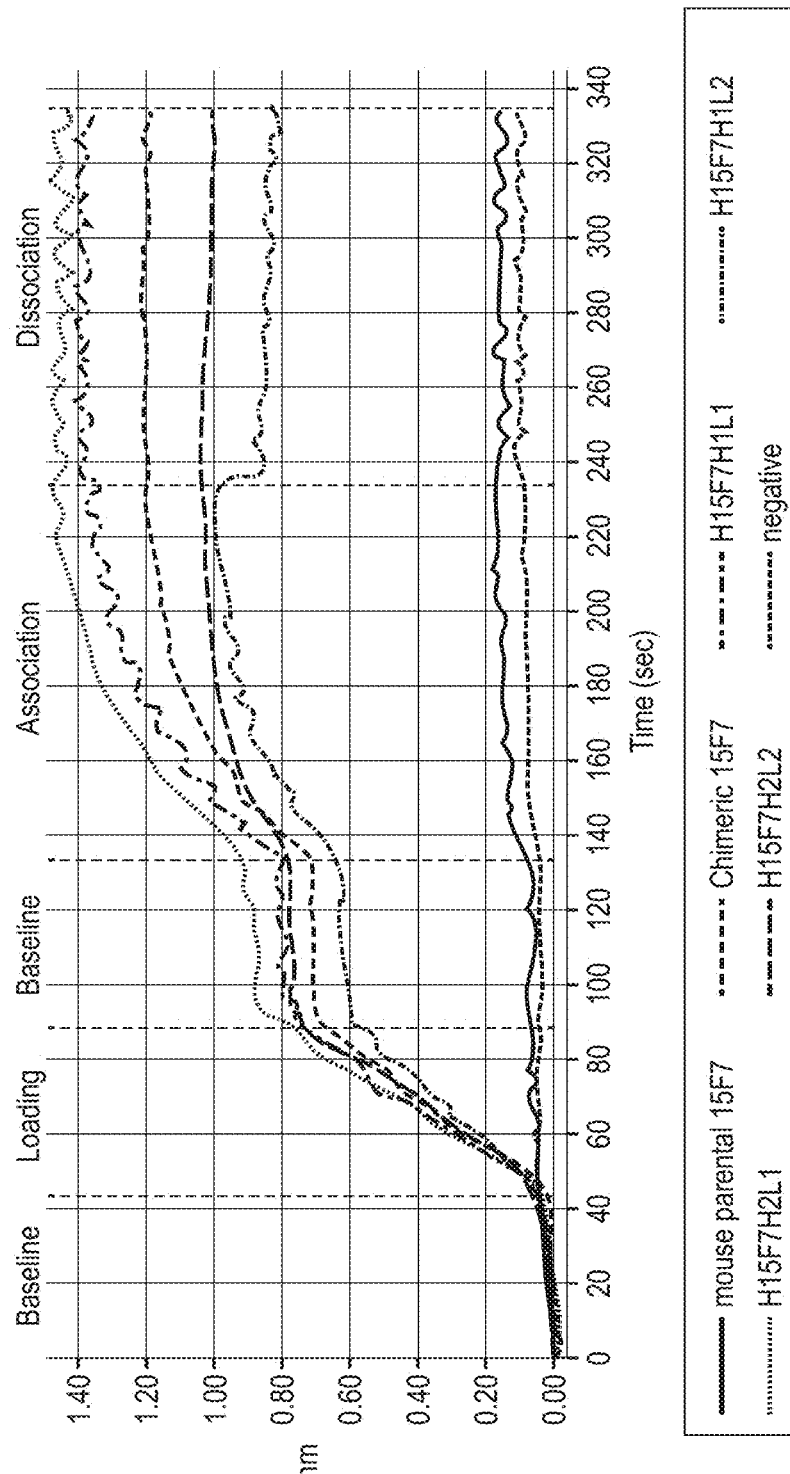

Relative binding and on/off rates were analyzed by ForteBio, as shown in FIGS. 10A and 10B. In FIG. 10A, the anti-His sensor was loaded with 10 ug/ml of purified His-LAMA4 followed by loading of 5 ug/ml of m15F7, chimeric 15F7, H1L1, H1L2, H2L1, and H2L2. Association and dissociation were analyzed. In FIG. 10B, the goat anti-human Fc sensor was loaded with m15F7, chimeric 15F7, H1L1, H1L2, H2L1, and H2L2 as indicated at 5 ug/ml followed by loading of 10 ug/ml of His-LAMA4. Association and dissociation were analyzed. Relative binding and on/off rates were comparable among all antibodies tested, with H1L1 and H2L1 displaying relative binding that was the same or higher than that for chimeric 15F7 and m15F7.

Biacore full binding kinetic analysis of antibodies was then carried out. SPR analysis was performed as described in the Materials and Methods. Detailed binding kinetic parameters (association rate ($k_{assoc}$), dissociation rate ($k_{dissoc}$), and binding affinity constant ($K_d$)) were determined for chimeric 15F7, humanized H1L1, and humanized H2L1. Binding kinetic parameters for the humanized 15F7 variants H1L1 and H2L1 were comparable to those for chimeric 15F7 (see Table 4).

TABLE 4

Biacore Assay Comparing Binding of HU15F7 Variants and Chimeric 15F7 to LAMA4

| Antibody | $k_{assoc}$ (M$^{-1}$s$^{-1}$) | $k_{dissoc}$ (s$^{-1}$) | $K_d$ (M) |
|---|---|---|---|
| Chimeric | $1.50 \times 10^6$ | $1.51 \times 10^{-4}$ | $1.0 \times 10^{-10}$ |
| H1L1 | $1.50 \times 10^6$ | $1.83 \times 10^{-4}$ | $1.2 \times 10^{-10}$ |
| H2L1 | $1.56 \times 10^6$ | $2.05 \times 10^{-4}$ | $1.3 \times 10^{-10}$ |

Example 6. Anti-Laminin Antibodies Inhibit Laminin-411-Induced pAkt Activation

Figure 11A:
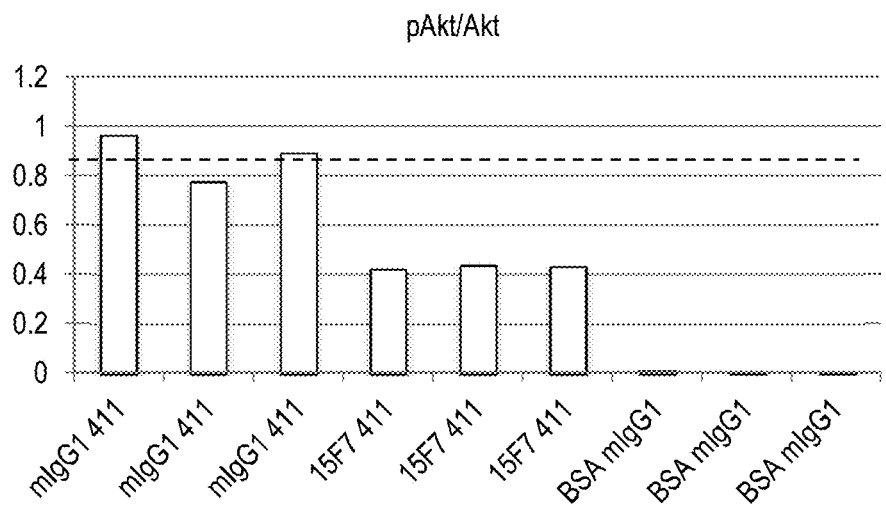
FIG. 11A-B show ratios of the relative levels of pAkt to Akt in human melanoma cells treated with laminin 411 or BSA control and with 15F7 or mIgG1 control.
Figure 11B:
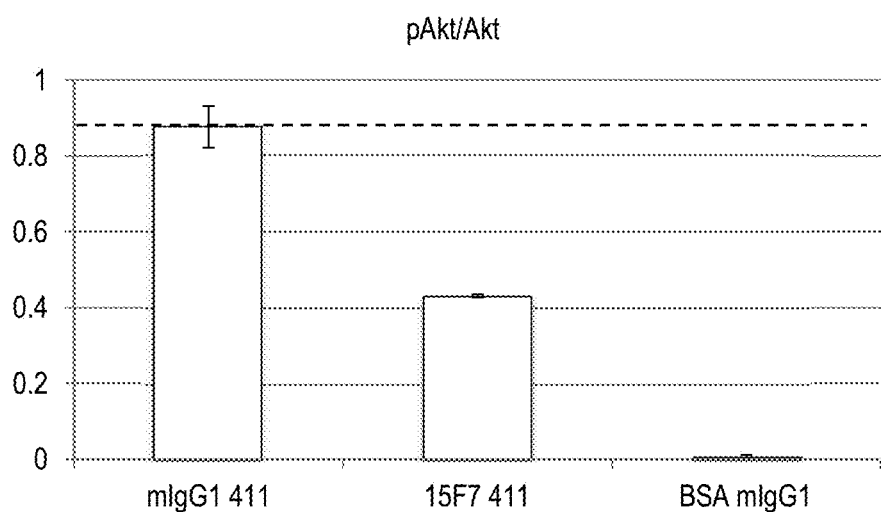

WM266.4 human tumor melanoma cells were serum-starved for 24 h and then resuspended into serum-free cell culture media with 10 ug/ml laminin 411 (LAMA4 in complex with gamma1 and beta1 chains) and 20 ug/ml 15F7 or mIgG1 control antibody for 30 minutes. BSA protein was used as a control for laminin 411. Cells were then spun down and lysed for immunoblot analyses. pAkt and total Akt levels were assessed by immunoblot. Ratios of these levels (pAkt/Akt) are shown in FIGS. 11A & B. Each condition (mIgG1+laminin 411; 15F7+laminin 411; and mIgG1+BSA) was tested in triplicate. FIG. 11A shows the results for each individual sample, and FIG. 11B shows the averages and standard errors for each condition. As shown in FIG. 11B, laminin 411 induced pAkt signaling (i.e., higher pAkt/Akt ratio) compared to BSA control, and 15F7 partially blocked laminin-411-induced pAkt activation (~50% inhibition).

Example 7. Effects of Laminin 411 and Anti-Laminin Antibodies on Notch Signaling Because Notch ligand D114 transcription/translation requires integrin ligation and subsequent phospho-Akt signaling, anti-LAMA4 antibodies are tested for effects on Notch signaling. HUVEC, WM266.4, and RAW cells are resuspended in cell culture media with 10 ug/ml laminin-411 (LAMA4 in complex with gamma1 and beta1 chains) and 20 ug/ml 15F7 or isotype control antibody for 24 hrs. BSA protein is used as a control for laminin 411. Cells are spun down and lysed for immunoblot analyses for cleaved/activated Notch1, D114, MCAM, actin, pAkt, and Akt. In addition, qPCR analysis for Hey1, MCP-1 (monocyte chemoattractant in inflammation), MCAM, LAMA4, and GAPDH is undertaken.

Example 8. Effects of Anti-Laminin Antibodies in In Vivo Obesity Models

Because Akt signaling is important for Notch signaling, and Notch signaling encourages growth of adipocytes, antibodies against LAMA4 are tested in in vivo obesity models for effects on weight gain/loss and adipocyte metabolism and lipolysis. High-fat diet (HFD)-driven weight gain in mice is assessed in response to anti-laminin 411 antibodies. Wild-type C57BL/6 mice are fed a high-fat diet (e.g., rodent diet with 45% kcal % fat, such as product #D12451 from Research Diets, Inc.) ad libitum. Two experimental groups are tested: (1) mice treated with control Ig; and (2) mice treated with 15F7. There are ten mice in each group, and each mouse is treated with 10 mg/kg/week antibody for three to four months. Weight measurements are taken every two to four weeks.

To assess localization of LAMA4 to adipose tissue, anti-LAMA4 antibody (compared to isotype control antibody) is intravenously administered to mice. Staining is then undertaken to assess localization to adipose tissue.

Example 9. Materials and Methods

LAMA4 Fragment Purification

His-tagged LAMA4 G-domain fragments were cloned by standard procedures and transiently expressed in 293 cells. Protein was purified using a nickel-NTA column.

LAMA4 Knockout Mouse

Lama4 null mice originally obtained from Dr. Karl Tryggvason (Karolinska University).

Generation of Recombinant MCAM-Fc Protein

MCAM-Fc was generated in house by fusing the extracellular domain of human or mouse MCAM to human IgG1 and produced/purified in CHO cells using standard techniques.

Antibody Generation

Recombinant mouse laminin 4 (Lama4) obtained from R&D Systems and 10 week old Lama4 null mice originally obtained from Dr. Karl Tryggvason (Karolinska University) were used to develop the antibodies. Purified laminin α4 (LAMA4) was suspended in RIBI adjuvant at 10 ug LAMA4/25 ul adjuvant. Mice were anesthetized with isoflurane and 3 mice were immunized into each rear footpad or rear hock with 5 ug Lama4 in RIBI adjuvant while two mice were immunized with 12.5 ug Lama4 in RIBI adjuvant into each rear footpad or rear hock with a 27 gauge needle. Mice were injected following the above procedure on days 0, 4, 12, 16 and 20. On day 24 animals are euthanized and the popiteal and inguinal lymph nodes are removed in a sterile hood. The nodes are dissociated and fused with SP2/0 using a modification of the Kohler and Milstein protocol that incorporates Electrofusion instead of PEG fusion. Fused cells are plated into 96 well plates and allowed to grow.

When cells reach half to three quarters confluence screening begins. Briefly, Costar RIA/EIA plates were coated with rabbit anti-His tag (Anaspec #29673) at 1 ug/mL, 50 uL/well, in PBS for 1 hour. Plates were then blocked with 250 ul/well of 1% BSA/PBS for 15 minutes and then removed. His-tagged Lama4 was added to the plates at 0.25 ug/mL, 50 uL/well for 1 hour, and then washed 2x. 75 uL of supernatant from fusion plates was added and incubated for 1 hour, plates were washed 2×. Goat-anti-mouse (Jackson #115-035-164) was added at 1:2000 dilution in 0.5% BSA/PBS/TBST for 1 hour, then washed 5×. Plates were developed with 50 ul/well TMB (SurModics #TMBW24) for 5 minutes, and stopped with 15 uL 2N H2SO4, and read at 450 nm. Wells with OD greater than 1.0 were selected for additional screening. Cells from wells found positive by the ELISA were grown up and frozen. Supernatants were provided for the additional screening described below. Cells from wells meeting certain criteria described below were cloned using the Clonepix FL and screened using setting recommended by the company to find single cell clones. These were expanded and the antibody purified from supernatants.

LAMA4 pDisplay Flow Cytometric Binding Assay

Human LAMA4 G-domains 1-5 and variants were cloned into pDisplay expression construct (Life Technologies) and transiently transfected into 293 cells using standard procedures. Anti-LAMA4 antibodies were incubated with cells for 30 min at 4° C. and followed by anti-mouse-650 for 30 minutes at 4° C. Cells were analyzed for anti-laminin binding by flow cytometry using standard procedures.

WM-266-4 Cell Transfection and Staining

Cultured WM-266-4 cells were transfected with full-length human MCAM-GFP fusion constructs and stained with anti-LAMA4 antibodies using standard procedures.

WM-266-4 Human Melanoma Subcutaneous Tumor Tissue

Cells were cultured and $5 \times 10^5$ cells per animal were subcutaneously administered above the shoulder in nude mice. After five weeks, animals were transcardially perfused with PBS and tumors were excised and snap frozen.

B16 Mouse Melanoma Subcutaneous Tumor Tissue

Cells were cultured and $5 \times 10^5$ cells per animal were subcutaneously administered above the shoulder in c57b16 mice. After five weeks, animals were transcardially perfused with PBS and tumors were excised and snap frozen.

B16 Mouse Melanoma Lung Metastasis Lung Tissue

Cells were cultured and $5 \times 10^5$ cells per animal were intravenously injected into nude/beige mice from Charles River (offsite at Caliper LifeSciences). After three weeks, animals were transcardially perfused with PBS, and lungs were excised and snap frozen.

Fluorescence Microscopy/Standard Immunofluorescent Methods

Mouse tissue was snap frozen in OCT and sectioned at 10 uM. Sections were fixed in cold acetone and stained with anti-LAMA4 antibody (R&D systems).

Human Melanoma Cell Adhesion Assay

Recombinant 10 ug/ml mLAMA4 (R&D systems), was used to coat 96-well plates overnight at 4° C. Following PBS washing steps, wells were blocked with 1% BSA/MEM for 1 hr at room temperature. 20 ug/ml anti-LAMA4 antibodies in 0.1% BSA/MEM were added to plates for 1 hour at room temperature. WM-266-4 cells were resuspended with EDTA, wash and resuspended at 300,000 cells/ml in 0.1%/MEM, followed by 10 minutes in the tissue culture incubator at 37° C. with the tube cap off. Following two washes with FACS buffer (1% FBS in PBS), cells were resuspended with 650-conjugated anti-pan-laminin antibody (1:1000; Novus Biologicals) and incubated for 20 min at 4° C., and washed again. Without removing antibody solutions, add cell suspension to well and incubate uncovered in tissue culture incubator for 1.5 hrs. Following a PBS wash step, cells were stained/fixed with glutaraldehyde/crystal violet solution prior to plate reader analysis at 570 nm.

Generation of Fab Fragments

Fab fragments of all antibodies were generated using the Fab Micro Preparation kit following manufacturer's directions (Pierce). Removal of liberated Fc and verification of intact final product were monitored by SDS-PAGE, and concentration was determined using the bicinchoninic acid assay (Pierce).

SPR Measurements of Affinity

SPR analysis was performed using a Biacore T200 to compare the binding of the different laminin antibodies. For Fab preparations, anti-6×His antibody (GE Life Sciences) was immobilized on sensor chip C1 via amine coupling, and human His-laminin-α4, mouse His-laminin-α4 (both from R & D Systems), and an unrelated 6×His-tagged protein (as a reaction control) were captured at a level to ensure maximum binding of 25 RU. Various concentrations of Fab preparations ranging from 300-0.41 nM were passed over the captured ligands in parallel at a flow rate of 50 ul/min in running buffer (EMS+0.05% P-20, 1 mg/mL BSA), for 240 s association and varying durations of dissociation. Data were double-referenced to both an irrelevant sensor not containing His-tagged ligand, and 0 nM analyte concentration to account for the dissociation of ligand from the capture moiety. Data was then analyzed using either a heterogeneous ligand model or a global 1:1 fit.

For whole IgG, anti-mouse antibody was immobilized on sensor chip C1 (lacking dextran chains) via amine coupling, and laminin mAbs were captured to a level to ensure a maximum binding of analyte of 50 RU. Various concentrations of analyte (recombinant human or mouse His-laminin-α4 fragment starting at Q826 (R&D Systems)) ranging from 31.25 nM to 0.122 nM were passed over the captured ligand at 30 ul/min in running buffer (EMS+0.05% P-20, 1 mg/mL BSA, except where described) for 180 s association/900 s dissociation. Data were double-referenced to both an irrelevant sensor not containing His-tagged ligand, and 0 nM analyte concentration to account for the dissociation of ligand from the capture moiety. Where possible, data were analyzed using a global 1:1 fit. If kinetic sensorgram curvature did not allow proper model-fitting, a steady-state approximation was performed and reported.

Saporin-Mediated WM-266-4 Cell Toxicity Assay

Per manufacturer's instructions (Advanced Targeting Systems).

Human Melanoma Tissue and Tumor Microarray Slides

Unfixed healthy and melanoma human skin slides were obtained from Origene. Acetone-fixed tumor microarray (TMA) slides were obtained from Biochain.

What is claimed is:

1. A method of treating a patient having a cancer, the method comprising administering to the patient an effective regime of an antibody that specifically binds to an epitope within the LG4-5 modules of the G domain of laminin α4, wherein the antibody comprises three light chain CDRs and three heavy chain CDRs from the heavy and light chain variable regions of SEQ ID NOS:16 and 17, respectively, SEQ ID NOS:26 and 27, respectively, or SEQ ID NOS:36 or 37, and 38, respectively.

2. The method of claim 1, wherein the cancer is melanoma, breast cancer, lung cancer, or colorectal cancer.

3. The method of claim 1, wherein the three heavy chain CDRs comprises SEQ ID NOS:20-22 respectively and the three light chain CDRs comprise SEQ ID NOS:23-25 respectively.

4. The method of claim 1, wherein the three heavy chain CDRs comprises SEQ ID NOS:30-32 respectively and the three light chain CDRs comprise SEQ ID NOS:33-35 respectively.

5. The method of claim 1, wherein the three heavy chain CDRs comprise SEQ ID NOS:42-44 respectively or SEQ ID NOS: 45-47 respectively, and the three light chain CDRs comprise SEQ ID NOS:48-50 respectively.

6. A method of inhibiting angiogenesis in a patient, the method comprising administering to the patient an effective regime of an antibody that specifically binds to an epitope within the LG4-5 modules of the G domain of laminin α4, wherein the antibody comprises three light chain CDRs and three heavy chain CDRs from the heavy and light chain variable regions of SEQ ID NOS:16 and 17, respectively, SEQ ID NOS:26 and 27, respectively, or SEQ ID NOS:36 or 37, and 38, respectively.

7. The method of claim 6, wherein the three heavy chain CDRs comprises SEQ ID NOS:20-22 respectively and the three light chain CDRs comprise SEQ ID NOS:23-25 respectively.

8. The method of claim 6, wherein the three heavy chain CDRs comprises SEQ ID NOS:30-32 respectively and the three light chain CDRs comprise SEQ ID NOS:33-35 respectively.

9. The method of claim 6, wherein the three heavy chain CDRs comprise SEQ ID NOS:42-44 respectively or SEQ ID NOS: 45-47 respectively, and the three light chain CDRs comprise SEQ ID NOS:48-50 respectively.

* * * * *

SEQUENCE LISTING

<160> NUMBER OF SEQ ID NOS: 102

<210> SEQ ID NO 1
<211> LENGTH: 1823
<212> TYPE: PRT
<213> ORGANISM: Homo sapiens

<400> SEQUENCE: 1

```
Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
            260                 265                 270

Cys Asp Lys Cys Val Trp Asp Leu Thr Asp Ala Leu Arg Leu Ala Ala
        275                 280                 285

Leu Ser Ile Glu Glu Gly Lys Ser Gly Val Leu Ser Val Ser Ser Gly
290                 295                 300

Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
        355                 360                 365

Leu Val Gln Lys Glu Ser Met Asp Thr Ile Asn His Ala Ser Gln Leu
370                 375                 380

Val Glu Gln Ala His Asp Met Arg Asp Lys Ile Gln Glu Ile Asn Asn
385                 390                 395                 400

Lys Met Leu Tyr Tyr Gly Glu Glu His Glu Leu Ser Pro Lys Glu Ile
```

```
                405                 410                 415
Ser Glu Lys Leu Val Leu Ala Gln Lys Met Leu Glu Glu Ile Arg Ser
                420                 425                 430

Arg Gln Pro Phe Phe Thr Gln Arg Glu Leu Val Asp Glu Glu Ala Asp
            435                 440                 445

Glu Ala Tyr Glu Leu Leu Ser Gln Ala Glu Ser Trp Gln Arg Leu His
        450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
                485                 490                 495

Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
        515                 520                 525

Val Val Asn Met Ser Leu Ser Thr Ser Ala Asp Ser Leu Thr Thr Pro
    530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575

Ser Asn Leu Ser Asn Leu Ser His Asp Leu Val Gln Glu Ala Ile Asp
            580                 585                 590

His Ala Gln Asp Leu Gln Gln Glu Ala Asn Glu Leu Ser Arg Lys Leu
        595                 600                 605

His Ser Ser Asp Met Asn Gly Leu Val Gln Lys Ala Leu Asp Ala Ser
    610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
                645                 650                 655

Gly Ile Asp Thr Gln Ile Ile Tyr His Lys Asp Glu Ser Glu Asn Leu
            660                 665                 670

Leu Asn Gln Ala Arg Glu Leu Gln Ala Lys Ala Glu Ser Ser Ser Asp
        675                 680                 685

Glu Ala Val Ala Asp Thr Ser Arg Arg Val Gly Gly Ala Leu Ala Arg
    690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
                725                 730                 735

Ile Thr Glu Glu Ala Asn Arg Thr Thr Met Glu Val Gln Gln Ala Thr
            740                 745                 750

Ala Pro Met Ala Asn Asn Leu Thr Asn Trp Ser Gln Asn Leu Gln His
        755                 760                 765

Phe Asp Ser Ser Ala Tyr Asn Thr Ala Val Asn Ser Ala Arg Asp Ala
    770                 775                 780

Val Arg Asn Leu Thr Glu Val Val Pro Gln Leu Leu Asp Gln Leu Arg
785                 790                 795                 800

Thr Val Glu Gln Lys Arg Pro Ala Ser Asn Val Ser Ala Ser Ile Gln
                805                 810                 815

Arg Ile Arg Glu Leu Ile Ala Gln Thr Arg Ser Val Ala Ser Lys Ile
            820                 825                 830
```

```
Gln Val Ser Met Met Phe Asp Gly Gln Ser Ala Val Glu Val His Ser
            835                 840                 845
Arg Thr Ser Met Asp Asp Leu Lys Ala Phe Thr Ser Leu Ser Leu Tyr
    850                 855                 860
Met Lys Pro Pro Val Lys Arg Pro Glu Leu Thr Glu Thr Ala Asp Gln
865                 870                 875                 880
Phe Ile Leu Tyr Leu Gly Ser Lys Asn Ala Lys Lys Glu Tyr Met Gly
                885                 890                 895
Leu Ala Ile Lys Asn Asp Asn Leu Val Tyr Val Tyr Asn Leu Gly Thr
            900                 905                 910
Lys Asp Val Glu Ile Pro Leu Asp Ser Lys Pro Val Ser Ser Trp Pro
            915                 920                 925
Ala Tyr Phe Ser Ile Val Lys Ile Glu Arg Val Gly Lys His Gly Lys
            930                 935                 940
Val Phe Leu Thr Val Pro Ser Leu Ser Ser Thr Ala Glu Glu Lys Phe
945                 950                 955                 960
Ile Lys Lys Gly Glu Phe Ser Gly Asp Asp Ser Leu Leu Asp Leu Asp
                965                 970                 975
Pro Glu Asp Thr Val Phe Tyr Val Gly Gly Val Pro Ser Asn Phe Lys
            980                 985                 990
Leu Pro Thr Ser Leu Asn Leu Pro Gly Phe Val Gly Cys Leu Glu Leu
            995                 1000                1005
Ala Thr Leu Asn Asn Asp Val Ile Ser Leu Tyr Asn Phe Lys His Ile
        1010                1015                1020
Tyr Asn Met Asp Pro Ser Thr Ser Val Pro Cys Ala Arg Asp Lys Leu
1025                1030                1035                1040
Ala Phe Thr Gln Ser Arg Ala Ala Ser Tyr Phe Phe Asp Gly Ser Gly
            1045                1050                1055
Tyr Ala Val Val Arg Asp Ile Thr Arg Arg Gly Lys Phe Gly Gln Val
            1060                1065                1070
Thr Arg Phe Asp Ile Glu Val Arg Thr Pro Ala Asp Asn Gly Leu Ile
        1075                1080                1085
Leu Leu Met Val Asn Gly Ser Met Phe Phe Arg Leu Glu Met Arg Asn
        1090                1095                1100
Gly Tyr Leu His Val Phe Tyr Asp Phe Gly Phe Ser Gly Gly Pro Val
1105                1110                1115                1120
His Leu Glu Asp Thr Leu Lys Lys Ala Gln Ile Asn Asp Ala Lys Tyr
            1125                1130                1135
His Glu Ile Ser Ile Ile Tyr His Asn Asp Lys Lys Met Ile Leu Val
        1140                1145                1150
Val Asp Arg Arg His Val Lys Ser Met Asp Asn Glu Lys Met Lys Ile
        1155                1160                1165
Pro Phe Thr Asp Ile Tyr Ile Gly Gly Ala Pro Pro Glu Ile Leu Gln
    1170                1175                1180
Ser Arg Ala Leu Arg Ala His Leu Pro Leu Asp Ile Asn Phe Arg Gly
1185                1190                1195                1200
Cys Met Lys Gly Phe Gln Phe Gln Lys Lys Asp Phe Asn Leu Leu Glu
            1205                1210                1215
Gln Thr Glu Thr Leu Gly Val Gly Tyr Gly Cys Pro Glu Asp Ser Leu
        1220                1225                1230
Ile Ser Arg Arg Ala Tyr Phe Asn Gly Gln Ser Phe Ile Ala Ser Ile
        1235                1240                1245
```

-continued

```
Gln Lys Ile Ser Phe Phe Asp Gly Phe Glu Gly Gly Phe Asn Phe Arg
    1250                1255                1260

Thr Leu Gln Pro Asn Gly Leu Leu Phe Tyr Tyr Ala Ser Gly Ser Asp
1265                1270                1275                1280

Val Phe Ser Ile Ser Leu Asp Asn Gly Thr Val Ile Met Asp Val Lys
                1285                1290                1295

Gly Ile Lys Val Gln Ser Val Asp Lys Gln Tyr Asn Asp Gly Leu Ser
            1300                1305                1310

His Phe Val Ile Ser Ser Val Ser Pro Thr Arg Tyr Glu Leu Ile Val
        1315                1320                1325

Asp Lys Ser Arg Val Gly Ser Lys Asn Pro Thr Lys Gly Lys Ile Glu
    1330                1335                1340

Gln Thr Gln Ala Ser Glu Lys Lys Phe Tyr Phe Gly Gly Ser Pro Ile
1345                1350                1355                1360

Ser Ala Gln Tyr Ala Asn Phe Thr Gly Cys Ile Ser Asn Ala Tyr Phe
                1365                1370                1375

Thr Arg Val Asp Arg Asp Val Glu Val Glu Asp Phe Gln Arg Tyr Thr
            1380                1385                1390

Glu Lys Val His Thr Ser Leu Tyr Glu Cys Pro Ile Glu Ser Ser Pro
        1395                1400                1405

Leu Phe Leu Leu His Lys Lys Gly Lys Asn Leu Ser Lys Pro Lys Ala
    1410                1415                1420

Ser Gln Asn Lys Lys Gly Gly Lys Ser Lys Asp Ala Pro Ser Trp Asp
1425                1430                1435                1440

Pro Val Ala Leu Lys Leu Pro Glu Arg Asn Thr Pro Arg Asn Ser His
                1445                1450                1455

Cys His Leu Ser Asn Ser Pro Arg Ala Ile Glu His Ala Tyr Gln Tyr
            1460                1465                1470

Gly Gly Thr Ala Asn Ser Arg Gln Glu Phe Glu His Leu Lys Gly Asp
        1475                1480                1485

Phe Gly Ala Lys Ser Gln Phe Ser Ile Arg Leu Arg Thr Arg Ser Ser
    1490                1495                1500

His Gly Met Ile Phe Tyr Val Ser Asp Gln Glu Glu Asn Asp Phe Met
1505                1510                1515                1520

Thr Leu Phe Leu Ala His Gly Arg Leu Val Tyr Met Phe Asn Val Gly
                1525                1530                1535

His Lys Lys Leu Lys Ile Arg Ser Gln Glu Lys Tyr Asn Asp Gly Leu
            1540                1545                1550

Trp His Asp Val Ile Phe Ile Arg Glu Arg Ser Ser Gly Arg Leu Val
        1555                1560                1565

Ile Asp Gly Leu Arg Val Leu Glu Glu Ser Leu Pro Pro Thr Glu Ala
    1570                1575                1580

Thr Trp Lys Ile Lys Gly Pro Ile Tyr Leu Gly Gly Val Ala Pro Gly
1585                1590                1595                1600

Lys Ala Val Lys Asn Val Gln Ile Asn Ser Ile Tyr Ser Phe Ser Gly
                1605                1610                1615

Cys Leu Ser Asn Leu Gln Leu Asn Gly Ala Ser Ile Thr Ser Ala Ser
            1620                1625                1630

Gln Thr Phe Ser Val Thr Pro Cys Phe Glu Gly Pro Met Glu Thr Gly
        1635                1640                1645

Thr Tyr Phe Ser Thr Glu Gly Gly Tyr Val Val Leu Asp Glu Ser Phe
    1650                1655                1660

Asn Ile Gly Leu Lys Phe Glu Ile Ala Phe Glu Val Arg Pro Arg Ser
```

```
1665                1670                1675                1680

Ser Ser Gly Thr Leu Val His Gly His Ser Val Asn Gly Glu Tyr Leu
                1685                1690                1695

Asn Val His Met Lys Asn Gly Gln Val Ile Val Lys Val Asn Asn Gly
            1700                1705                1710

Ile Arg Asp Phe Ser Thr Ser Val Thr Pro Lys Gln Ser Leu Cys Asp
            1715                1720                1725

Gly Arg Trp His Arg Ile Thr Val Ile Arg Asp Ser Asn Val Val Gln
        1730                1735                1740

Leu Asp Val Asp Ser Glu Val Asn His Val Val Gly Pro Leu Asn Pro
1745                1750                1755                1760

Lys Pro Ile Asp His Arg Glu Pro Val Phe Val Gly Val Pro Glu
                1765                1770                1775

Ser Leu Leu Thr Pro Arg Leu Ala Pro Ser Lys Pro Phe Thr Gly Cys
            1780                1785                1790

Ile Arg His Phe Val Ile Asp Gly His Pro Val Ser Phe Ser Lys Ala
            1795                1800                1805

Ala Leu Val Ser Gly Ala Val Ser Ile Asn Ser Cys Pro Ala Ala
        1810                1815                1820

<210> SEQ ID NO 2
<211> LENGTH: 1823
<212> TYPE: PRT
<213> ORGANISM: Homo sapiens

<400> SEQUENCE: 2

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220
```

```
Ala Pro Gly Tyr Tyr Gly Asp Ala Arg Ile Ala Lys Asn Cys Ala Val
225                 230                 235                 240

Cys Asn Cys Gly Gly Pro Cys Asp Ser Val Thr Gly Glu Cys Leu
            245                 250                 255

Glu Glu Gly Phe Glu Pro Pro Thr Gly Met Asp Cys Pro Thr Ile Ser
                260                 265                 270

Cys Asp Lys Cys Val Trp Asp Leu Thr Asp Asp Leu Arg Leu Ala Ala
        275                 280                 285

Leu Ser Ile Glu Glu Gly Lys Ser Gly Val Leu Ser Val Ser Ser Gly
    290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
                340                 345                 350

Val Glu Glu Leu Val Lys Glu Asn Gln Ala Ser Arg Lys Gly Gln
    355                 360                 365

Leu Val Gln Lys Glu Ser Met Asp Thr Ile Asn His Ala Ser Gln Leu
370                 375                 380

Val Glu Gln Ala His Asp Met Arg Asp Lys Ile Gln Glu Ile Asn Asn
385                 390                 395                 400

Lys Met Leu Tyr Tyr Gly Glu His Glu Leu Ser Pro Lys Glu Ile
                405                 410                 415

Ser Glu Lys Leu Val Leu Ala Gln Lys Met Leu Glu Glu Ile Arg Ser
                420                 425                 430

Arg Gln Pro Phe Phe Thr Gln Arg Glu Leu Val Asp Glu Glu Ala Asp
            435                 440                 445

Glu Ala Tyr Glu Leu Leu Ser Gln Ala Glu Ser Trp Gln Arg Leu His
    450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
                485                 490                 495

Asn Tyr Val Arg Asp Ala Glu Asp Met Asn Arg Ala Thr Ala Ala Arg
                500                 505                 510

Gln Arg Asp His Glu Lys Gln Gln Glu Arg Val Arg Glu Gln Met Glu
            515                 520                 525

Val Val Asn Met Ser Leu Ser Thr Ser Ala Asp Ser Leu Thr Thr Pro
530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575

Ser Asn Leu Ser Asn Leu Ser His Asp Leu Val Gln Glu Ala Ile Asp
            580                 585                 590

His Ala Gln Asp Leu Gln Gln Glu Ala Asn Glu Leu Ser Arg Lys Leu
            595                 600                 605

His Ser Ser Asp Met Asn Gly Leu Val Gln Lys Ala Leu Asp Ala Ser
            610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
```

-continued

```
                645                 650                 655
Gly Ile Asp Thr Gln Ile Ile Tyr His Lys Asp Glu Ser Glu Asn Leu
                660                 665                 670

Leu Asn Gln Ala Arg Glu Leu Gln Ala Lys Ala Glu Ser Ser Ser Asp
                675                 680                 685

Glu Ala Val Ala Asp Thr Ser Arg Arg Val Gly Gly Ala Leu Ala Arg
                690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
                725                 730                 735

Ile Thr Glu Glu Ala Asn Arg Thr Thr Met Glu Val Gln Gln Ala Thr
                740                 745                 750

Ala Pro Met Ala Asn Asn Leu Thr Asn Trp Ser Gln Asn Leu Gln His
                755                 760                 765

Phe Asp Ser Ser Ala Tyr Asn Thr Ala Val Asn Ser Ala Arg Asp Ala
                770                 775                 780

Val Arg Asn Leu Thr Glu Val Val Pro Gln Leu Leu Asp Gln Leu Arg
785                 790                 795                 800

Thr Val Glu Gln Lys Arg Pro Ala Ser Asn Val Ser Ala Ser Ile Gln
                805                 810                 815

Arg Ile Arg Glu Leu Ile Ala Gln Thr Arg Ser Val Ala Ser Lys Ile
                820                 825                 830

Gln Val Ser Met Met Phe Asp Gly Gln Ser Ala Val Glu Val His Ser
                835                 840                 845

Arg Thr Ser Met Asp Asp Leu Lys Ala Phe Thr Ser Leu Ser Leu Tyr
                850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
                885                 890                 895

Leu Ala Ile Lys Asn Asp Asn Leu Val Tyr Val Tyr Asn Leu Gly Thr
                900                 905                 910

Lys Asp Val Glu Ile Pro Leu Asp Ser Lys Pro Val Ser Ser Trp Pro
                915                 920                 925

Ala Tyr Phe Ser Ile Val Lys Ile Glu Arg Val Gly Lys His Gly Lys
                930                 935                 940

Val Phe Leu Thr Val Pro Ser Leu Ser Ser Thr Ala Glu Glu Lys Phe
945                 950                 955                 960

Ile Lys Lys Gly Glu Phe Ser Gly Asp Asp Ser Leu Leu Asp Leu Asp
                965                 970                 975

Pro Glu Asp Thr Val Phe Tyr Val Gly Gly Val Pro Ser Asn Phe Lys
                980                 985                 990

Leu Pro Thr Ser Leu Asn Leu Pro Gly Phe Val Gly Cys Leu Glu Leu
                995                 1000                1005

Ala Thr Leu Asn Asn Asp Val Ile Ser Leu Tyr Asn Phe Lys His Ile
                1010                1015                1020

Tyr Asn Met Asp Pro Ser Thr Ser Val Pro Cys Ala Arg Asp Lys Leu
1025                1030                1035                1040

Ala Phe Thr Gln Ser Arg Ala Ala Ser Tyr Phe Phe Asp Gly Ser Gly
                1045                1050                1055

Tyr Ala Val Val Arg Asp Ile Thr Arg Arg Gly Lys Phe Gly Gln Val
                1060                1065                1070
```

```
Thr Arg Phe Asp Ile Glu Val Arg Thr Pro Ala Asp Asn Gly Leu Ile
        1075                1080                1085
Leu Leu Met Val Asn Gly Ser Met Phe Phe Arg Leu Glu Met Arg Asn
        1090                1095                1100
Gly Tyr Leu His Val Phe Tyr Asp Phe Gly Ser Gly Gly Pro Val
1105                1110                1115                1120
His Leu Glu Asp Thr Leu Lys Lys Ala Gln Ile Asn Asp Ala Lys Tyr
        1125                1130                1135
His Glu Ile Ser Ile Ile Tyr His Asn Asp Lys Lys Met Ile Leu Val
        1140                1145                1150
Val Asp Arg Arg His Val Lys Ser Met Asp Asn Glu Lys Met Lys Ile
        1155                1160                1165
Pro Phe Thr Asp Ile Tyr Ile Gly Gly Ala Pro Pro Glu Ile Leu Gln
        1170                1175                1180
Ser Arg Ala Leu Arg Ala His Leu Pro Leu Asp Ile Asn Phe Arg Gly
1185                1190                1195                1200
Cys Met Lys Gly Phe Gln Phe Gln Lys Lys Asp Phe Asn Leu Leu Glu
        1205                1210                1215
Gln Thr Glu Thr Leu Gly Val Gly Tyr Gly Cys Pro Gly Asp Ser Leu
        1220                1225                1230
Ile Ser Arg Arg Ala Tyr Phe Asn Gly Gln Ser Phe Ile Ala Ser Ile
        1235                1240                1245
Gln Lys Ile Ser Phe Phe Asp Gly Phe Glu Gly Gly Phe Asn Phe Arg
        1250                1255                1260
Thr Leu Gln Pro Asn Gly Leu Leu Phe Tyr Tyr Ala Ser Gly Ser Asp
1265                1270                1275                1280
Val Phe Ser Ile Ser Leu Asp Asn Gly Thr Val Ile Met Asp Val Lys
        1285                1290                1295
Gly Ile Lys Val Gln Ser Val Asp Lys Gln Tyr Asn Asp Gly Leu Ser
        1300                1305                1310
His Phe Val Ile Ser Ser Val Ser Pro Thr Arg Tyr Glu Leu Ile Val
        1315                1320                1325
Asp Lys Ser Arg Val Gly Ser Lys Asn Pro Thr Lys Gly Lys Ile Glu
        1330                1335                1340
Gln Thr Gln Ala Ser Glu Lys Lys Phe Tyr Phe Gly Gly Ser Pro Ile
1345                1350                1355                1360
Ser Ala Gln Tyr Ala Asn Phe Thr Gly Cys Ile Ser Asn Ala Tyr Phe
        1365                1370                1375
Thr Arg Val Asp Arg Asp Val Glu Val Glu Asp Phe Gln Arg Tyr Thr
        1380                1385                1390
Glu Lys Val His Thr Ser Leu Tyr Glu Cys Pro Ile Glu Ser Ser Pro
        1395                1400                1405
Leu Phe Leu Leu His Lys Lys Gly Lys Asn Leu Ser Lys Pro Lys Ala
        1410                1415                1420
Ser Gln Asn Lys Lys Gly Gly Lys Ser Lys Asp Ala Pro Ser Trp Asp
1425                1430                1435                1440
Pro Val Ala Leu Lys Leu Pro Glu Arg Asn Thr Pro Arg Asn Ser His
        1445                1450                1455
Cys His Leu Ser Asn Ser Pro Arg Ala Ile Glu His Ala Tyr Gln Tyr
        1460                1465                1470
Gly Gly Thr Ala Asn Ser Arg Gln Glu Phe Glu His Leu Lys Gly Asp
        1475                1480                1485
```

```
Phe Gly Ala Lys Ser Gln Phe Ser Ile Arg Leu Arg Thr Arg Ser Ser
    1490                1495                1500
His Gly Met Ile Phe Tyr Val Ser Asp Gln Glu Glu Asn Asp Phe Met
1505                1510                1515                1520
Thr Leu Phe Leu Ala His Gly Arg Leu Val Tyr Met Phe Asn Val Gly
                1525                1530                1535
His Lys Lys Leu Lys Ile Arg Ser Gln Glu Lys Tyr Asn Asp Gly Leu
            1540                1545                1550
Trp His Asp Val Ile Phe Ile Arg Glu Arg Ser Ser Gly Arg Leu Val
        1555                1560                1565
Ile Asp Gly Leu Arg Val Leu Glu Glu Ser Leu Pro Pro Thr Glu Ala
    1570                1575                1580
Thr Trp Lys Ile Lys Gly Pro Ile Tyr Leu Gly Gly Val Ala Pro Gly
1585                1590                1595                1600
Lys Ala Val Lys Asn Val Gln Ile Asn Ser Ile Tyr Ser Phe Ser Gly
                1605                1610                1615
Cys Leu Ser Asn Leu Gln Leu Asn Gly Ala Ser Ile Thr Ser Ala Ser
            1620                1625                1630
Gln Thr Phe Ser Val Thr Pro Cys Phe Glu Gly Pro Met Glu Thr Gly
        1635                1640                1645
Thr Tyr Phe Ser Thr Glu Gly Gly Tyr Val Val Leu Asp Glu Ser Phe
    1650                1655                1660
Asn Ile Gly Leu Lys Phe Glu Ile Ala Phe Glu Val Arg Pro Arg Ser
1665                1670                1675                1680
Ser Ser Gly Thr Leu Val His Gly His Ser Val Asn Gly Glu Tyr Leu
                1685                1690                1695
Asn Val His Met Lys Asn Gly Gln Val Ile Val Lys Val Asn Asn Gly
            1700                1705                1710
Ile Arg Asp Phe Ser Thr Ser Val Thr Pro Lys Gln Ser Leu Cys Asp
        1715                1720                1725
Gly Arg Trp His Arg Ile Thr Val Ile Arg Asp Ser Asn Val Val Gln
    1730                1735                1740
Leu Asp Val Asp Ser Glu Val Asn His Val Val Gly Pro Leu Asn Pro
1745                1750                1755                1760
Lys Pro Ile Asp His Arg Glu Pro Val Phe Val Gly Gly Val Pro Glu
                1765                1770                1775
Ser Leu Leu Thr Pro Arg Leu Ala Pro Ser Lys Pro Phe Thr Gly Cys
            1780                1785                1790
Ile Arg His Phe Val Ile Asp Gly His Pro Val Ser Phe Ser Lys Ala
        1795                1800                1805
Ala Leu Val Ser Gly Ala Val Ser Ile Asn Ser Cys Pro Ala Ala
    1810                1815                1820

<210> SEQ ID NO 3
<211> LENGTH: 1816
<212> TYPE: PRT
<213> ORGANISM: Homo sapiens

<400> SEQUENCE: 3

Met Ala Leu Ser Ser Ala Trp Arg Ser Val Leu Pro Leu Trp Leu Leu
1               5                   10                  15
Trp Ser Ala Ala Cys Ser Arg Ala Ala Ser Gly Asp Asp Asn Ala Phe
            20                  25                  30
Pro Phe Asp Ile Glu Gly Ser Ser Ala Val Gly Arg Gln Asp Pro Pro
        35                  40                  45
```

```
Glu Thr Ser Glu Pro Arg Val Ala Leu Gly Arg Leu Pro Ala Ala
 50                  55                  60

Glu Lys Cys Asn Ala Gly Phe Phe His Thr Leu Ser Gly Glu Cys Val
 65                  70                  75                  80

Pro Cys Asp Cys Asn Gly Asn Ser Asn Glu Cys Leu Asp Gly Ser Gly
                 85                  90                  95

Tyr Cys Val His Cys Gln Arg Asn Thr Thr Gly Glu His Cys Glu Lys
                100                 105                 110

Cys Leu Asp Gly Tyr Ile Gly Asp Ser Ile Arg Gly Ala Pro Gln Phe
             115                 120                 125

Cys Gln Pro Cys Pro Cys Pro Leu Pro His Leu Ala Asn Phe Ala Glu
         130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
             180                 185                 190

Ser Asp Pro Asn Leu Ile Phe Glu Asp Cys Asp Glu Val Thr Gly Gln
         195                 200                 205

Cys Arg Asn Cys Leu Arg Asn Thr Thr Gly Phe Lys Cys Glu Arg Cys
210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Cys Asp Lys Cys Val Trp Asp
                260                 265                 270

Leu Thr Asp Asp Leu Arg Leu Ala Ala Leu Ser Ile Glu Glu Gly Lys
             275                 280                 285

Ser Gly Val Leu Ser Val Ser Ser Gly Ala Ala Ala His Arg His Val
         290                 295                 300

Asn Glu Ile Asn Ala Thr Ile Tyr Leu Leu Lys Thr Lys Leu Ser Glu
305                 310                 315                 320

Arg Glu Asn Gln Tyr Ala Leu Arg Lys Ile Gln Ile Asn Asn Ala Glu
                325                 330                 335

Asn Thr Met Lys Ser Leu Leu Ser Asp Val Glu Glu Leu Val Glu Lys
             340                 345                 350

Glu Asn Gln Ala Ser Arg Lys Gly Gln Leu Val Gln Lys Glu Ser Met
         355                 360                 365

Asp Thr Ile Asn His Ala Ser Gln Leu Val Glu Gln Ala His Asp Met
         370                 375                 380

Arg Asp Lys Ile Gln Glu Ile Asn Asn Lys Met Leu Tyr Tyr Gly Glu
385                 390                 395                 400

Glu His Glu Leu Ser Pro Lys Glu Ile Ser Glu Lys Leu Val Leu Ala
                405                 410                 415

Gln Lys Met Leu Glu Glu Ile Arg Ser Arg Gln Pro Phe Phe Thr Gln
             420                 425                 430

Arg Glu Leu Val Asp Glu Glu Ala Asp Glu Ala Tyr Glu Leu Leu Ser
         435                 440                 445

Gln Ala Glu Ser Trp Gln Arg Leu His Asn Glu Thr Arg Thr Leu Phe
450                 455                 460
```

-continued

```
Pro Val Val Leu Glu Gln Leu Asp Asp Tyr Asn Ala Lys Leu Ser Asp
465                 470                 475                 480

Leu Gln Glu Ala Leu Asp Gln Ala Leu Asn Tyr Val Arg Asp Ala Glu
            485                 490                 495

Asp Met Asn Arg Ala Thr Ala Ala Arg Gln Arg Asp His Glu Lys Gln
                500                 505                 510

Gln Glu Arg Val Arg Glu Gln Met Glu Val Val Asn Met Ser Leu Ser
        515                 520                 525

Thr Ser Ala Asp Ser Leu Thr Thr Pro Arg Leu Thr Leu Ser Glu Leu
    530                 535                 540

Asp Asp Ile Ile Lys Asn Ala Ser Gly Ile Tyr Ala Glu Ile Asp Gly
545                 550                 555                 560

Ala Lys Ser Glu Leu Gln Val Lys Leu Ser Asn Leu Ser Asn Leu Ser
            565                 570                 575

His Asp Leu Val Gln Glu Ala Ile Asp His Ala Gln Asp Leu Gln Gln
                580                 585                 590

Glu Ala Asn Glu Leu Ser Arg Lys Leu His Ser Ser Asp Met Asn Gly
        595                 600                 605

Leu Val Gln Lys Ala Leu Asp Ala Ser Asn Val Tyr Glu Asn Ile Val
    610                 615                 620

Asn Tyr Val Ser Glu Ala Asn Glu Thr Ala Glu Phe Ala Leu Asn Thr
625                 630                 635                 640

Thr Asp Arg Ile Tyr Asp Ala Val Ser Gly Ile Asp Thr Gln Ile Ile
            645                 650                 655

Tyr His Lys Asp Glu Ser Glu Asn Leu Leu Asn Gln Ala Arg Glu Leu
                660                 665                 670

Gln Ala Lys Ala Glu Ser Ser Asp Glu Ala Val Ala Asp Thr Ser
        675                 680                 685

Arg Arg Val Gly Gly Ala Leu Ala Arg Lys Ser Ala Leu Lys Thr Arg
    690                 695                 700

Leu Ser Asp Ala Val Lys Gln Leu Gln Ala Ala Glu Arg Gly Asp Ala
705                 710                 715                 720

Gln Gln Arg Leu Gly Gln Ser Arg Leu Ile Thr Glu Glu Ala Asn Arg
            725                 730                 735

Thr Thr Met Glu Val Gln Gln Ala Thr Ala Pro Met Ala Asn Asn Leu
                740                 745                 750

Thr Asn Trp Ser Gln Asn Leu Gln His Phe Asp Ser Ser Ala Tyr Asn
        755                 760                 765

Thr Ala Val Asn Ser Ala Arg Asp Ala Val Arg Asn Leu Thr Glu Val
    770                 775                 780

Val Pro Gln Leu Leu Asp Gln Leu Arg Thr Val Glu Gln Lys Arg Pro
785                 790                 795                 800

Ala Ser Asn Val Ser Ala Ser Ile Gln Arg Ile Arg Glu Leu Ile Ala
            805                 810                 815

Gln Thr Arg Ser Val Ala Ser Lys Ile Gln Val Ser Met Met Phe Asp
                820                 825                 830

Gly Gln Ser Ala Val Glu Val His Ser Arg Thr Ser Met Asp Asp Leu
        835                 840                 845

Lys Ala Phe Thr Ser Leu Ser Leu Tyr Met Lys Pro Pro Val Lys Arg
    850                 855                 860

Pro Glu Leu Thr Glu Thr Ala Asp Gln Phe Ile Leu Tyr Leu Gly Ser
865                 870                 875                 880

Lys Asn Ala Lys Lys Glu Tyr Met Gly Leu Ala Ile Lys Asn Asp Asn
```

```
                    885                 890                 895
Leu Val Tyr Val Tyr Asn Leu Gly Thr Lys Asp Val Glu Ile Pro Leu
                900                 905                 910

Asp Ser Lys Pro Val Ser Ser Trp Pro Ala Tyr Phe Ser Ile Val Lys
                915                 920                 925

Ile Glu Arg Val Gly Lys His Gly Lys Val Phe Leu Thr Val Pro Ser
                930                 935                 940

Leu Ser Ser Thr Ala Glu Glu Lys Phe Ile Lys Lys Gly Glu Phe Ser
945                 950                 955                 960

Gly Asp Asp Ser Leu Leu Asp Leu Asp Pro Glu Asp Thr Val Phe Tyr
                965                 970                 975

Val Gly Gly Val Pro Ser Asn Phe Lys Leu Pro Thr Ser Leu Asn Leu
                980                 985                 990

Pro Gly Phe Val Gly Cys Leu Glu Leu Ala Thr Leu Asn Asn Asp Val
                995                 1000                1005

Ile Ser Leu Tyr Asn Phe Lys His Ile Tyr Asn Met Asp Pro Ser Thr
                1010                1015                1020

Ser Val Pro Cys Ala Arg Asp Lys Leu Ala Phe Thr Gln Ser Arg Ala
1025                1030                1035                1040

Ala Ser Tyr Phe Phe Asp Gly Ser Gly Tyr Ala Val Val Arg Asp Ile
                1045                1050                1055

Thr Arg Arg Gly Lys Phe Gly Gln Val Thr Arg Phe Asp Ile Glu Val
                1060                1065                1070

Arg Thr Pro Ala Asp Asn Gly Leu Ile Leu Leu Met Val Asn Gly Ser
                1075                1080                1085

Met Phe Phe Arg Leu Glu Met Arg Asn Gly Tyr Leu His Val Phe Tyr
                1090                1095                1100

Asp Phe Gly Phe Ser Gly Gly Pro Val His Leu Glu Asp Thr Leu Lys
1105                1110                1115                1120

Lys Ala Gln Ile Asn Asp Ala Lys Tyr His Glu Ile Ser Ile Ile Tyr
                1125                1130                1135

His Asn Asp Lys Lys Met Ile Leu Val Val Asp Arg Arg His Val Lys
                1140                1145                1150

Ser Met Asp Asn Glu Lys Met Lys Ile Pro Phe Thr Asp Ile Tyr Ile
                1155                1160                1165

Gly Gly Ala Pro Pro Glu Ile Leu Gln Ser Arg Ala Leu Arg Ala His
                1170                1175                1180

Leu Pro Leu Asp Ile Asn Phe Arg Gly Cys Met Lys Gly Phe Gln Phe
1185                1190                1195                1200

Gln Lys Lys Asp Phe Asn Leu Leu Glu Gln Thr Glu Thr Leu Gly Val
                1205                1210                1215

Gly Tyr Gly Cys Pro Glu Asp Ser Leu Ile Ser Arg Arg Ala Tyr Phe
                1220                1225                1230

Asn Gly Gln Ser Phe Ile Ala Ser Ile Gln Lys Ile Ser Phe Phe Asp
                1235                1240                1245

Gly Phe Glu Gly Gly Phe Asn Phe Arg Thr Leu Gln Pro Asn Gly Leu
                1250                1255                1260

Leu Phe Tyr Tyr Ala Ser Gly Ser Asp Val Phe Ser Ile Ser Leu Asp
1265                1270                1275                1280

Asn Gly Thr Val Ile Met Asp Val Lys Gly Ile Lys Val Gln Ser Val
                1285                1290                1295

Asp Lys Gln Tyr Asn Asp Gly Leu Ser His Phe Val Ile Ser Ser Val
                1300                1305                1310
```

-continued

```
Ser Pro Thr Arg Tyr Glu Leu Ile Val Asp Lys Ser Arg Val Gly Ser
    1315                1320                1325

Lys Asn Pro Thr Lys Gly Lys Ile Glu Gln Thr Gln Ala Ser Glu Lys
1330                1335                1340

Lys Phe Tyr Phe Gly Gly Ser Pro Ile Ser Ala Gln Tyr Ala Asn Phe
1345                1350                1355                1360

Thr Gly Cys Ile Ser Asn Ala Tyr Phe Thr Arg Val Asp Arg Asp Val
                1365                1370                1375

Glu Val Glu Asp Phe Gln Arg Tyr Thr Glu Lys Val His Thr Ser Leu
            1380                1385                1390

Tyr Glu Cys Pro Ile Glu Ser Ser Pro Leu Phe Leu His Lys Lys
            1395                1400                1405

Gly Lys Asn Leu Ser Lys Pro Lys Ala Ser Gln Asn Lys Lys Gly Gly
        1410                1415                1420

Lys Ser Lys Asp Ala Pro Ser Trp Asp Pro Val Ala Leu Lys Leu Pro
1425                1430                1435                1440

Glu Arg Asn Thr Pro Arg Asn Ser His Cys His Leu Ser Asn Ser Pro
                1445                1450                1455

Arg Ala Ile Glu His Ala Tyr Gln Tyr Gly Gly Thr Ala Asn Ser Arg
            1460                1465                1470

Gln Glu Phe Glu His Leu Lys Gly Asp Phe Gly Ala Lys Ser Gln Phe
        1475                1480                1485

Ser Ile Arg Leu Arg Thr Arg Ser Ser His Gly Met Ile Phe Tyr Val
        1490                1495                1500

Ser Asp Gln Glu Glu Asn Asp Phe Met Thr Leu Phe Leu Ala His Gly
1505                1510                1515                1520

Arg Leu Val Tyr Met Phe Asn Val Gly His Lys Lys Leu Lys Ile Arg
            1525                1530                1535

Ser Gln Glu Lys Tyr Asn Asp Gly Leu Trp His Asp Val Ile Phe Ile
            1540                1545                1550

Arg Glu Arg Ser Ser Gly Arg Leu Val Ile Asp Gly Leu Arg Val Leu
            1555                1560                1565

Glu Glu Ser Leu Pro Pro Thr Glu Ala Thr Trp Lys Ile Lys Gly Pro
        1570                1575                1580

Ile Tyr Leu Gly Gly Val Ala Pro Gly Lys Ala Val Lys Asn Val Gln
1585                1590                1595                1600

Ile Asn Ser Ile Tyr Ser Phe Ser Gly Cys Leu Ser Asn Leu Gln Leu
                1605                1610                1615

Asn Gly Ala Ser Ile Thr Ser Ala Ser Gln Thr Phe Ser Val Thr Pro
            1620                1625                1630

Cys Phe Glu Gly Pro Met Glu Thr Gly Thr Tyr Phe Ser Thr Glu Gly
        1635                1640                1645

Gly Tyr Val Val Leu Asp Glu Ser Phe Asn Ile Gly Leu Lys Phe Glu
    1650                1655                1660

Ile Ala Phe Glu Val Arg Pro Arg Ser Ser Ser Gly Thr Leu Val His
1665                1670                1675                1680

Gly His Ser Val Asn Gly Glu Tyr Leu Asn Val His Met Lys Asn Gly
                1685                1690                1695

Gln Val Ile Val Lys Val Asn Asn Gly Ile Arg Asp Phe Ser Thr Ser
            1700                1705                1710

Val Thr Pro Lys Gln Ser Leu Cys Asp Gly Arg Trp His Arg Ile Thr
        1715                1720                1725
```

-continued

```
Val Ile Arg Asp Ser Asn Val Val Gln Leu Asp Val Asp Ser Glu Val
    1730                1735                1740

Asn His Val Val Gly Pro Leu Asn Pro Lys Pro Ile Asp His Arg Glu
1745                1750                1755                1760

Pro Val Phe Val Gly Val Pro Glu Ser Leu Leu Thr Pro Arg Leu
                1765                1770                1775

Ala Pro Ser Lys Pro Phe Thr Gly Cys Ile Arg His Phe Val Ile Asp
            1780                1785                1790

Gly His Pro Val Ser Phe Ser Lys Ala Ala Leu Val Ser Gly Ala Val
                1795                1800                1805

Ser Ile Asn Ser Cys Pro Ala Ala
    1810                1815
```

<210> SEQ ID NO 4
<211> LENGTH: 992
<212> TYPE: PRT
<213> ORGANISM: Artificial Sequence
<220> FEATURE:
<223> OTHER INFORMATION: G domain of human LAMA4

<400> SEQUENCE: 4

```
Ser Lys Ile Gln Val Ser Met Met Phe Asp Gly Gln Ser Ala Val Glu
1               5                   10                  15

Val His Ser Arg Thr Ser Met Asp Asp Leu Lys Ala Phe Thr Ser Leu
                20                  25                  30

Ser Leu Tyr Met Lys Pro Pro Val Lys Arg Pro Glu Leu Thr Glu Thr
            35                  40                  45

Ala Asp Gln Phe Ile Leu Tyr Leu Gly Ser Lys Asn Ala Lys Lys Glu
50                  55                  60

Tyr Met Gly Leu Ala Ile Lys Asn Asp Asn Leu Val Tyr Val Tyr Asn
65                  70                  75                  80

Leu Gly Thr Lys Asp Val Glu Ile Pro Leu Asp Ser Lys Pro Val Ser
                85                  90                  95

Ser Trp Pro Ala Tyr Phe Ser Ile Val Lys Ile Glu Arg Val Gly Lys
            100                 105                 110

His Gly Lys Val Phe Leu Thr Val Pro Ser Leu Ser Ser Thr Ala Glu
            115                 120                 125

Glu Lys Phe Ile Lys Lys Gly Glu Phe Ser Gly Asp Asp Ser Leu Leu
130                 135                 140

Asp Leu Asp Pro Glu Asp Thr Val Phe Tyr Val Gly Gly Val Pro Ser
145                 150                 155                 160

Asn Phe Lys Leu Pro Thr Ser Leu Asn Leu Pro Gly Phe Val Gly Cys
                165                 170                 175

Leu Glu Leu Ala Thr Leu Asn Asn Asp Val Ile Ser Leu Tyr Asn Phe
            180                 185                 190

Lys His Ile Tyr Asn Met Asp Pro Ser Thr Ser Val Pro Cys Ala Arg
            195                 200                 205

Asp Lys Leu Ala Phe Thr Gln Ser Arg Ala Ala Ser Tyr Phe Phe Asp
        210                 215                 220

Gly Ser Gly Tyr Ala Val Val Arg Asp Ile Thr Arg Arg Gly Lys Phe
225                 230                 235                 240

Gly Gln Val Thr Arg Phe Asp Ile Glu Val Arg Thr Pro Ala Asp Asn
                245                 250                 255

Gly Leu Ile Leu Leu Met Val Asn Gly Ser Met Phe Arg Leu Glu
                260                 265                 270
```

-continued

```
Met Arg Asn Gly Tyr Leu His Val Phe Tyr Asp Phe Gly Phe Ser Ser
        275                 280                 285

Gly Arg Val His Leu Glu Asp Thr Leu Lys Lys Ala Gln Ile Asn Asp
    290                 295                 300

Ala Lys Tyr His Glu Ile Ser Ile Ile Tyr His Asn Asp Lys Lys Met
305                 310                 315                 320

Ile Leu Val Val Asp Arg Arg His Val Lys Ser Met Asp Asn Glu Lys
                325                 330                 335

Met Lys Ile Pro Phe Thr Asp Ile Tyr Ile Gly Gly Ala Pro Pro Glu
            340                 345                 350

Ile Leu Gln Ser Arg Ala Leu Arg Ala His Leu Pro Leu Asp Ile Asn
        355                 360                 365

Phe Arg Gly Cys Met Lys Gly Phe Gln Phe Gln Lys Lys Asp Phe Asn
    370                 375                 380

Leu Leu Glu Gln Thr Glu Thr Leu Gly Val Gly Tyr Gly Cys Pro Glu
385                 390                 395                 400

Asp Ser Leu Ile Ser Arg Arg Ala Tyr Phe Asn Gly Gln Ser Phe Ile
                405                 410                 415

Ala Ser Ile Gln Lys Ile Ser Phe Phe Asp Gly Phe Glu Gly Gly Phe
            420                 425                 430

Asn Phe Arg Thr Leu Gln Pro Asn Gly Leu Leu Phe Tyr Tyr Ala Ser
        435                 440                 445

Gly Ser Asp Val Phe Ser Ile Ser Leu Asp Asn Gly Thr Val Ile Met
    450                 455                 460

Asp Val Lys Gly Ile Lys Val Gln Ser Val Asp Lys Gln Tyr Asn Asp
465                 470                 475                 480

Gly Leu Ser His Phe Val Ile Ser Ser Val Ser Pro Thr Arg Tyr Glu
                485                 490                 495

Leu Ile Val Asp Lys Ser Arg Val Gly Ser Lys Asn Pro Thr Lys Gly
            500                 505                 510

Lys Ile Glu Gln Thr Gln Ala Ser Glu Lys Lys Phe Tyr Phe Gly Gly
        515                 520                 525

Ser Pro Ile Ser Ala Gln Tyr Ala Asn Phe Thr Gly Cys Ile Ser Asn
    530                 535                 540

Ala Tyr Phe Thr Arg Val Asp Arg Asp Val Glu Val Glu Asp Phe Gln
545                 550                 555                 560

Arg Tyr Thr Glu Lys Val His Thr Ser Leu Tyr Glu Cys Pro Ile Glu
                565                 570                 575

Ser Ser Pro Leu Phe Leu Leu His Lys Lys Gly Lys Asn Leu Ser Lys
            580                 585                 590

Pro Lys Ala Ser Gln Asn Lys Lys Gly Gly Lys Ser Lys Asp Ala Pro
        595                 600                 605

Ser Trp Asp Pro Val Ala Leu Lys Leu Pro Glu Arg Asn Thr Pro Arg
    610                 615                 620

Asn Ser His Cys His Leu Ser Asn Ser Pro Arg Ala Ile Glu His Ala
625                 630                 635                 640

Tyr Gln Tyr Gly Gly Thr Ala Asn Ser Arg Gln Glu Phe Glu His Leu
                645                 650                 655

Lys Gly Asp Phe Gly Ala Lys Ser Gln Phe Ser Ile Arg Leu Arg Thr
            660                 665                 670

Arg Ser Ser His Gly Met Ile Phe Tyr Val Ser Asp Gln Glu Glu Asn
        675                 680                 685

Asp Phe Met Thr Leu Phe Leu Ala His Gly Arg Leu Val Tyr Met Phe
```

```
                690             695             700
Asn Val Gly His Lys Lys Leu Lys Ile Arg Ser Gln Glu Lys Tyr Asn
705             710             715             720

Asp Gly Leu Trp His Asp Val Ile Phe Ile Arg Glu Arg Ser Ser Gly
            725             730             735

Arg Leu Val Ile Asp Gly Leu Arg Val Leu Glu Glu Ser Leu Pro Pro
            740             745             750

Thr Glu Ala Thr Trp Lys Ile Lys Gly Pro Ile Tyr Leu Gly Gly Val
            755             760             765

Ala Pro Gly Lys Ala Val Lys Asn Val Gln Ile Asn Ser Ile Tyr Ser
770             775             780

Phe Ser Gly Cys Leu Ser Asn Leu Gln Leu Asn Gly Ala Ser Ile Thr
785             790             795             800

Ser Ala Ser Gln Thr Phe Ser Val Thr Pro Cys Phe Glu Gly Pro Met
            805             810             815

Glu Thr Gly Thr Tyr Phe Ser Thr Glu Gly Gly Tyr Val Val Leu Asp
            820             825             830

Glu Ser Phe Asn Ile Gly Leu Lys Phe Glu Ile Ala Phe Glu Val Arg
            835             840             845

Pro Arg Ser Ser Ser Gly Thr Leu Val His Gly His Ser Val Asn Gly
850             855             860

Glu Tyr Leu Asn Val His Met Lys Asn Gly Gln Val Ile Val Lys Val
865             870             875             880

Asn Asn Gly Ile Arg Asp Phe Ser Thr Ser Val Thr Pro Lys Gln Ser
            885             890             895

Leu Cys Asp Gly Arg Trp His Arg Ile Thr Val Ile Arg Asp Ser Asn
            900             905             910

Val Val Gln Leu Asp Val Asp Ser Glu Val Asn His Val Val Gly Pro
            915             920             925

Leu Asn Pro Lys Pro Ile Asp His Arg Glu Pro Val Phe Val Gly Gly
            930             935             940

Val Pro Glu Ser Leu Leu Thr Pro Arg Leu Ala Pro Ser Lys Pro Phe
945             950             955             960

Thr Gly Cys Ile Arg His Phe Val Ile Asp Gly His Pro Val Ser Phe
            965             970             975

Ser Lys Ala Ala Leu Val Ser Gly Ala Val Ser Ile Asn Ser Cys Pro
            980             985             990

<210> SEQ ID NO 5
<211> LENGTH: 206
<212> TYPE: PRT
<213> ORGANISM: Artificial Sequence
<220> FEATURE:
<223> OTHER INFORMATION: LG1 module of G domain of human LAMA4

<400> SEQUENCE: 5

Ser Lys Ile Gln Val Ser Met Met Phe Asp Gly Gln Ser Ala Val Glu
1               5               10              15

Val His Ser Arg Thr Ser Met Asp Asp Leu Lys Ala Phe Thr Ser Leu
            20              25              30

Ser Leu Tyr Met Lys Pro Pro Val Lys Arg Pro Glu Leu Thr Glu Thr
            35              40              45

Ala Asp Gln Phe Ile Leu Tyr Leu Gly Ser Lys Asn Ala Lys Lys Glu
50              55              60

Tyr Met Gly Leu Ala Ile Lys Asn Asp Asn Leu Val Tyr Val Tyr Asn
```

```
                65                  70                  75                  80
Leu Gly Thr Lys Asp Val Glu Ile Pro Leu Asp Ser Lys Pro Val Ser
                85                  90                  95

Ser Trp Pro Ala Tyr Phe Ser Ile Val Lys Ile Glu Arg Val Gly Lys
                100                 105                 110

His Gly Lys Val Phe Leu Thr Val Pro Ser Leu Ser Ser Thr Ala Glu
                115                 120                 125

Glu Lys Phe Ile Lys Lys Gly Glu Phe Ser Gly Asp Asp Ser Leu Leu
                130                 135                 140

Asp Leu Asp Pro Glu Asp Thr Val Phe Tyr Val Gly Gly Val Pro Ser
145                 150                 155                 160

Asn Phe Lys Leu Pro Thr Ser Leu Asn Leu Pro Gly Phe Val Gly Cys
                165                 170                 175

Leu Glu Leu Ala Thr Leu Asn Asn Asp Val Ile Ser Leu Tyr Asn Phe
                180                 185                 190

Lys His Ile Tyr Asn Met Asp Pro Ser Thr Ser Val Pro Cys
                195                 200                 205

<210> SEQ ID NO 6
<211> LENGTH: 180
<212> TYPE: PRT
<213> ORGANISM: Artificial Sequence
<220> FEATURE:
<223> OTHER INFORMATION: LG2 module of G domain of human LAMA4

<400> SEQUENCE: 6

Ala Ser Tyr Phe Phe Asp Gly Ser Gly Tyr Ala Val Val Arg Asp Ile
1               5                   10                  15

Thr Arg Arg Gly Lys Phe Gly Gln Val Thr Arg Phe Asp Ile Glu Val
                20                  25                  30

Arg Thr Pro Ala Asp Asn Gly Leu Ile Leu Met Val Asn Gly Ser
                35                  40                  45

Met Phe Phe Arg Leu Glu Met Arg Asn Gly Tyr Leu His Val Phe Tyr
                50                  55                  60

Asp Phe Gly Phe Ser Ser Gly Arg Val His Leu Glu Asp Thr Leu Lys
65                  70                  75                  80

Lys Ala Gln Ile Asn Asp Ala Lys Tyr His Glu Ile Ser Ile Ile Tyr
                85                  90                  95

His Asn Asp Lys Lys Met Ile Leu Val Val Asp Arg Arg His Val Lys
                100                 105                 110

Ser Met Asp Asn Glu Lys Met Lys Ile Pro Phe Thr Asp Ile Tyr Ile
                115                 120                 125

Gly Gly Ala Pro Pro Glu Ile Leu Gln Ser Arg Ala Leu Arg Ala His
                130                 135                 140

Leu Pro Leu Asp Ile Asn Phe Arg Gly Cys Met Lys Gly Phe Gln Phe
145                 150                 155                 160

Gln Lys Lys Asp Phe Asn Leu Leu Glu Gln Thr Glu Thr Leu Gly Val
                165                 170                 175

Gly Tyr Gly Cys
                180

<210> SEQ ID NO 7
<211> LENGTH: 169
<212> TYPE: PRT
<213> ORGANISM: Artificial Sequence
<220> FEATURE:
<223> OTHER INFORMATION: LG3 module of G domain of human LAMA4
```

<400> SEQUENCE: 7

```
Ser Arg Arg Ala Tyr Phe Asn Gly Gln Ser Phe Ile Ala Ser Ile Gln
1               5                   10                  15

Lys Ile Ser Phe Phe Asp Gly Phe Glu Gly Gly Phe Asn Phe Arg Thr
            20                  25                  30

Leu Gln Pro Asn Gly Leu Leu Phe Tyr Tyr Ala Ser Gly Ser Asp Val
        35                  40                  45

Phe Ser Ile Ser Leu Asp Asn Gly Thr Val Ile Met Asp Val Lys Gly
    50                  55                  60

Ile Lys Val Gln Ser Val Asp Lys Gln Tyr Asn Asp Gly Leu Ser His
65                  70                  75                  80

Phe Val Ile Ser Ser Val Ser Pro Thr Arg Tyr Glu Leu Ile Val Asp
                85                  90                  95

Lys Ser Arg Val Gly Ser Lys Asn Pro Thr Lys Gly Lys Ile Glu Gln
            100                 105                 110

Thr Gln Ala Ser Glu Lys Lys Phe Tyr Phe Gly Gly Ser Pro Ile Ser
        115                 120                 125

Ala Gln Tyr Ala Asn Phe Thr Gly Cys Ile Ser Asn Ala Tyr Phe Thr
    130                 135                 140

Arg Val Asp Arg Asp Val Glu Val Glu Asp Phe Gln Arg Tyr Thr Glu
145                 150                 155                 160

Lys Val His Thr Ser Leu Tyr Glu Cys
                165
```

<210> SEQ ID NO 8
<211> LENGTH: 601
<212> TYPE: PRT
<213> ORGANISM: Artificial Sequence
<220> FEATURE:
<223> OTHER INFORMATION: LG1-3 modules of G domain of human LAMA4

<400> SEQUENCE: 8

```
Ser Lys Ile Gln Val Ser Met Met Phe Asp Gly Gln Ser Ala Val Glu
1               5                   10                  15

Val His Ser Arg Thr Ser Met Asp Asp Leu Lys Ala Phe Thr Ser Leu
            20                  25                  30

Ser Leu Tyr Met Lys Pro Pro Val Lys Arg Pro Glu Leu Thr Glu Thr
        35                  40                  45

Ala Asp Gln Phe Ile Leu Tyr Leu Gly Ser Lys Asn Ala Lys Lys Glu
    50                  55                  60

Tyr Met Gly Leu Ala Ile Lys Asn Asp Asn Leu Val Tyr Val Tyr Asn
65                  70                  75                  80

Leu Gly Thr Lys Asp Val Glu Ile Pro Leu Asp Ser Lys Pro Val Ser
                85                  90                  95

Ser Trp Pro Ala Tyr Phe Ser Ile Val Lys Ile Glu Arg Val Gly Lys
            100                 105                 110

His Gly Lys Val Phe Leu Thr Val Pro Ser Leu Ser Ser Thr Ala Glu
        115                 120                 125

Glu Lys Phe Ile Lys Lys Gly Glu Phe Ser Gly Asp Asp Ser Leu Leu
    130                 135                 140

Asp Leu Asp Pro Glu Asp Thr Val Phe Tyr Val Gly Gly Val Pro Ser
145                 150                 155                 160

Asn Phe Lys Leu Pro Thr Ser Leu Asn Leu Pro Gly Phe Val Gly Cys
                165                 170                 175
```

```
Leu Glu Leu Ala Thr Leu Asn Asn Asp Val Ile Ser Leu Tyr Asn Phe
            180                 185                 190

Lys His Ile Tyr Asn Met Asp Pro Ser Thr Ser Val Pro Cys Ala Arg
            195                 200                 205

Asp Lys Leu Ala Phe Thr Gln Ser Arg Ala Ala Ser Tyr Phe Phe Asp
            210                 215                 220

Gly Ser Gly Tyr Ala Val Val Arg Asp Ile Thr Arg Arg Gly Lys Phe
225                 230                 235                 240

Gly Gln Val Thr Arg Phe Asp Ile Glu Val Arg Thr Pro Ala Asp Asn
            245                 250                 255

Gly Leu Ile Leu Leu Met Val Asn Gly Ser Met Phe Phe Arg Leu Glu
            260                 265                 270

Met Arg Asn Gly Tyr Leu His Val Phe Tyr Asp Phe Gly Phe Ser Ser
            275                 280                 285

Gly Arg Val His Leu Glu Asp Thr Leu Lys Lys Ala Gln Ile Asn Asp
            290                 295                 300

Ala Lys Tyr His Glu Ile Ser Ile Ile Tyr His Asn Asp Lys Lys Met
305                 310                 315                 320

Ile Leu Val Val Asp Arg Arg His Val Lys Ser Met Asp Asn Glu Lys
            325                 330                 335

Met Lys Ile Pro Phe Thr Asp Ile Tyr Ile Gly Gly Ala Pro Pro Glu
            340                 345                 350

Ile Leu Gln Ser Arg Ala Leu Arg Ala His Leu Pro Leu Asp Ile Asn
            355                 360                 365

Phe Arg Gly Cys Met Lys Gly Phe Gln Phe Gln Lys Lys Asp Phe Asn
            370                 375                 380

Leu Leu Glu Gln Thr Glu Thr Leu Gly Val Gly Tyr Gly Cys Pro Glu
385                 390                 395                 400

Asp Ser Leu Ile Ser Arg Arg Ala Tyr Phe Asn Gly Gln Ser Phe Ile
            405                 410                 415

Ala Ser Ile Gln Lys Ile Ser Phe Phe Asp Gly Phe Glu Gly Gly Phe
            420                 425                 430

Asn Phe Arg Thr Leu Gln Pro Asn Gly Leu Leu Phe Tyr Tyr Ala Ser
            435                 440                 445

Gly Ser Asp Val Phe Ser Ile Ser Leu Asp Asn Gly Thr Val Ile Met
450                 455                 460

Asp Val Lys Gly Ile Lys Val Gln Ser Val Asp Lys Gln Tyr Asn Asp
465                 470                 475                 480

Gly Leu Ser His Phe Val Ile Ser Ser Val Ser Pro Thr Arg Tyr Glu
            485                 490                 495

Leu Ile Val Asp Lys Ser Arg Val Gly Ser Lys Asn Pro Thr Lys Gly
            500                 505                 510

Lys Ile Glu Gln Thr Gln Ala Ser Glu Lys Lys Phe Tyr Phe Gly Gly
            515                 520                 525

Ser Pro Ile Ser Ala Gln Tyr Ala Asn Phe Thr Gly Cys Ile Ser Asn
            530                 535                 540

Ala Tyr Phe Thr Arg Val Asp Arg Asp Val Glu Val Glu Asp Phe Gln
545                 550                 555                 560

Arg Tyr Thr Glu Lys Val His Thr Ser Leu Tyr Glu Cys Pro Ile Glu
            565                 570                 575

Ser Ser Pro Leu Phe Leu Leu His Lys Lys Gly Lys Asn Leu Ser Lys
            580                 585                 590

Pro Lys Ala Ser Gln Asn Lys Lys Gly
```

```
              595                 600

<210> SEQ ID NO 9
<211> LENGTH: 171
<212> TYPE: PRT
<213> ORGANISM: Artificial Sequence
<220> FEATURE:
<223> OTHER INFORMATION: LG4 module of G domain of human LAMA4

<400> SEQUENCE: 9

Tyr Gln Tyr Gly Gly Thr Ala Asn Ser Arg Gln Glu Phe Glu His Leu
1               5                   10                  15

Lys Gly Asp Phe Gly Ala Lys Ser Gln Phe Ser Ile Arg Leu Arg Thr
            20                  25                  30

Arg Ser Ser His Gly Met Ile Phe Tyr Val Ser Asp Gln Glu Glu Asn
        35                  40                  45

Asp Phe Met Thr Leu Phe Leu Ala His Gly Arg Leu Val Tyr Met Phe
    50                  55                  60

Asn Val Gly His Lys Lys Leu Lys Ile Arg Ser Gln Glu Lys Tyr Asn
65                  70                  75                  80

Asp Gly Leu Trp His Asp Val Ile Phe Ile Arg Glu Arg Ser Ser Gly
                85                  90                  95

Arg Leu Val Ile Asp Gly Leu Arg Val Leu Glu Glu Ser Leu Pro Pro
            100                 105                 110

Thr Glu Ala Thr Trp Lys Ile Lys Gly Pro Ile Tyr Leu Gly Gly Val
        115                 120                 125

Ala Pro Gly Lys Ala Val Lys Asn Val Gln Ile Asn Ser Ile Tyr Ser
    130                 135                 140

Phe Ser Gly Cys Leu Ser Asn Leu Gln Leu Asn Gly Ala Ser Ile Thr
145                 150                 155                 160

Ser Ala Ser Gln Thr Phe Ser Val Thr Pro Cys
                165                 170

<210> SEQ ID NO 10
<211> LENGTH: 174
<212> TYPE: PRT
<213> ORGANISM: Artificial Sequence
<220> FEATURE:
<223> OTHER INFORMATION: LG5 module of G domain of human LAMA4

<400> SEQUENCE: 10

Thr Gly Thr Tyr Phe Ser Thr Glu Gly Gly Tyr Val Val Leu Asp Glu
1               5                   10                  15

Ser Phe Asn Ile Gly Leu Lys Phe Glu Ile Ala Phe Glu Val Arg Pro
            20                  25                  30

Arg Ser Ser Ser Gly Thr Leu Val His Gly His Ser Val Asn Gly Glu
        35                  40                  45

Tyr Leu Asn Val His Met Lys Asn Gly Gln Val Ile Val Lys Val Asn
    50                  55                  60

Asn Gly Ile Arg Asp Phe Ser Thr Ser Val Thr Pro Lys Gln Ser Leu
65                  70                  75                  80

Cys Asp Gly Arg Trp His Arg Ile Thr Val Ile Arg Asp Ser Asn Val
                85                  90                  95

Val Gln Leu Asp Val Asp Ser Glu Val Asn His Val Val Gly Pro Leu
            100                 105                 110

Asn Pro Lys Pro Ile Asp His Arg Glu Pro Val Phe Val Gly Gly Val
        115                 120                 125
```

```
Pro Glu Ser Leu Leu Thr Pro Arg Leu Ala Pro Ser Lys Pro Phe Thr
    130                 135                 140

Gly Cys Ile Arg His Phe Val Ile Asp Gly His Pro Val Ser Phe Ser
145                 150                 155                 160

Lys Ala Ala Leu Val Ser Gly Ala Val Ser Ile Asn Ser Cys
                165                 170

<210> SEQ ID NO 11
<211> LENGTH: 369
<212> TYPE: PRT
<213> ORGANISM: Artificial Sequence
<220> FEATURE:
<223> OTHER INFORMATION: LG4-5 modules of G domain of human LAMA4

<400> SEQUENCE: 11

Arg Asn Ser His Cys His Leu Ser Asn Ser Pro Arg Ala Ile Glu His
1               5                   10                  15

Ala Tyr Gln Tyr Gly Gly Thr Ala Asn Ser Arg Gln Glu Phe Glu His
                20                  25                  30

Leu Lys Gly Asp Phe Gly Ala Lys Ser Gln Phe Ser Ile Arg Leu Arg
            35                  40                  45

Thr Arg Ser Ser His Gly Met Ile Phe Tyr Val Ser Asp Gln Glu Glu
        50                  55                  60

Asn Asp Phe Met Thr Leu Phe Leu Ala His Gly Arg Leu Val Tyr Met
65                  70                  75                  80

Phe Asn Val Gly His Lys Lys Leu Lys Ile Arg Ser Gln Glu Lys Tyr
                85                  90                  95

Asn Asp Gly Leu Trp His Asp Val Ile Phe Ile Arg Glu Arg Ser Ser
                100                 105                 110

Gly Arg Leu Val Ile Asp Gly Leu Arg Val Leu Glu Glu Ser Leu Pro
            115                 120                 125

Pro Thr Glu Ala Thr Trp Lys Ile Lys Gly Pro Ile Tyr Leu Gly Gly
        130                 135                 140

Val Ala Pro Gly Lys Ala Val Lys Asn Val Gln Ile Asn Ser Ile Tyr
145                 150                 155                 160

Ser Phe Ser Gly Cys Leu Ser Asn Leu Gln Leu Asn Gly Ala Ser Ile
                165                 170                 175

Thr Ser Ala Ser Gln Thr Phe Ser Val Thr Pro Cys Phe Glu Gly Pro
                180                 185                 190

Met Glu Thr Gly Thr Tyr Phe Ser Thr Glu Gly Gly Tyr Val Val Leu
                195                 200                 205

Asp Glu Ser Phe Asn Ile Gly Leu Lys Phe Glu Ile Ala Phe Glu Val
            210                 215                 220

Arg Pro Arg Ser Ser Gly Thr Leu Val His Gly His Ser Val Asn
225                 230                 235                 240

Gly Glu Tyr Leu Asn Val His Met Lys Asn Gly Gln Val Ile Val Lys
                245                 250                 255

Val Asn Asn Gly Ile Arg Asp Phe Ser Thr Ser Val Thr Pro Lys Gln
                260                 265                 270

Ser Leu Cys Asp Gly Arg Trp His Arg Ile Thr Val Ile Arg Asp Ser
            275                 280                 285

Asn Val Val Gln Leu Asp Val Asp Ser Glu Val Asn His Val Val Gly
        290                 295                 300

Pro Leu Asn Pro Lys Pro Ile Asp His Arg Glu Pro Val Phe Val Gly
305                 310                 315                 320
```

-continued

Gly Val Pro Glu Ser Leu Leu Thr Pro Arg Leu Ala Pro Ser Lys Pro
            325                 330                 335

Phe Thr Gly Cys Ile Arg His Phe Val Ile Asp Gly His Pro Val Ser
            340                 345                 350

Phe Ser Lys Ala Ala Leu Val Ser Gly Ala Val Ser Ile Asn Ser Cys
            355                 360                 365

Pro

<210> SEQ ID NO 12
<211> LENGTH: 310
<212> TYPE: PRT
<213> ORGANISM: Homo sapiens

<400> SEQUENCE: 12

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Ala Thr Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 13
<211> LENGTH: 201
<212> TYPE: PRT
<213> ORGANISM: Homo sapiens

<400> SEQUENCE: 13

```
Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

His Leu Ser Asp Ser Glu Arg Lys Met Asp Pro Ala Glu Glu Asp Thr
        115                 120                 125

Asn Val Tyr Thr Glu Lys His Ser Asp Ser Leu Phe Lys Arg Thr Glu
    130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
                165                 170                 175

Gly Ser Tyr Asp Leu Gly Glu Arg Lys Pro Ser Ser Ala Ala Tyr Gln
            180                 185                 190

Lys Ala Pro Thr Lys Glu Phe Tyr Ala
        195                 200
```

<210> SEQ ID NO 14
<211> LENGTH: 442
<212> TYPE: PRT
<213> ORGANISM: Homo sapiens

<400> SEQUENCE: 14

```
Met Lys Pro Gly Pro Pro His Arg Ala Gly Ala Ala His Gly Ala Gly
1               5                   10                  15

Ala Gly Ala Gly Ala Ala Ala Gly Pro Gly Ala Arg Gly Leu Leu Leu
            20                  25                  30

Pro Pro Leu Leu Leu Leu Leu Leu Ala Gly Arg Ala Ala Gly Ala Gln
        35                  40                  45

Arg Trp Arg Ser Glu Asn Phe Glu Arg Pro Val Asp Leu Glu Gly Ser
    50                  55                  60

Gly Asp Asp Asp Ser Phe Pro Asp Asp Glu Leu Asp Asp Leu Tyr Ser
65                  70                  75                  80

Gly Ser Gly Ser Gly Tyr Phe Glu Gln Glu Ser Gly Ile Glu Thr Ala
                85                  90                  95

Met Arg Phe Ser Pro Asp Val Ala Leu Ala Val Ser Thr Thr Pro Ala
            100                 105                 110

Val Leu Pro Thr Thr Asn Ile Gln Pro Val Gly Thr Pro Phe Glu Glu
        115                 120                 125
```

```
Leu Pro Ser Glu Arg Pro Thr Leu Glu Pro Ala Thr Ser Pro Leu Val
            130                 135                 140

Val Thr Glu Val Pro Glu Pro Ser Gln Arg Ala Thr Thr Val Ser
145                 150                 155                 160

Thr Thr Met Ala Thr Ala Ala Thr Ser Thr Gly Asp Pro Thr Val
                165                 170                 175

Ala Thr Val Pro Ala Thr Val Ala Thr Ala Thr Pro Ser Thr Pro Ala
                180                 185                 190

Ala Pro Pro Phe Thr Ala Thr Thr Ala Val Ile Arg Thr Gly Val
                195                 200                 205

Arg Arg Leu Leu Pro Leu Pro Leu Thr Thr Val Ala Thr Ala Arg Ala
210                 215                 220

Thr Thr Pro Glu Ala Pro Ser Pro Pro Thr Thr Ala Ala Val Leu Asp
225                 230                 235                 240

Thr Glu Ala Pro Thr Pro Arg Leu Val Ser Thr Ala Thr Ser Arg Pro
                245                 250                 255

Arg Ala Leu Pro Arg Pro Ala Thr Thr Gln Glu Pro Asp Ile Pro Glu
                260                 265                 270

Arg Ser Thr Leu Pro Leu Gly Thr Thr Ala Pro Gly Pro Thr Glu Val
                275                 280                 285

Ala Gln Thr Pro Thr Pro Glu Thr Phe Leu Thr Thr Ile Arg Asp Glu
                290                 295                 300

Pro Glu Val Pro Val Ser Gly Gly Pro Ser Gly Asp Phe Glu Leu Pro
305                 310                 315                 320

Glu Glu Glu Thr Thr Gln Pro Asp Thr Ala Asn Glu Val Val Ala Val
                325                 330                 335

Gly Gly Ala Ala Ala Lys Ala Ser Ser Pro Pro Gly Thr Leu Pro Lys
                340                 345                 350

Gly Ala Arg Pro Gly Pro Gly Leu Leu Asp Asn Ala Ile Asp Ser Gly
                355                 360                 365

Ser Ser Ala Ala Gln Leu Pro Gln Lys Ser Ile Leu Glu Arg Lys Glu
                370                 375                 380

Val Leu Val Ala Val Ile Val Gly Gly Val Val Gly Ala Leu Phe Ala
385                 390                 395                 400

Ala Phe Leu Val Thr Leu Leu Ile Tyr Arg Met Lys Lys Lys Asp Glu
                405                 410                 415

Gly Ser Tyr Thr Leu Glu Glu Pro Lys Gln Ala Ser Val Thr Tyr Gln
                420                 425                 430

Lys Pro Asp Lys Gln Glu Glu Phe Tyr Ala
                435                 440

<210> SEQ ID NO 15
<211> LENGTH: 198
<212> TYPE: PRT
<213> ORGANISM: Homo sapiens

<400> SEQUENCE: 15

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
                20                  25                  30

Leu Glu Gly Arg Tyr Phe Ser Gly Ala Leu Pro Asp Asp Glu Asp Val
                35                  40                  45

Val Gly Pro Gly Gln Glu Ser Asp Asp Phe Glu Leu Ser Gly Ser Gly
                50                  55                  60
```

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
130                 135                 140

Glu Val Leu Ala Ala Leu Ile Val Gly Ile Val Gly Ile Leu Phe
145                 150                 155                 160

Ala Val Phe Leu Ile Leu Leu Met Tyr Arg Met Lys Lys Lys Asp
            165                 170                 175

Glu Gly Ser Tyr Asp Leu Gly Lys Lys Pro Ile Tyr Lys Lys Ala Pro
        180                 185                 190

Thr Asn Glu Phe Tyr Ala
        195

<210> SEQ ID NO 16
<211> LENGTH: 119
<212> TYPE: PRT
<213> ORGANISM: Artificial Sequence
<220> FEATURE:
<223> OTHER INFORMATION: 15F7 mature heavy chain variable region

<400> SEQUENCE: 16

Gln Val Gln Leu Gln Gln Ser Gly Thr Glu Leu Ala Arg Pro Gly Ala
1               5                   10                  15

Ala Val Lys Leu Ser Cys Lys Ala Ser Gly Tyr Thr Phe Thr Ser Tyr
            20                  25                  30

Gly Leu Ser Trp Val Lys Gln Arg Ala Gly Gln Gly Leu Glu Trp Ile
        35                  40                  45

Gly Glu Ile Phe Pro Arg Ser Gly Asn Thr Tyr Tyr Asn Glu Lys Phe
50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
            85                  90                  95

Ala Arg Gly Val Arg Ser Pro Gly Ala Met Asp Tyr Trp Gly Gln Gly
        100                 105                 110

Thr Ser Val Thr Val Ser Ser
        115

<210> SEQ ID NO 17
<211> LENGTH: 108
<212> TYPE: PRT
<213> ORGANISM: Artificial Sequence
<220> FEATURE:
<223> OTHER INFORMATION: 15F7 mature light chain variable region

<400> SEQUENCE: 17

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile

```
                    35                  40                  45
Ser Gly Ala Thr Ser Leu Glu Thr Gly Val Pro Ser Arg Phe Ser Gly
            50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ile Pro Tyr
                85                  90                  95

Thr Phe Gly Gly Gly Thr Asn Leu Glu Ile Lys Arg
            100                 105

<210> SEQ ID NO 18
<211> LENGTH: 19
<212> TYPE: PRT
<213> ORGANISM: Artificial Sequence
<220> FEATURE:
<223> OTHER INFORMATION: 15F7 heavy chain variable region signal peptide

<400> SEQUENCE: 18

Met Glu Trp Ile Trp Ser Phe Leu Phe Ile Leu Ser Gly Thr Ala Gly
1               5                   10                  15

Val Gln Ser

<210> SEQ ID NO 19
<211> LENGTH: 27
<212> TYPE: PRT
<213> ORGANISM: Artificial Sequence
<220> FEATURE:
<223> OTHER INFORMATION: 15F7 light chain variable region signal peptide

<400> SEQUENCE: 19

Met Ser Ser His Ser Arg Asn Met Lys Phe Pro Ser Gln Leu Leu Leu
1               5                   10                  15

Leu Leu Leu Phe Gly Ile Pro Gly Met Ile Cys
            20                  25

<210> SEQ ID NO 20
<211> LENGTH: 5
<212> TYPE: PRT
<213> ORGANISM: Artificial Sequence
<220> FEATURE:
<223> OTHER INFORMATION: 15F7 CDR-H1

<400> SEQUENCE: 20

Ser Tyr Gly Leu Ser
1               5

<210> SEQ ID NO 21
<211> LENGTH: 17
<212> TYPE: PRT
<213> ORGANISM: Artificial Sequence
<220> FEATURE:
<223> OTHER INFORMATION: 15F7 CDR-H2

<400> SEQUENCE: 21

Glu Ile Phe Pro Arg Ser Gly Asn Thr Tyr Tyr Asn Glu Lys Phe Lys
1               5                   10                  15

Gly

<210> SEQ ID NO 22
<211> LENGTH: 10
<212> TYPE: PRT
<213> ORGANISM: Artificial Sequence
<220> FEATURE:
```

<223> OTHER INFORMATION: 15F7 CDR-H3

<400> SEQUENCE: 22

Gly Val Arg Ser Pro Gly Ala Met Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: 15F7 CDR-L1

<400> SEQUENCE: 23

Lys Ala Ser Glu Asp Ile Tyr Asn Arg Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: 15F7 CDR-L2

<400> SEQUENCE: 24

Gly Ala Thr Ser Leu Glu Thr
1               5

<210> SEQ ID NO 25
<211> LENGTH: 9
<212> TYPE: PRT
<213> ORGANISM: Artificial Sequence
<220> FEATURE:
<223> OTHER INFORMATION: 15F7 CDR-L3

<400> SEQUENCE: 25

Gln Gln Tyr Trp Ser Ile Pro Tyr Thr
1               5

<210> SEQ ID NO 26
<211> LENGTH: 119
<212> TYPE: PRT
<213> ORGANISM: Artificial Sequence
<220> FEATURE:
<223> OTHER INFORMATION: 6C12 mature heavy chain variable region

<400> SEQUENCE: 26

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
                20                  25                  30

Trp Met His Trp Val Lys Gln Arg Pro Gly Gln Gly Pro Glu Trp Ile
            35                  40                  45

Gly Met Ile His Pro Tyr Ser Gly Ala Ile Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Val Lys Gln Leu Arg Leu Leu Tyr Tyr Phe Asp Tyr Trp Gly Gln Gly
                100                 105                 110

Thr Thr Leu Thr Val Ser Ser
            115

```
<210> SEQ ID NO 27
<211> LENGTH: 114
<212> TYPE: PRT
<213> ORGANISM: Artificial Sequence
<220> FEATURE:
<223> OTHER INFORMATION: 6C12 mature light chain variable region, v1

<400> SEQUENCE: 27

Asp Ile Val Met Thr Gln Ser Pro Ser Ser Leu Thr Val Thr Ala Gly
1               5                   10                  15

Glu Lys Val Thr Met Ser Cys Lys Ser Arg Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg

<210> SEQ ID NO 28
<211> LENGTH: 19
<212> TYPE: PRT
<213> ORGANISM: Artificial Sequence
<220> FEATURE:
<223> OTHER INFORMATION: 6C12 heavy chain variable region signal peptide

<400> SEQUENCE: 28

Met Gly Trp Ser Tyr Ile Ile Leu Phe Leu Val Ala Thr Ala Thr Gly
1               5                   10                  15

Val His Ser

<210> SEQ ID NO 29
<211> LENGTH: 20
<212> TYPE: PRT
<213> ORGANISM: Artificial Sequence
<220> FEATURE:
<223> OTHER INFORMATION: 6C12 light chain variable region signal peptide

<400> SEQUENCE: 29

Met Glu Ser Gln Thr Gln Val Leu Met Ser Leu Leu Phe Trp Val Ser
1               5                   10                  15

Gly Thr Cys Gly
            20

<210> SEQ ID NO 30
<211> LENGTH: 5
<212> TYPE: PRT
<213> ORGANISM: Artificial Sequence
<220> FEATURE:
<223> OTHER INFORMATION: 6C12 CDR-H1

<400> SEQUENCE: 30

Thr Tyr Trp Met His
1               5
```

```
<210> SEQ ID NO 31
<211> LENGTH: 17
<212> TYPE: PRT
<213> ORGANISM: Artificial Sequence
<220> FEATURE:
<223> OTHER INFORMATION: 6C12 CDR-H2

<400> SEQUENCE: 31

Met Ile His Pro Tyr Ser Gly Ala Ile Asn Tyr Asn Glu Lys Phe Lys
1               5                   10                  15
Ser

<210> SEQ ID NO 32
<211> LENGTH: 10
<212> TYPE: PRT
<213> ORGANISM: Artificial Sequence
<220> FEATURE:
<223> OTHER INFORMATION: 6C12 CDR-H3

<400> SEQUENCE: 32

Gln Leu Arg Leu Leu Tyr Tyr Phe Asp Tyr
1               5                   10

<210> SEQ ID NO 33
<211> LENGTH: 17
<212> TYPE: PRT
<213> ORGANISM: Artificial Sequence
<220> FEATURE:
<223> OTHER INFORMATION: 6C12 CDR-L1, v1

<400> SEQUENCE: 33

Lys Ser Arg Gln Ser Leu Leu Asn Ser Gly Asn Gln Lys Asn Tyr Leu
1               5                   10                  15
Thr

<210> SEQ ID NO 34
<211> LENGTH: 7
<212> TYPE: PRT
<213> ORGANISM: Artificial Sequence
<220> FEATURE:
<223> OTHER INFORMATION: 6C12 CDR-L2

<400> SEQUENCE: 34

Trp Ala Ser Thr Arg Glu Ser
1               5

<210> SEQ ID NO 35
<211> LENGTH: 9
<212> TYPE: PRT
<213> ORGANISM: Artificial Sequence
<220> FEATURE:
<223> OTHER INFORMATION: 6C12 CDR-L3

<400> SEQUENCE: 35

Gln Asn Asp Tyr Ser Tyr Pro Leu Thr
1               5

<210> SEQ ID NO 36
<211> LENGTH: 121
<212> TYPE: PRT
<213> ORGANISM: Artificial Sequence
<220> FEATURE:
<223> OTHER INFORMATION: 13G10 mature heavy chain variable region, v1

<400> SEQUENCE: 36

Gln Val Gln Leu Gln Gln Ser Gly Ala Glu Leu Ala Arg Pro Gly Ala
```

```
1               5                   10                  15
Ser Val Lys Leu Ser Cys Lys Ala Ser Gly Tyr Thr Phe Thr Asn Tyr
            20                  25                  30

Gly Ile Ser Trp Val Lys Gln Arg Thr Gly Gln Gly Leu Glu Trp Ile
            35                  40                  45

Gly Ala Ile Tyr Pro Arg Ser Gly Asn Thr Tyr Tyr Asn Glu Lys Phe
        50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Glu Arg Asp Tyr Gly Ser Ser Tyr Ala Leu Asp Tyr Trp Gly
                100                 105                 110

Gln Gly Thr Ser Val Thr Val Ser Ser
        115                 120
```

<210> SEQ ID NO 37
<211> LENGTH: 119
<212> TYPE: PRT
<213> ORGANISM: Artificial Sequence
<220> FEATURE:
<223> OTHER INFORMATION: 13G10 mature heavy chain variable region, v2

<400> SEQUENCE: 37

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Met Ile His Pro His Ser Gly Ser Thr Asn Tyr Asn Glu Lys Phe
        50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gln Leu Arg Leu Leu Tyr Tyr Phe Asp Tyr Trp Gly Gln Gly
                100                 105                 110

Thr Thr Leu Thr Val Ser Ser
        115
```

<210> SEQ ID NO 38
<211> LENGTH: 108
<212> TYPE: PRT
<213> ORGANISM: Artificial Sequence
<220> FEATURE:
<223> OTHER INFORMATION: 13G10 mature light chain variable region

<400> SEQUENCE: 38

```
Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Thr Gly
        50                  55                  60
```

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Pro Pro Arg
                85                  90                  95

Thr Phe Gly Gly Gly Thr Lys Leu Glu Ile Lys Arg
            100                 105

<210> SEQ ID NO 39
<211> LENGTH: 19
<212> TYPE: PRT
<213> ORGANISM: Artificial Sequence
<220> FEATURE:
<223> OTHER INFORMATION: 13G10 heavy chain variable region signal
      peptide, v1

<400> SEQUENCE: 39

Met Glu Trp Ile Trp Ile Phe Leu Phe Ile Leu Ser Gly Thr Ala Gly
1               5                   10                  15

Val Gln Ser

<210> SEQ ID NO 40
<211> LENGTH: 19
<212> TYPE: PRT
<213> ORGANISM: Artificial Sequence
<220> FEATURE:
<223> OTHER INFORMATION: 13G10 heavy chain variable region signal
      peptide, v2

<400> SEQUENCE: 40

Met Gly Trp Ser Tyr Ile Ile Leu Phe Leu Val Ala Thr Ala Thr Gly
1               5                   10                  15

Val His Ser

<210> SEQ ID NO 41
<211> LENGTH: 20
<212> TYPE: PRT
<213> ORGANISM: Artificial Sequence
<220> FEATURE:
<223> OTHER INFORMATION: 13G10 light chain variable region signal
      peptide

<400> SEQUENCE: 41

Met Lys Phe Pro Ser Gln Leu Leu Leu Leu Leu Phe Gly Ile Pro
1               5                   10                  15

Gly Met Ile Cys
            20

<210> SEQ ID NO 42
<211> LENGTH: 5
<212> TYPE: PRT
<213> ORGANISM: Artificial Sequence
<220> FEATURE:
<223> OTHER INFORMATION: 13G10 CDR-H1, v1

<400> SEQUENCE: 42

Asn Tyr Gly Ile Ser
1               5

<210> SEQ ID NO 43
<211> LENGTH: 17
<212> TYPE: PRT
<213> ORGANISM: Artificial Sequence
<220> FEATURE:
<223> OTHER INFORMATION: 13G10 CDR-H2, v1

```
<400> SEQUENCE: 43

Ala Ile Tyr Pro Arg Ser Gly Asn Thr Tyr Tyr Asn Glu Lys Phe Lys
1               5                   10                  15

Gly

<210> SEQ ID NO 44
<211> LENGTH: 12
<212> TYPE: PRT
<213> ORGANISM: Artificial Sequence
<220> FEATURE:
<223> OTHER INFORMATION: 13G10 CDR-H3, v1

<400> SEQUENCE: 44

Glu Arg Asp Tyr Gly Ser Ser Tyr Ala Leu Asp Tyr
1               5                   10

<210> SEQ ID NO 45
<211> LENGTH: 5
<212> TYPE: PRT
<213> ORGANISM: Artificial Sequence
<220> FEATURE:
<223> OTHER INFORMATION: 13G10 CDR-H1, v2

<400> SEQUENCE: 45

Ser Tyr Trp Met His
1               5

<210> SEQ ID NO 46
<211> LENGTH: 17
<212> TYPE: PRT
<213> ORGANISM: Artificial Sequence
<220> FEATURE:
<223> OTHER INFORMATION: 13G10 CDR-H2, v2

<400> SEQUENCE: 46

Met Ile His Pro His Ser Gly Ser Thr Asn Tyr Asn Glu Lys Phe Lys
1               5                   10                  15

Ser

<210> SEQ ID NO 47
<211> LENGTH: 10
<212> TYPE: PRT
<213> ORGANISM: Artificial Sequence
<220> FEATURE:
<223> OTHER INFORMATION: 13G10 CDR-H3, v2

<400> SEQUENCE: 47

Gln Leu Arg Leu Leu Tyr Tyr Phe Asp Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: 13G10 CDR-L1

<400> SEQUENCE: 48

Lys Ala Ser Glu Asp Ile Tyr Asn Arg Leu Ala
1               5                   10

<210> SEQ ID NO 49
<211> LENGTH: 7
<212> TYPE: PRT
<213> ORGANISM: Artificial Sequence
```

```
<220> FEATURE:
<223> OTHER INFORMATION: 13G10 CDR-L2

<400> SEQUENCE: 49

Gly Ala Thr Ser Leu Glu Thr
1               5

<210> SEQ ID NO 50
<211> LENGTH: 9
<212> TYPE: PRT
<213> ORGANISM: Artificial Sequence
<220> FEATURE:
<223> OTHER INFORMATION: 13G10 CDR-L3

<400> SEQUENCE: 50

Gln Gln Tyr Trp Ser Pro Pro Arg Thr
1               5

<210> SEQ ID NO 51
<211> LENGTH: 121
<212> TYPE: PRT
<213> ORGANISM: Artificial Sequence
<220> FEATURE:
<223> OTHER INFORMATION: Human VH acceptor FR, v1

<400> SEQUENCE: 51

Gln Val Gln Leu Val Gln Ser Gly Thr Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Val Gly Ile Gly Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Ala Val Asp Phe Asp Ser Ser Ser Tyr Ser Phe Trp Gly
            100                 105                 110

Gln Gly Thr Leu Val Thr Val Ser Ser
        115                 120

<210> SEQ ID NO 52
<211> LENGTH: 119
<212> TYPE: PRT
<213> ORGANISM: Artificial Sequence
<220> FEATURE:
<223> OTHER INFORMATION: Human VH acceptor FR, v2

<400> SEQUENCE: 52

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80
```

-continued

```
Met Glu Leu Ser Ser Leu Arg Ser Glu Asp Ser Ala Val Tyr Tyr Cys
            85                  90                  95

Ala Arg Asp Thr His Ser Trp Phe Ala Phe Asp Ile Trp Gly Gln Gly
            100                 105                 110

Thr Met Val Thr Val Ser Ser
        115

<210> SEQ ID NO 53
<211> LENGTH: 108
<212> TYPE: PRT
<213> ORGANISM: Artificial Sequence
<220> FEATURE:
<223> OTHER INFORMATION: Human VL acceptor FR, v1

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys Arg
            100                 105

<210> SEQ ID NO 54
<211> LENGTH: 108
<212> TYPE: PRT
<213> ORGANISM: Artificial Sequence
<220> FEATURE:
<223> OTHER INFORMATION: Human VL acceptor FR, v2

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Gln
                85                  90                  95

Thr Phe Gly Gly Gly Thr Lys Leu Glu Ile Lys Arg
            100                 105

<210> SEQ ID NO 55
<211> LENGTH: 119
<212> TYPE: PRT
<213> ORGANISM: Artificial Sequence
<220> FEATURE:
<223> OTHER INFORMATION: Synthetic
```

<400> SEQUENCE: 55

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Leu Ser Trp Val Arg Gln Ala Pro Gly Gln Gly Leu Glu Trp Met
        35                  40                  45

Gly Glu Ile Phe Pro Arg Ser Gly Asn Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Arg Ser Pro Gly Ala Met Asp Tyr Trp Gly Gln Gly
            100                 105                 110

Thr Leu Val Thr Val Ser Ser
        115

<210> SEQ ID NO 56
<211> LENGTH: 108
<212> TYPE: PRT
<213> ORGANISM: Artificial Sequence
<220> FEATURE:
<223> OTHER INFORMATION: Synthetic

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Ile Pro Tyr
                85                  90                  95

Thr Phe Gly Gly Gly Thr Lys Leu Glu Ile Lys Arg
            100                 105

<210> SEQ ID NO 57
<211> LENGTH: 119
<212> TYPE: PRT
<213> ORGANISM: Artificial Sequence
<220> FEATURE:
<223> OTHER INFORMATION: Synthetic

<400> SEQUENCE: 57

Glu Val Gln Leu Gln Gln Ser Gly Ala Glu Val Lys Lys Pro Gly Ser
1               5                   10                  15

Ser Val Lys Leu Ser Cys Lys Ala Ser Gly Tyr Thr Phe Thr Ser Tyr
            20                  25                  30

Gly Leu Ser Trp Val Lys Gln Arg Ala Gly Gln Gly Leu Glu Trp Ile
        35                  40                  45

Gly Glu Ile Phe Pro Arg Ser Gly Asn Thr Tyr Tyr Asn Glu Lys Phe
    50                  55                  60

```
Lys Gly Lys Ala Thr Leu Thr Ala Asp Lys Ser Ser Thr Ala Tyr
 65                  70                  75                  80

Met Glu Leu Arg Ser Leu Arg Ser Glu Asp Thr Ala Val Tyr Phe Cys
                 85                  90                  95

Ala Arg Gly Val Arg Ser Pro Gly Ala Met Asp Tyr Trp Gly Gln Gly
                100                 105                 110

Thr Leu Val Thr Val Ser Ser
            115
```

<210> SEQ ID NO 58
<211> LENGTH: 119
<212> TYPE: PRT
<213> ORGANISM: Artificial Sequence
<220> FEATURE:
<223> OTHER INFORMATION: Synthetic

<400> SEQUENCE: 58

```
Glu Val Gln Leu Gln Gln Ser Gly Ala Glu Val Lys Lys Pro Gly Ser
  1               5                  10                  15

Ser Val Lys Leu Ser Cys Lys Ala Ser Gly Tyr Thr Phe Thr Ser Tyr
                 20                  25                  30

Gly Leu Ser Trp Val Lys Gln Arg Pro Gly Gln Gly Leu Glu Trp Ile
             35                  40                  45

Gly Glu Ile Phe Pro Arg Ser Gly Asn Thr Tyr Tyr Asn Glu Lys Phe
         50                  55                  60

Lys Gly Lys Ala Thr Ile Thr Ala Asp Lys Ser Ser Thr Ala Tyr
 65                  70                  75                  80

Met Glu Leu Arg Ser Leu Arg Ser Glu Asp Thr Ala Val Tyr Phe Cys
                 85                  90                  95

Ala Arg Gly Val Arg Ser Pro Gly Ala Met Asp Tyr Trp Gly Gln Gly
                100                 105                 110

Thr Leu Val Thr Val Ser Ser
            115
```

<210> SEQ ID NO 59
<211> LENGTH: 108
<212> TYPE: PRT
<213> ORGANISM: Artificial Sequence
<220> FEATURE:
<223> OTHER INFORMATION: Synthetic

<400> SEQUENCE: 59

```
Asp Ile Gln Met Thr Gln Ser Ser Ser Ser Leu Ser Ala Ser Val Gly
  1               5                  10                  15

Asp Arg Val Thr Ile Thr Cys Lys Ala Ser Glu Asp Ile Tyr Asn Arg
                 20                  25                  30

Leu Ala Trp Tyr Gln Gln Lys Pro Gly Asn Ala Pro Arg Leu Leu Ile
             35                  40                  45

Ser Gly Ala Thr Ser Leu Glu Thr Gly Val Pro Ser Arg Phe Ser Gly
         50                  55                  60

Ser Gly Ser Gly Lys Asp Tyr Thr Leu Thr Ile Ser Ser Leu Gln Thr
 65                  70                  75                  80

Glu Asp Phe Ala Thr Tyr Tyr Cys Gln Gln Tyr Trp Ser Ile Pro Tyr
                 85                  90                  95

Thr Phe Gly Gly Gly Thr Lys Leu Glu Ile Lys Arg
            100                 105
```

<210> SEQ ID NO 60
<211> LENGTH: 108
<212> TYPE: PRT
<213> ORGANISM: Artificial Sequence
<220> FEATURE:
<223> OTHER INFORMATION: Synthetic

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Lys Leu Leu Ile
        35                  40                  45

Ser Gly Ala Thr Ser Leu Glu Thr Gly Val Pro Ser Arg Phe Ser Gly
50                  55                  60

Ser Gly Ser Gly Lys Asp Phe Thr Leu Thr Ile Ser Ser Leu Gln Pro
65                  70                  75                  80

Glu Asp Phe Ala Thr Tyr Tyr Cys Gln Gln Tyr Trp Ser Ile Pro Tyr
                85                  90                  95

Thr Phe Gly Gly Gly Thr Lys Val Glu Ile Lys Arg
            100                 105
```

<210> SEQ ID NO 61
<211> LENGTH: 330
<212> TYPE: PRT
<213> ORGANISM: Artificial Sequence
<220> FEATURE:
<223> OTHER INFORMATION: Exemplary human IgG1 constant region

<400> SEQUENCE: 61

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 62
<211> LENGTH: 106
<212> TYPE: PRT
<213> ORGANISM: Artificial Sequence
<220> FEATURE:
<223> OTHER INFORMATION: Exemplary human kappa light chain constant
      region without a N-terminal arginine

<400> SEQUENCE: 62

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 63
<211> LENGTH: 357
<212> TYPE: DNA
<213> ORGANISM: Artificial Sequence
<220> FEATURE:
<223> OTHER INFORMATION: 15F7 mature heavy chain variable region

<400> SEQUENCE: 63
caggttcagc tgcagcagtc tggaactgag ctggcgaggc ctggggctgc agtgaagctg      60
tcctgcaagg cttcaggcta taccttcaca agttatggtt taagctgggt gaagcagaga     120
gctggacagg gccttgagtg gattggagag attttcccta gaagtggtaa tacttactac     180
aatgagaagt tcaagggcaa ggccacactg actgcagaca atcctccag cacagcgtac     240 atggagctcc gcagcctgac atctgaggac tctgcggtct atttctgtgc aagaggggtt     300
cgtagccccg ggctatgga ctactgggt caaggaacct cagtcaccgt ctcctca         357
```

<210> SEQ ID NO 64
<211> LENGTH: 324
<212> TYPE: DNA
<213> ORGANISM: Artificial Sequence
<220> FEATURE:
<223> OTHER INFORMATION: 15F7 mature light chain variable region

<400> SEQUENCE: 64

```
gacatccaga tgacacaatc ttcatcctcc ttttctgtat ctctaggaga cagagtcacc      60
attacttgca aggcaagtga ggacatatat aatcggttag cctggtatca gcagaaacca     120
ggaaatgctc ctaggctctt aatatctggt gcaaccagtt tggaaactgg ggttccttca     180
agattcagtg gcagtggatc tggaaaggat tacactctca gcattaccag tcttcagact     240
gaagatgttg ctacttatta ctgtcaacag tattggagta ttccgtacac gttcggaggg     300
gggaccaacc tggaaataaa acgg                                            324
```

<210> SEQ ID NO 65
<211> LENGTH: 57
<212> TYPE: DNA
<213> ORGANISM: Artificial Sequence
<220> FEATURE:
<223> OTHER INFORMATION: 15F7 heavy chain variable region signal peptide

<400> SEQUENCE: 65

```
atggaatgga tctggagctt tctcttcatc ctgtcaggaa ctgcaggtgt ccaatcc         57
```

<210> SEQ ID NO 66
<211> LENGTH: 81
<212> TYPE: DNA
<213> ORGANISM: Artificial Sequence
<220> FEATURE:
<223> OTHER INFORMATION: 15F7 light chain variable region signal peptide

<400> SEQUENCE: 66

```
atgtcaagtc acagcagaaa catgaagttt ccttctcaac ttctgctctt actgctgttt      60
ggaatcccag gcatgatatg t                                                81
```

<210> SEQ ID NO 67
<211> LENGTH: 357
<212> TYPE: DNA
<213> ORGANISM: Artificial Sequence
<220> FEATURE:
<223> OTHER INFORMATION: 6C12 mature heavy chain variable region

<400> SEQUENCE: 67

```
caggtccaac tgcagcagcc tggggctgag ttggtaaagc ctggggcttc agtgaaattg      60
tcctgcaagg cttctggcta cacattcacc acctactgga tgcactgggt gaagcagagg     120
cctggacaag cccctgagtg gattggaatg attcatcctt atagtggtgc cattaactat     180
aatgagaagt tcaagagcaa ggccacactg actgtagaca atcctccag cacagcctac      240 atgcaactca gcagcctgac atctgaggac tctgcggtct attactgtgt aaaacagctc     300
aggctcctct actactttga ctactggggc caaggcacca ctctcacggt ctcctca        357
```

<210> SEQ ID NO 68
<211> LENGTH: 342
<212> TYPE: DNA
<213> ORGANISM: Artificial Sequence
<220> FEATURE:
<223> OTHER INFORMATION: 6C12 mature light chain variable region, v1

<400> SEQUENCE: 68

```
gacattgtga tgacacagtc tccatcctcc ctgactgtga cagcaggaga gaaggtcact      60
atgagctgca agtccagaca gagtctatta acagtggaa atcaaaagaa ctacttgacc      120
tggtaccaac agaaaccagg gcagcctcct aaagtgttga tctactgggc atccactagg    180
gaatctgggg tccctgatcg cttcacaggc agtggatctg gaacagattt cactctcacc    240
atcagcagtg tgcaggctga agacctggca gtttattact gtcagaatga ttatagttat   300
ccgctcacgt tcggtgctgg gaccaagctg gagctgaaac gg                        342
```

<210> SEQ ID NO 69
<211> LENGTH: 57
<212> TYPE: DNA
<213> ORGANISM: Artificial Sequence
<220> FEATURE:
<223> OTHER INFORMATION: 6C12 heavy chain variable region signal peptide

<400> SEQUENCE: 69

```
atgggatgga gctatatcat cctctttttg gtagcaacag ctacaggtgt ccactcc        57
```

<210> SEQ ID NO 70
<211> LENGTH: 60
<212> TYPE: DNA
<213> ORGANISM: Artificial Sequence
<220> FEATURE:
<223> OTHER INFORMATION: 6C12 light chain variable region signal peptide

<400> SEQUENCE: 70

```
atggaatcac agactcaggt cctcatgtcc ctgctgttct gggtatctgg tacctgtggg     60
```

<210> SEQ ID NO 71
<211> LENGTH: 363
<212> TYPE: DNA
<213> ORGANISM: Artificial Sequence
<220> FEATURE:
<223> OTHER INFORMATION: 13G10 mature heavy chain variable region, v1

<400> SEQUENCE: 71

```
caggttcagc tgcagcagtc tggagctgaa ctggcgaggc ctggggcttc agtgaagctg     60
tcctgcaagg cttctggcta caccttcaca aactatggaa taagctgggt gaagcagaga   120
actggacagg gccttgagtg gattggagcg atttatccta gaagtggtaa tacttactac    180
aatgagaagt tcaagggcaa ggccacactg actgcagaca atcctccag cacagcgtac     240 atggagctcc gcagcctgac atctgaggac tctgcggtct atttctgtgc aagagaaagg   300
gactacggta gtagctacgc tctggactac tggggtcaag gaacctcagt caccgtctcc   360
tca                                                                  363
```

<210> SEQ ID NO 72
<211> LENGTH: 357
<212> TYPE: DNA
<213> ORGANISM: Artificial Sequence
<220> FEATURE:
<223> OTHER INFORMATION: 13G10 mature heavy chain variable region, v2

<400> SEQUENCE: 72

```
caggtccaac tgcagcagcc tggggctgag ctggtaaagc ctggggcttc agtgaagttg     60
tcctgcaagg cttctggcta cactttcacc agctactgga tgcactgggt gaagcagagg   120
cctggacaag gccttgagtg gattggaatg attcatcctc atagtggtag tactaactac    180
aatgagaagt tcaagagcaa ggccacactg actgtagaca gtcctccag cacagcctac     240 atgcaactca gcagcctgac atctgaggac tctgcggtct attactgtgc aagacagctc   300
```
aggctactct actactttga ctactggggc caaggcacca ctctcacagt ctcctca      357

<210> SEQ ID NO 73
<211> LENGTH: 324
<212> TYPE: DNA
<213> ORGANISM: Artificial Sequence
<220> FEATURE:
<223> OTHER INFORMATION: 13G10 mature light chain variable region

<400> SEQUENCE: 73
gacatccaga tgacacaatc ttcatcctcc ttttctgtat ctctaggaga cagagtcacc      60
attacttgca aggcaagtga ggacatatat aatcggttag cctggtatca gcagaaacca     120
ggaaatgctc ctaggctctt aatatctggt gcaaccagtt tggaaactgg ggttccttca     180
agattcactg gcagtggatc tggaaaggat tacactctca gcattaccag tcttcagact     240
gaagatgttg ctacttatta ctgtcaacag tattggagtc ctcctcggac gttcggtgga     300
ggcaccaagc tggaaatcaa acgg                                            324

<210> SEQ ID NO 74
<211> LENGTH: 57
<212> TYPE: DNA
<213> ORGANISM: Artificial Sequence
<220> FEATURE:
<223> OTHER INFORMATION: 13G10 heavy chain variable region signal
      peptide, v1

<400> SEQUENCE: 74
atggaatgga tctggatctt tctcttcatc ctgtcaggaa ctgcaggtgt ccaatcc         57

<210> SEQ ID NO 75
<211> LENGTH: 57
<212> TYPE: DNA
<213> ORGANISM: Artificial Sequence
<220> FEATURE:
<223> OTHER INFORMATION: 13G10 heavy chain variable region signal
      peptide, v2

<400> SEQUENCE: 75
atgggatgga gctatatcat cctcttttg gtagcaacag ctacaggtgt ccactcc         57

<210> SEQ ID NO 76
<211> LENGTH: 60
<212> TYPE: DNA
<213> ORGANISM: Artificial Sequence
<220> FEATURE:
<223> OTHER INFORMATION: 13G10 light chain variable region signal
      peptide

<400> SEQUENCE: 76
atgaagtttc cttctcaact tctgctctta ctgctgtttg gaatcccagg catgatatgt       60

<210> SEQ ID NO 77
<211> LENGTH: 357
<212> TYPE: DNA
<213> ORGANISM: Artificial Sequence
<220> FEATURE:
<223> OTHER INFORMATION: Synthetic

<400> SEQUENCE: 77
gaggttcagc tgcagcagtc tggagctgag gtgaagaagc ctgggagtag tgtgaagctg       60
tcctgcaagg cttcaggcta taccttcaca agttatggtt taagctgggt gaagcagaga     120
gctggacagg gccttgagtg gattggagag attttttccta gaagtggtaa tacttactac     180
aatgagaagt tcaagggcaa ggccacactg actgcagaca aatcctccag cacagcgtac      240
atggagctcc gcagcctgag atctgaggac actgcggtct atttctgtgc aagagggggtt     300 cgtagccccg gggctatgga ctactggggt caaggaaccc tagtcaccgt ctcctca         357

<210> SEQ ID NO 78
<211> LENGTH: 357
<212> TYPE: DNA
<213> ORGANISM: Artificial Sequence
<220> FEATURE:
<223> OTHER INFORMATION: Synthetic

<400> SEQUENCE: 78
gaggttcagc tgcagcagtc tggagctgag gtgaagaagc ctggagtag tgtgaagctg         60 tcctgcaagg cttcaggcta taccttcaca agttatggtt taagctgggt gaagcagaga      120
cctggacagg gccttgagtg gattggagag atttttccta gaagtggtaa tacttactac      180
aatgagaagt tcaagggcaa ggccacaatc actgcagaca aatcctccag cacagcgtac      240
atggagctcc gcagcctgag atctgaggac actgcggtct atttctgtgc aagagggggtt     300 cgtagccccg gggctatgga ctactggggt caaggaaccc tagtcaccgt ctcctca         357

<210> SEQ ID NO 79
<211> LENGTH: 324
<212> TYPE: DNA
<213> ORGANISM: Artificial Sequence
<220> FEATURE:
<223> OTHER INFORMATION: Synthetic

<400> SEQUENCE: 79
gacatccaga tgacacaatc ttcatcctcc ctttctgcat ctgtaggaga cagagtcacc        60
attacttgca aggcaagtga ggacatatat aatcggttag cctggtatca gcagaaacca      120
ggaaatgctc ctaggctctt aatatctggt gcaaccagtt tggaaactgg ggttccttca      180
agattcagtg gcagtggatc tggaaaggat tacactctca ccattagcag tcttcagact      240
gaagattttg ctacttatta ctgtcaacag tattggagta ttccgtacac gttcggaggg      300
gggaccaaag tggaaataaa acgt                                             324

<210> SEQ ID NO 80
<211> LENGTH: 324
<212> TYPE: DNA
<213> ORGANISM: Artificial Sequence
<220> FEATURE:
<223> OTHER INFORMATION: Synthetic

<400> SEQUENCE: 80
gacatccaga tgacacaatc tccatcctcc ctttctgcat ctgtaggaga cagagtcacc        60
attacttgca aggcaagtga ggacatatat aatcggttag cctggtatca gcagaaacca      120
ggaaatgctc ctaagctctt aatatctggt gcaaccagtt tggaaactgg ggttccttca      180
agattcagtg gcagtggatc tggaaaggat ttcactctca ccattagcag tcttcagcct      240
gaagattttg ctacttatta ctgtcaacag tattggagta ttccgtacac gttcggaggg      300
gggaccaaag tggaaataaa acgt                                             324

<210> SEQ ID NO 81
<211> LENGTH: 2976
<212> TYPE: DNA
<213> ORGANISM: Artificial Sequence
<220> FEATURE:

<223> OTHER INFORMATION: G domain of human LAMA4

<400> SEQUENCE: 81

```
agcaagatcc aagtctccat gatgtttgat ggccagtcag ctgtggaagt gcactcgaga      60
accagtatgg atgacttaaa ggccttcacg tctctgagcc tgtacatgaa accccctgtg     120
aagcggccgg aactgaccga gactgcagat cagtttatcc tgtacctcgg aagcaaaaac     180
gccaaaaaag agtatatggg tcttgcaatc aaaaatgata atctggtata cgtctataat     240
ttgggaacta agatgtggag gattcccctg gactccaagc ccgtcagttc ctggcctgct     300
tacttcagca ttgtcaagat tgaaaggggtg ggaaaacatg gaaaggtgtt tttaacagtc     360
ccgagtctaa gtagcacagc agaggaaaag ttcattaaaa aggggaatt ttcgggagat     420
gactctctgc tggacctgga ccctgaggac acagtgtttt atgttggtgg agtgccttcc     480
aacttcaagc tccctaccag cttaaacctg cctggctttg ttggctgcct ggaactggcc     540
actttgaata atgatgtgat cagcttgtac aactttaagc acatctataa tatggacccc     600
tccacatcag tgccatgtgc ccgagataag ctggccttca ctcagagtcg ggctgccagt     660
tacttcttcg atggctccgg ttatgccgtg tgagagaca tcacaaggag agggaaattt     720
ggtcaggtga ctcgctttga catagaagtt cgaacaccag ctgacaacgg ccttattctc     780
ctgatggtca atggaagtat gtttttcaga ctggaaatgc gcaatggtta cctacatgtg     840
ttctatgatt ttggattcag cagtggccgt gtgcatcttg aagatacgtt aaagaaagct     900
caaattaatg atgcaaaata ccatgagatc tcaatcattt accacaatga taagaaaatg     960
atcttggtag ttgacagaag gcatgtcaag agcatggata tgaaaagat gaaaataccct    1020
tttacagata tatacattgg aggagctcct ccagaaatct acaatccag gcccctcaga    1080
gcacaccttc ccctagatat caacttcaga ggatgcatga agggcttcca gttccaaaag    1140
aaggacttca atttactgga gcagacagaa accctgggag ttggttatgg atgcccagaa    1200
gactcactta tatctcgcag agcatatttc aatggacaga gcttcattgc ttcaattcag    1260
aaaatatctt tctttgatgg ctttgaagga ggttttaatt tccgaacatt acaaccaaat    1320
gggttactat tctattatgc ttcagggtca gacgtgttct ccatctcact ggataatggt    1380
actgtcatca tggatgtaaa gggaatcaaa gttcagtcag tagataagca gtacaatgat    1440
gggctgtccc acttcgtcat tagctctgtc tcacccacaa gatatgaact gatagtagat    1500
aaaagcagag ttgggagtaa gaatcctacc aaagggaaaa tagaacagac acaagcaagt    1560
gaaaagaagt tttacttcgg tggctcacca atcagtgctc agtatgctaa tttcactggc    1620
tgcataagta atgcctactt taccagggtg gatagagatg tggaggttga agatttccaa    1680
cggtatactg aaaaggtcca cacttctctt tatgagtgtc ccattgagtc ttcaccattg    1740
tttctcctcc ataaaaaagg aaaaaattta tccaagccta agcaagtcaa gaataaaaag    1800
ggagggaaaa gtaaagatgc accttcatgg gatcctgttg ctctgaaact cccagagcgg    1860
aatactccaa gaaactctca ttgccaccttt tccaacagcc ctagagcaat agagcacgcc    1920
tatcaatatg gaggaacagc caacagccgc caagagtttg aacacttaaa aggagatttt    1980
ggtgccaaat ctcagttttc cattcgtctg agaactcgtt cctcccatgg catgatcttc    2040
tatgtctcag atcaagaaga gaatgacttc atgactctat ttttggccca tggccgcttg    2100
gtttacatgt ttaatgttgg tcacaaaaaa ctgaagatta gaagccagga gaaatacaat    2160
gatgcctgt ggcatgatgt gatatttatt cgagaaggaa gcagtggccg actggtaatt    2220
gatggtctcc gagtcctaga agaaagtctt cctcctactg aagctacctg gaaaatcaag    2280
```

```
ggtcccattt atttgggagg tgtggctcct ggaaaggctg tgaaaaatgt tcagattaac    2340
tccatctaca gttttagtgg ctgtctcagc aatctccagc tcaatggggc ctccatcacc    2400
tctgcttctc agacattcag tgtgacccct tgctttgaag gccccatgga aacaggaact    2460
tacttttcaa cagaaggagg atacgtggtt ctagatgaat ctttcaatat tggattgaag    2520
tttgaaattg catttgaagt ccgtcccaga agcagttccg gaaccctggt ccacggccac    2580
agtgtcaatg gggagtacct aaatgttcac atgaaaaatg acaggtcat agtgaaagtc     2640 aataatggca tcagagattt ttccacctca gtaacaccca agcagagtct ctgtgatggc    2700
agatggcaca gaattacagt tattagagat tctaatgtgg ttcagttgga tgtggactct    2760
gaagtgaacc atgtggttgg acccctgaat ccaaaaccaa ttgatcacag ggagcctgtg    2820
tttgttggag tgttccaga atctctactg acaccacgct tggcccccag caaacccttc     2880
acaggctgca tacgccactt tgtgattgat ggacacccag tgagcttcag taaagcagcc    2940
ctggtcagcg gcgccgtaag catcaactcc tgtcca                              2976

<210> SEQ ID NO 82
<211> LENGTH: 618
<212> TYPE: DNA
<213> ORGANISM: Artificial Sequence
<220> FEATURE:
<223> OTHER INFORMATION: LG1 module of G domain of human LAMA4

<400> SEQUENCE: 82
agcaagatcc aagtctccat gatgtttgat ggccagtcag ctgtggaagt gcactcgaga     60
accagtatgg atgacttaaa ggccttcacg tctctgagcc tgtacatgaa accccctgtg    120
aagcggccgg aactgaccga gactgcagat cagtttatcc tgtacctcgg aagcaaaaac    180
gccaaaaaag agtatatggg tcttgcaatc aaaaatgata atctggtata cgtctataat    240
ttgggaacta aagatgtgga gattcccctg gactccaagc ccgtcagttc ctggcctgct    300
tacttcagca ttgtcaagat tgaaaggggtg ggaaaacatg gaaggtgtt tttaacagtc    360 ccgagtctaa gtagcacagc agaggaaaag ttcattaaaa aggggggaatt ttcgggagat    420 gactctctgc tggacctgga ccctgaggac acagtgtttt atgttggtgg agtgccttcc    480
aacttcaagc tccctaccag cttaaacctg cctggctttg ttggctgcct ggaactggcc    540
actttgaata tgatgtgat cagcttgtac aactttaagc acatctataa tatggacccc    600
tccacatcag tgccatgt                                                 618

<210> SEQ ID NO 83
<211> LENGTH: 540
<212> TYPE: DNA
<213> ORGANISM: Artificial Sequence
<220> FEATURE:
<223> OTHER INFORMATION: LG2 module of G domain of human LAMA4

<400> SEQUENCE: 83
gccagttact tcttcgatgg ctccggttat gccgtggtga gagacatcac aaggagaggg     60
aaatttggtc aggtgactcg ctttgacata gaagttcgaa caccagctga caacggcctt    120
attctcctga tggtcaatgg aagtatgttt ttcagactgg aaatgcgcaa tggttaccta    180
catgtgttct atgattttgg attcagcagt ggccgtgtgc atcttgaaga tacgttaaag    240
aaagctcaaa ttaatgatgc aaaataccat gagatctcaa tcatttacca caatgataag    300
aaaatgatct tggtagttga cagaaggcat gtcaagagca tggataatga aagatgaaa    360
```

| | |
|---|---|
| atacctttta cagatatata cattggagga gctcctccag aaatcttaca atccagggcc | 420 |
| ctcagagcac accttcccct agatatcaac ttcagaggat gcatgaaggg cttccagttc | 480 |
| caaaagaagg acttcaattt actggagcag acagaaaccc tgggagttgg ttatggatgc | 540 |

<210> SEQ ID NO 84
<211> LENGTH: 507
<212> TYPE: DNA
<213> ORGANISM: Artificial Sequence
<220> FEATURE:
<223> OTHER INFORMATION: LG3 module of G domain of human LAMA4

<400> SEQUENCE: 84

| | |
|---|---|
| tctcgcagag catatttcaa tggacagagc ttcattgctt caattcagaa aatatctttc | 60 |
| tttgatggct tgaaggagg ttttaatttc cgaacattac aaccaaatgg ttactattc | 120 |
| tattatgctt cagggtcaga cgtgttctcc atctcactgg ataatggtac tgtcatcatg | 180 |
| gatgtaaagg gaatcaaagt tcagtcagta gataagcagt acaatgatgg gctgtcccac | 240 |
| ttcgtcatta gctctgtctc acccacaaga tatgaactga tagtagataa agcagagtt | 300 |
| gggagtaaga atcctaccaa agggaaaata gaacagacac aagcaagtga aaagaagttt | 360 |
| tacttcggtg gctcaccaat cagtgctcag tatgctaatt tcactggctg cataagtaat | 420 |
| gcctactta ccagggtgga tagagatgtg gaggttgaag attccaacg gtatactgaa | 480 |
| aaggtccaca cttctctta tgagtgt | 507 |

<210> SEQ ID NO 85
<211> LENGTH: 1803
<212> TYPE: DNA
<213> ORGANISM: Artificial Sequence
<220> FEATURE:
<223> OTHER INFORMATION: LG1-3 modules of G domain of human LAMA4

<400> SEQUENCE: 85

| | |
|---|---|
| agcaagatcc aagtctccat gatgtttgat ggccagtcag ctgtggaagt gcactcgaga | 60 |
| accagtatgg atgacttaaa ggccttcacg tctctgagcc tgtacatgaa acccccgtg | 120 |
| aagcggccgg aactgaccga gactgcagat cagtttatcc tgtacctcgg aagcaaaaac | 180 |
| gccaaaaaag agtatatggg tcttgcaatc aaaaatgata atctggtata cgtctataat | 240 |
| ttgggaacta aagatgtgga gattcccctg gactccaagc ccgtcagttc ctggcctgct | 300 |
| tacttcagca ttgtcaagat gaaagggtg ggaaaacatg gaaggtgtt tttaacagtc | 360 |
| ccgagtctaa gtagcacagc agaggaaaag ttcattaaaa aggggaatt tcgggagat | 420 |
| gactctctgc tggacctgga ccctgaggac acagtgtttt atgttggtgg agtgccttcc | 480 |
| aacttcaagc tccctaccag cttaaacctg cctggctttg ttggctgcct ggaactggcc | 540 |
| actttgaata atgatgtgat cagcttgtac aactttaagc acatctataa tatggacccc | 600 |
| tccacatcag tgcatgtgc ccgagataag ctggccttca ctcagagtcg ggctgccagt | 660 |
| tacttcttcg atggctccgg ttatgccgtg gtgagagaca tcacaaggag agggaaattt | 720 |
| ggtcaggtga ctcgctttga catagaagtt cgaacaccag ctgacaacgg ccttattctc | 780 |
| ctgatggtca atggaagtat gtttttcaga ctggaaatgc gcaatggtta cctacatgtg | 840 |
| ttctatgatt ttggattcag cagtggccgt gtgcatcttg aagatacgtt aagaaaagct | 900 |
| caaattaatg atgcaaaata ccatgagatc tcaatcattt accacaatga taagaaaatg | 960 |
| atcttggtag ttgacagaag gcatgtcaag agcatggata atgaaaagat gaaaatacct | 1020 |
| tttacagata tatacattgg aggagctcct ccagaaatct tacaatccag ggccctcaga | 1080 |

```
gcacaccttc ccctagatat caacttcaga ggatgcatga agggcttcca gttccaaaag    1140
aaggacttca atttactgga gcagacagaa accctgggag ttggttatgg atgcccagaa    1200
gactcactta tatctcgcag agcatatttc aatggacaga gcttcattgc ttcaattcag    1260
aaaatatctt tctttgatgg ctttgaagga ggttttaatt tccgaacatt acaaccaaat    1320
gggttactat tctattatgc ttcagggtca gacgtgttct ccatctcact ggataatggt    1380
actgtcatca tggatgtaaa gggaatcaaa gttcagtcag tagataagca gtacaatgat    1440
gggctgtccc acttcgtcat tagctctgtc tcacccacaa gatatgaact gatagtagat    1500
aaaagcagag ttgggagtaa gaatcctacc aaagggaaaa tagaacagac acaagcaagt    1560
gaaaagaagt tttacttcgg tggctcacca atcagtgctc agtatgctaa tttcactggc    1620
tgcataagta atgcctactt taccagggtg gatagagatg tggaggttga agatttccaa    1680
cggtatactg aaaaggtcca cacttctctt tatgagtgtc ccattgagtc ttcaccattg    1740
tttctcctcc ataaaaaagg aaaaaattta tccaagccta agcaagtca gaataaaaag    1800 gga                                                                 1803

<210> SEQ ID NO 86
<211> LENGTH: 513
<212> TYPE: DNA
<213> ORGANISM: Artificial Sequence
<220> FEATURE:
<223> OTHER INFORMATION: LG4 module of G domain of human LAMA4

<400> SEQUENCE: 86
tatcaatatg gaggaacagc caacagccgc caagagtttg aacacttaaa aggagatttt     60
ggtgccaaat ctcagttttc cattcgtctg agaactcgtt cctcccatgg catgatcttc    120
tatgtctcag atcaagaaga gaatgacttc atgactctat ttttggccca tggccgcttg    180
gtttacatgt ttaatgttgg tcacaaaaaa ctgaagatta gaagccagga gaaatacaat    240
gatggcctgt ggcatgatgt gatatttatt cgagaaagga gcagtggccg actggtaatt    300
gatggtctcc gagtcctaga agaaagtctt cctcctactg aagctacctg gaaaatcaag    360
ggtcccattt atttgggagg tgtggctcct ggaaaggctg tgaaaaatgt tcagattaac    420
tccatctaca gttttagtgg ctgtctcagc aatctccagc tcaatggggc ctccatcacc    480
tctgcttctc agacattcag tgtgacccct tgc                                513

<210> SEQ ID NO 87
<211> LENGTH: 522
<212> TYPE: DNA
<213> ORGANISM: Artificial Sequence
<220> FEATURE:
<223> OTHER INFORMATION: LG5 module of G domain of human LAMA4

<400> SEQUENCE: 87
acaggaactt acttttcaac agaaggagga tacgtggttc tagatgaatc tttcaatatt     60
ggattgaagt ttgaaattgc atttgaagtc cgtcccagaa gcagttccgg aaccctggtc    120
cacggccaca gtgtcaatgg ggagtaccta aatgttcaca tgaaaaatgg acaggtcata    180
gtgaaagtca ataatggcat cagagatttt tccacctcag taacacccaa gcagagtctc    240
tgtgatggca gatggcacag aattacagtt attagagatt ctaatgtggt tcagttggat    300
gtggactctg aagtgaacca tgtggttgga cccctgaatc aaaaccaat tgatcacagg    360 gagcctgtgt ttgttggagg tgttccagaa tctctactga caccacgctt ggccccagc    420
```

```
aaacccttca caggctgcat acgccacttt gtgattgatg acacccagt gagcttcagt      480 aaagcagccc tggtcagcgg cgccgtaagc atcaactcct gt                        522
```

<210> SEQ ID NO 88
<211> LENGTH: 1107
<212> TYPE: DNA
<213> ORGANISM: Artificial Sequence
<220> FEATURE:
<223> OTHER INFORMATION: LG4-5 modules of G domain of human LAMA4

<400> SEQUENCE: 88

```
agaaactctc attgccacct ttccaacagc cctagagcaa tagagcacgc ctatcaatat       60
ggaggaacag ccaacagccg ccaagagttt gaacacttaa aaggagattt tggtgccaaa     120
tctcagtttt ccattcgtct gagaactcgt tcctcccatg gcatgatctt ctatgtctca     180
gatcaagaag agaatgactt catgactcta tttttggccc atggccgctt ggtttacatg     240
tttaatgttg gtcacaaaaa actgaagatt agaagccagg agaaatacaa tgatggcctg     300
tggcatgatg tgatatttat tcgagaaagg agcagtggcc gactggtaat tgatggtctc     360
cgagtcctag aagaaagtct tcctcctact gaagctacct ggaaaatcaa gggtcccatt     420
tatttgggag gtgtggctcc tggaaaggct gtgaaaaatg ttcagattaa ctccatctac     480
agttttagtg gctgtctcag caatctccag ctcaatgggg cctccatcac ctctgcttct     540
cagacattca gtgtgacccc ttgctttgaa ggccccatgg aaacaggaac ttacttttca     600
acagaaggag gatacgtggt tctagatgaa tctttcaata ttggattgaa gtttgaaatt     660
gcatttgaag tccgtcccag aagcagttcc ggaaccctgg tccacggcca cagtgtcaat     720
ggggagtacc taaatgttca catgaaaaat ggacaggtca tagtgaaagt caataatggc     780
atcagagatt tttccacctc agtaacaccc aagcagagtc tctgtgatgg cagatggcac     840
agaattacag ttattagaga ttctaatgtg gttcagttgg atgtggactc tgaagtgaac     900
catgtggttg gacccctgaa tccaaaaacca attgatcaca gggagcctgt gtttgttgga     960
ggtgttccag aatctctact gacaccacgc ttggccccca gcaaacccctt cacaggctgc    1020 atacgccact tgtgattga tggacacccca gtgagcttca gtaaagcagc cctggtcagc    1080
ggcgccgtaa gcatcaactc ctgtcca                                        1107
```

<210> SEQ ID NO 89
<211> LENGTH: 330
<212> TYPE: PRT
<213> ORGANISM: Artificial Sequence
<220> FEATURE:
<223> OTHER INFORMATION: Exemplary human IgG1 constant region of IgG1
    G1m3 allotype

<400> SEQUENCE: 89

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 90
<211> LENGTH: 107
<212> TYPE: PRT
<213> ORGANISM: Artificial Sequence
<220> FEATURE:
<223> OTHER INFORMATION: Exemplary human kappa light chain constant
      region with a N-terminal arginine

<400> SEQUENCE: 90

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 91
<211> LENGTH: 329
<212> TYPE: PRT
<213> ORGANISM: Artificial Sequence
<220> FEATURE:
<223> OTHER INFORMATION: Exemplary human IgG1 constant region without a
      C-terminal lysine

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 92
<211> LENGTH: 990
<212> TYPE: DNA
<213> ORGANISM: Artificial Sequence
<220> FEATURE:
<223> OTHER INFORMATION: Exemplary human IgG1 constant region of IgG1
    G1m3 allotype

<400> SEQUENCE: 92

```
gcctccacca agggtccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga    360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                      990
```

<210> SEQ ID NO 93
<211> LENGTH: 321
<212> TYPE: DNA
<213> ORGANISM: Artificial Sequence
<220> FEATURE:
<223> OTHER INFORMATION: Exemplary human kappa light chain constant
    region with a N-terminal arginine

<400> SEQUENCE: 93

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321
```

<210> SEQ ID NO 94
<211> LENGTH: 114
<212> TYPE: PRT
<213> ORGANISM: Artificial Sequence
<220> FEATURE:
<223> OTHER INFORMATION: 6C12 mature light chain variable region, v2

<400> SEQUENCE: 94

```
Asp Ile Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
```

```
Gly Asn Gln Lys Asn Tyr Leu Thr Trp Tyr Gln Gln Lys Pro Gly Gln
        35                  40                  45

Pro Pro Lys Val Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Leu
            100                 105                 110

Lys Arg
```

```
<210> SEQ ID NO 95
<211> LENGTH: 17
<212> TYPE: PRT
<213> ORGANISM: Artificial Sequence
<220> FEATURE:
<223> OTHER INFORMATION: 6C12 CDR-L1, v2

<400> SEQUENCE: 95

Lys Ser Ser Gln Ser Leu Leu Asn Ser Gly Asn Gln Lys Asn Tyr Leu
 1               5                   10                  15

Thr
```

```
<210> SEQ ID NO 96
<211> LENGTH: 121
<212> TYPE: PRT
<213> ORGANISM: Artificial Sequence
<220> FEATURE:
<223> OTHER INFORMATION: Human VH acceptor FR, v3

<400> SEQUENCE: 96

Gln Val Gln Leu Val Gln Ser Gly Thr Glu Val Lys Lys Pro Gly Ser
 1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Val Gly Ile Gly Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Val Asp Phe Asp Ser Ser Ser Tyr Ser Phe Trp Gly
            100                 105                 110

Gln Gly Thr Leu Val Thr Val Ser Ser
            115                 120
```

```
<210> SEQ ID NO 97
<211> LENGTH: 119
<212> TYPE: PRT
<213> ORGANISM: Artificial Sequence
<220> FEATURE:
<223> OTHER INFORMATION: Human VH acceptor FR, v4

<400> SEQUENCE: 97

Gln Val Gln Leu Gln Gln Ser Gly Ala Glu Val Lys Lys Pro Gly Ser
 1               5                   10                  15
```

-continued

Ser Val Lys Val Ser Cys Lys Ala Ser Gly Thr Phe Ser Ser Tyr
             20                  25                  30

Ala Ile Ser Trp Val Arg Gln Ala Pro Gly Gln Gly Leu Glu Trp Met
         35                  40                  45

Gly Arg Ile Ile Pro Ile Leu Gly Ile Ala Asn Tyr Ala Gln Lys Phe
     50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Asp Thr His Ser Trp Phe Ala Phe Asp Ile Trp Gly Gln Gly
             100                 105                 110

Thr Met Val Thr Val Ser Ser
        115

<210> SEQ ID NO 98
<211> LENGTH: 108
<212> TYPE: PRT
<213> ORGANISM: Artificial Sequence
<220> FEATURE:
<223> OTHER INFORMATION: Human VL acceptor FR, v3

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Ser Asn Ser
             20                  25                  30

Leu Ala Trp Tyr Gln Gln Lys Pro Gly Lys Ala Pro Lys Leu Leu Leu
         35                  40                  45

Tyr Ala Ala Ser Arg Leu Glu Ser Gly Val Pro Ser Arg Phe Ser Gly
     50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Gln
                 85                  90                  95

Thr Phe Gly Gln Gly Thr Lys Leu Glu Ile Lys Arg
            100                 105

<210> SEQ ID NO 99
<211> LENGTH: 342
<212> TYPE: DNA
<213> ORGANISM: Artificial Sequence
<220> FEATURE:
<223> OTHER INFORMATION: 6C12 mature light chain variable region, v2

<400> SEQUENCE: 99
gacattgtga tgacacagtc tccatcctcc ctgactgtga cagcaggaga gaaggtcact     60
atgagctgca gtccagtca gagtctatta acagtggaa atcaaaagaa ctacttgacc     120
tggtaccaac agaaaccagg gcagcctcct aaagtgttga tctactgggc atccactagg    180
gaatctgggg tccctgatcg cttcacaggc agtggatctg gaacagattt cactctcacc    240
atcagcagtg tgcaggctga agacctggca gtttattact gtcagaatga ttatagttat    300
ccgctcacgt tcggtgctgg gaccaagctg gagctgaaac gg                       342

<210> SEQ ID NO 100
<211> LENGTH: 324
<212> TYPE: DNA
<213> ORGANISM: Artificial Sequence
<220> FEATURE:
<223> OTHER INFORMATION: Synthetic

<400> SEQUENCE: 100

```
gacatccaga tgacacaatc ttcatcctcc ctttctgcat ctgtaggaga cagagtcacc    60
attacttgca aggcaagtga ggacatatat aatcggttag cctggtatca gcagaaacca   120
ggaaatgctc ctaggctctt aatatctggt gcaaccagtt tggaaactgg ggttccttca   180
agattcagtg gcagtggatc tggaaaggat tacactctca ccattagcag tcttcagact   240
gaagattttg ctacttatta ctgtcaacag tattggagta ttccgtacac gttcggaggg   300
gggaccaaat tggaaataaa acgt                                          324
```

<210> SEQ ID NO 101
<211> LENGTH: 330
<212> TYPE: PRT
<213> ORGANISM: Artificial Sequence
<220> FEATURE:
<223> OTHER INFORMATION: Exemplary human IgG1 constant region of IgG1
       G1m3 allotype

<400> SEQUENCE: 101

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 102
<211> LENGTH: 318
<212> TYPE: DNA
<213> ORGANISM: Artificial Sequence
<220> FEATURE:
<223> OTHER INFORMATION: Exemplary human kappa light chain constant
      region without a N-terminal arginine

<400> SEQUENCE: 102
actgtggctg caccatctgt cttcatcttc ccgccatctg atgagcagtt gaaatctgga        60
actgcctctg ttgtgtgcct gctgaataac ttctatccca gagaggccaa agtacagtgg       120
aaggtggata acgccctcca atcgggtaac tcccaggaga gtgtcacaga gcaggacagc       180
aaggacagca cctacagcct cagcagcacc ctgacgctga gcaaagcaga ctacgagaaa       240
cacaaagtct acgcctgcga agtcacccat cagggcctga gctcgcccgt cacaaagagc       300
ttcaacaggg gagagtgt                                                     318
```